United States Patent
Kirkby et al.

(10) Patent No.: US 8,294,977 B2
(45) Date of Patent: Oct. 23, 2012

(54) IMAGING APPARATUS AND METHODS

(75) Inventors: Paul Anthony Kirkby, London (GB); Robin Angus Silver, London (GB); K. M. Naga Srinivas Nadella, London (GB)

(73) Assignee: UCL Business PLC, London (GB)

( * ) Notice: Subject to any disclaimer, the term of this patent is extended or adjusted under 35 U.S.C. 154(b) by 574 days.

(21) Appl. No.: 12/440,809

(22) PCT Filed: Sep. 12, 2007

(86) PCT No.: PCT/GB2007/003455
§ 371 (c)(1),
(2), (4) Date: Nov. 25, 2009

(87) PCT Pub. No.: WO2008/032061
PCT Pub. Date: Mar. 20, 2008

(65) Prior Publication Data
US 2010/0328759 A1    Dec. 30, 2010

(30) Foreign Application Priority Data

Sep. 12, 2006  (GB) .................................. 0617945.1

(51) Int. Cl.
*G02F 1/33* (2006.01)
*G02F 1/11* (2006.01)
(52) U.S. Cl. ......... 359/310; 359/285; 359/311; 359/312
(58) Field of Classification Search .................. 359/285, 359/305, 308–309, 311–312
See application file for complete search history.

(56) References Cited

U.S. PATENT DOCUMENTS

| | | | |
|---|---|---|---|
| 3,944,948 A | 3/1976 | Redman et al. | |
| 4,217,036 A | 8/1980 | Chang | |
| 4,371,964 A | 2/1983 | Podmaniczky et al. | |
| 4,435,041 A | 3/1984 | Torok et al. | |

(Continued)

FOREIGN PATENT DOCUMENTS

EP    0485191    5/1992

(Continued)

OTHER PUBLICATIONS

Reddy, G. D. et al: "Fast three-dimensional laser scanning scheme using acousto-optical deflectors," Journal of Biomedical Optics SPIE USA, vol. 1-, No. 6, Nov. 2005, pp. 64038-1, XP002471695, ISSN: 1083-3668.

(Continued)

*Primary Examiner* — Dawayne A Pinkney
(74) *Attorney, Agent, or Firm* — Harness, Dickey & Pierce, P.L.C.

(57) ABSTRACT

Methods, systems and apparatus for manipulating electromagnetic radiation such as laser beams. A method and apparatus for correcting magnification chromatic aberration utilizes one or more dispersive lenses such that long wavelength components are magnified less than short wavelength components. A telecentric relay is preferred to achieve this aim. Further, the use of polarizers to block the undesired zeroth order components of diffraction emanating from acousto-optic deflectors (AODs) is disclosed. Furthermore, specific designs of AOD including narrow transducer AODs which produce a diverging acoustic wave and AODs having two transducers and a selection switch are disclosed. Further, the invention provides methods, systems and apparatus for allowing the wavelength of radiation to be changed, for providing a user selectable degree of compensation, for providing a scanning and/or a pointing system and for providing a compact system that does not require telecentric relays between adjacent acousto-optic deflectors.

35 Claims, 54 Drawing Sheets

U.S. PATENT DOCUMENTS

| | | | |
|---|---|---|---|
| 4,514,056 | A | 4/1985 | Azgapetian |
| H884 | H | 2/1991 | Gottlieb |
| 5,034,613 | A | 7/1991 | Denk et al. |
| 5,197,074 | A | 3/1993 | Emmons, Jr. et al. |
| 5,296,700 | A | 3/1994 | Kumagai |
| 5,365,239 | A * | 11/1994 | Stilwell, Jr. .................. 342/368 |
| 5,491,587 | A | 2/1996 | Iwaki et al. |
| 5,644,437 | A | 7/1997 | Maruyama et al. |
| 5,646,411 | A | 7/1997 | Kain |
| 5,680,252 | A | 10/1997 | Sitter, Jr. et al. |
| 5,825,497 | A | 10/1998 | Kim |
| 5,946,141 | A | 8/1999 | Harrigan |
| 6,166,385 | A | 12/2000 | Webb et al. |
| 6,285,507 | B1 | 9/2001 | Sakamoto |
| 6,307,665 | B1 | 10/2001 | Kim et al. |
| 6,344,653 | B1 | 2/2002 | Webb et al. |
| 6,473,233 | B1 | 10/2002 | Iizuka |
| 6,587,255 | B2 | 7/2003 | Davidson et al. |
| 6,906,824 | B1 | 6/2005 | Kamikubo et al. |
| 2002/0030890 | A1 | 3/2002 | Kato et al. |
| 2002/0057642 | A1 | 5/2002 | Kim et al. |
| 2002/0136524 | A1 | 9/2002 | Agha Riza |
| 2002/0149769 | A1 | 10/2002 | Roorda et al. |
| 2002/0149856 | A1 | 10/2002 | Chen et al. |
| 2003/0156323 | A1 | 8/2003 | Overbeck |
| 2005/0045814 | A1 | 3/2005 | Shimomura et al. |
| 2005/0061981 | A1 | 3/2005 | Allen et al. |
| 2005/0117221 | A1 | 6/2005 | Ogawa |
| 2005/0226557 | A1 | 10/2005 | Trutna et al. |
| 2005/0263690 | A1 | 12/2005 | Araya et al. |
| 2005/0279807 | A1 | 12/2005 | Johnson |
| 2006/0056062 | A1 | 3/2006 | Cheng |
| 2006/0071143 | A1 | 4/2006 | Saggau et al. |
| 2006/0087737 | A1 | 4/2006 | Choi et al. |

FOREIGN PATENT DOCUMENTS

| | | |
|---|---|---|
| EP | 0620468 | 10/1994 |
| EP | 0899603 | 3/1999 |
| EP | 1043615 | 10/2000 |
| EP | 1184855 | 3/2002 |
| EP | 1467235 | 10/2004 |
| EP | 1 587 185 A | 10/2005 |
| EP | 1587185 | 10/2005 |
| EP | 1596283 | 11/2005 |
| EP | 1862838 | 12/2007 |
| EP | 1870762 | 12/2007 |
| FR | 2708355 | 2/1995 |
| FR | 2708355 A | 2/1995 |
| GB | 2 119 109 A | 11/1983 |
| GB | 2119109 | 11/1983 |
| GB | 2368656 | 5/2002 |
| JP | 07-335526 A | 12/1995 |
| JP | 08-328050 A | 12/1996 |
| JP | 11-218682 A | 8/1999 |
| JP | 2004-535596 A | 11/2004 |
| WO | WO-02057811 | 7/2002 |
| WO | WO-03046613 | 6/2003 |
| WO | WO-2006042130 | 4/2006 |

OTHER PUBLICATIONS

Iyer, V et al: "Compensation of spatial and temporal dispersion for acousto-optic multiphoton laser-scanning microscopy," Journal of Biomedical Optics SPIE USA, vol. 8, No. 3, Jul. 2003, pp. 460-471, XP002471781, ISSN: 1083-3668.

International Search Report regarding International Application No. PCT/GB2009/000061 dated Apr. 20, 2009.

International Search Report regarding International Application No. PCT/GB2007/003455 dated Aug. 11, 2008.

Bewersdorf, J., Pick, R., and hell, S.W. (1998) Multifocal Multiphoton Microscopy. Optics Letters 23, 655-657.

Botcherby, E.J., Juskaitis, R., Booth, M.J., and Wilson, T. (2007). Aberration-Free Optical Refocusing in High Numerical Aperture Microscopy. Optics Letters 32 (14), 2007-2009.

Carter, A.G., and Sabatini, B.L. (2004). State-Dependent Calcium Signaling in Dendritic Spines of Striatal Medium Spiny Neurons. Neuron 44, 483-493.

Chaigneau, E., Oheim, M., Audinat, E., and Charpak, S. (2003). Two-Photon Imaging of Capillary Blood Flow in Olfactory Bulb Glomeruli. Proc Natl Acad Sci U S A 100, 13081-13086.

Cossart, R., Aronov, D., and Yuste, R. (2003). Attractor dynamics of network UP states in the neocortex. Nature 423, 283-288.

Denk, W., Piston, D.W., and Webb, W.W. (1995). Two photon molecular excitation in laser-scanning microscopy. In Handbook of Confocal microscopy, J.B. Pawley, ed. (Plenum), pp. 445-458.

Denk, W., Strickler, J.H., Webb, W. W. (1990). Two-Photon Laser Scanning Fluorescence Microscopy. Science, New Series, 248 (4951), 73-76.

Denk, W., and Svoboda, K. (1997). Photon upmanship: why multiphoton imaging is more than a gimmick. Neuron 18, 351-357.

DiGregorio, D.A. Nielsen, T.A., and Silver, R.A. (2004). Investigation of Synaptic Ampa Receptors with Glutamate Uncaging using a Diffraction-Limited UV Spot. Online Abstact Society for Neuroscience Program No. 404.4.

DiGregorio, D.A., Rothman, J.S., Nielsen, T.A., and Silver, R.A., (2007). Desensitization Properties of AMPA Receptors at the Cerebellar Mossy Fiber-Granule Cell Synapse Journal of neuroscience, 27(31), 8344-8357.

Fan, G.Y., Fujisaki, H., Miyawaki, A., Tsay, R.K., Tsien, R.Y., and Ellisman, M.H. (1990). Video-rate scanning two-photon excitation fluorescence microscopy and ratio imaging with cameleons. Biophys J 76, 2412-2420.

Gobel, W., Kampa, B.M. and Helmchen, F. (2007). Imaging cellular network dynamics in three dimensions using fast 3D laser scanning. Nature Methods 4 (1), 73-79.

Hopt, A., and Neher, E. (2001). Highly nonlinear photodamage in two-photon fluorescence microscopy. Biophys J 80, 2029-2036.

Iyer V, Hoogland TM, Saggau P (2006) Fast functional imaging of single neurons using random-access multiphoton (RAMP) microscopy. Journal of Neurophysiology 95:535-545.

Kaplan, A., Friedman, N., and Davidson, N. (2001). Acousto-Optic Lens with Very Fast Focus Scanning. Optics Letters 26, 1078-1080.

Kiskin, N. I., Chillingworth, R., McCray, J.A., Piston, D., and Ogden, D. (2002). The efficiency of two-photon photolysis of a "caged" fluorophore, o-1-(2-nitrophenyl) ethylpyranine, in relation to photodamage of synaptic terminals. Eur Biophys J 30, 588-604.

Kiskin, N.I. and Ogden, D. (2002. Two-photon excitation and photolysis by pulsed laser illumination modelled by spatially non-uniform reactions with simultaneous diffusion. Eur Biophys J 30, 571-587.

Koester, H.J., Baur, D., Uhl, R., and Hell, S.W. (1999). Ca2+fluorescence imaging with pico- and femtosecond two-photon excitation: signal and photodamage. Biophys J 77, 2226-2236.

Lechleiter, J.D., Lin, D.T., and Sieneart, I. (2002). Multi-photon laser scanning microscopy using an acoustic optical deflector. Biophys J 83, 2292-2299.

Margrie, T.W., Meyer, A.H., Caputi, A., Monyer, H., Hasan, M.T., Schaefer, A.T., Denk, W., and Brecht, M. (2003). Targeted whole-cell recordings in the mammalian brain in vivo. Neuron 39, 911-918.

Matsuzaki, M., Ellis-Davies, G.C., Nemoto, T., Miyashita, Y., Iino, M., and Kasai, H. (2001). Dendritic Spine Geometry is Critical for AMPA receptor expression in Hippocampal CA1 pyramidal neurons. Nat Neurosci 4, 1086-1092.

Ngoi, B.K.A., Venkatakrishnan, K., Tan, B., Stanley, P., and Lim, L.E.N. (2001). Angular dispersion compensation for acousto-optic devices used for ultrashort-pulsed laser micromachining. Optics Express 9, 200-206.

Oheim, M., Beaurepaire, E., Chaigneau, E., Mertz, J., and Charpak, S. (2001). Two-photon microscopy in brain tissue; parameters influencing the imaging depth. J. Neurosci Methods 111, 29-37.

Pawley, J.B. (1995). handbook of Biological Confocal Microscopy, Second edn (New York, Plenum Press).

Reddy D & Saggau P (2007) Fast Three-Dimensional Random Access Multi-Photon Microscopy for Functional Recording of Neuronal Activity, Proceedings of SPIE, vol. 6630 Confocal, Multiphoton, and nonlinear Microscopic Imaging III, Tony Wilson, Ammasi Periasamy, Editors, 66301A.

Reddy D & Saggau P (2007) Development of a random access multiphoton microscope for fast three-dimensional functional recording of neuronal activity, Proceedings of SPIE vol. 6443 Three- Dimensional and Multidimensional Microscopy: Image Acquisition and Processing XIV, Jose-Angel Conchello, Carol J. Cogswell, Tony Wilson, Editors, 64430U.

Roorda, R.D., Hohl, T.M., Toledo-Crow, R., and Miesenbock, G. (2004). Video-rate nonlinear microscopy of neuronal membrane dynamics with genetically encoded probes. J. Neurophysiol 92, 609-621.

Salome R, Kremer Y, Dieudonne S, Leger JF, Krichevsky O, Wyart C, Chatenay D, Bourdieu L. (2006) Ultrafast Random-Access Scanning in Two-Photon Microscopy Using Acousto-Optic Deflectors. Neurosci Methods. Jun. 30; 154 (1-2): 161-174.

Smith, M.A., Ellis-Davies, G.C., and Magee, J.C. (2003). Mechanism of the distance-dependent scaling of Schafer collateral synapses in rat CA1 pyramidal neurons. J Physiol 548, 245-258.

Stosiek, C., Garaschuk, O., Holthoff, K., and Konnerth, A. (2003). In vivo two-photon calcium imaging of neuronal networks. Proc Natl Acad Sci U S A 100, 7319-7324.

Young E H, Huey C H & Harrison L (1990) Optically Rotated long Time Aperture TeO2 Bragg cell. Proceedings of SPIE vol. 1296 Advances in Optical information processing IV, 304-315.

Zipfel, W.R., Williams, R.M., and Webb, W.W. (2003). Nonlinear magic: Multiphoton Microscopy in the Biosciences. Nat Biotechnol 21, 1369-1377.

Office Action regarding Japanese Patent Application No. 2009-527885 mailed Jun. 5, 2012. Translation provided by J.A. Kemp.

* cited by examiner

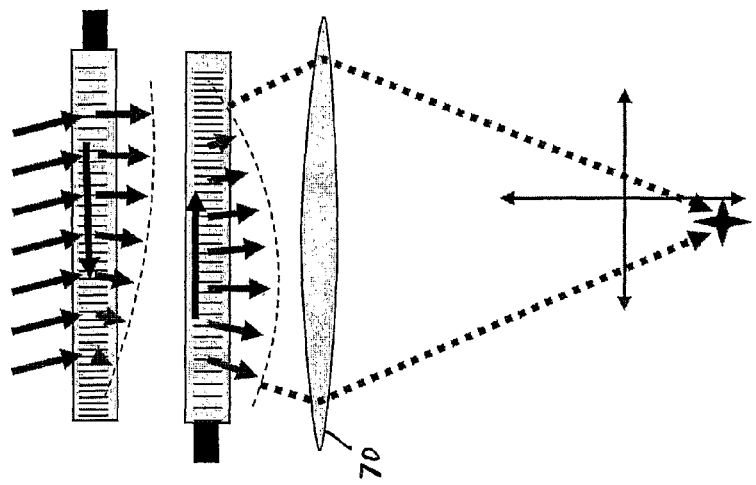
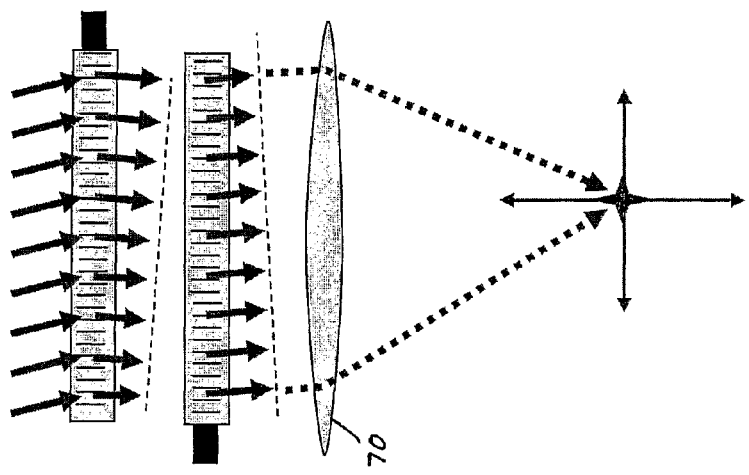
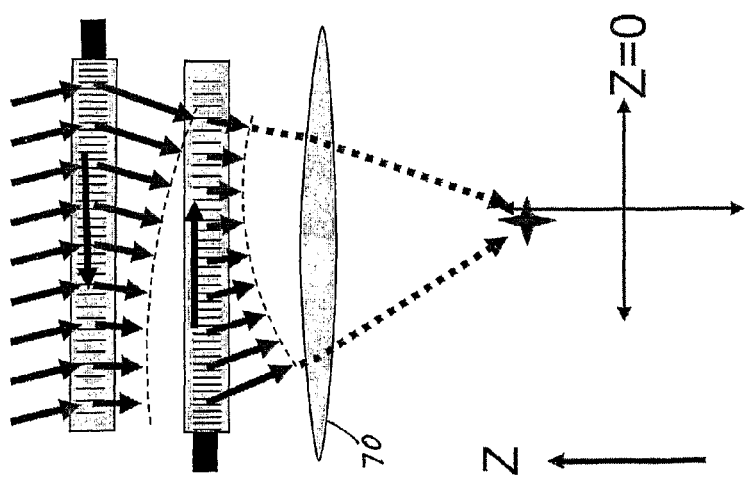

Fig. 11a.
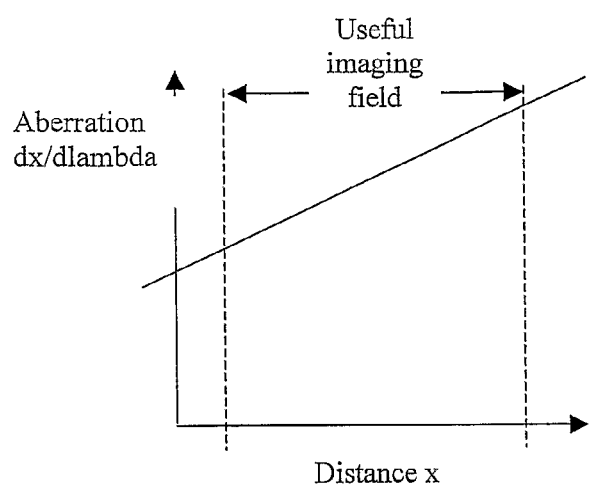
Fig. 11b.
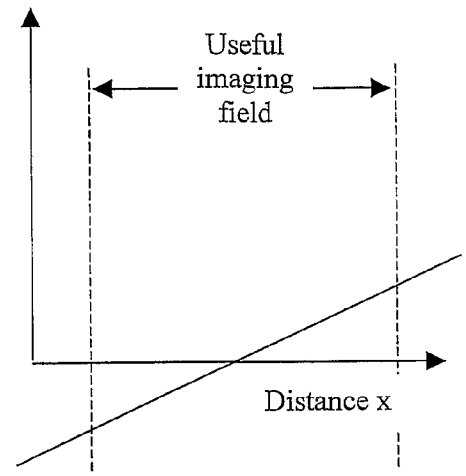
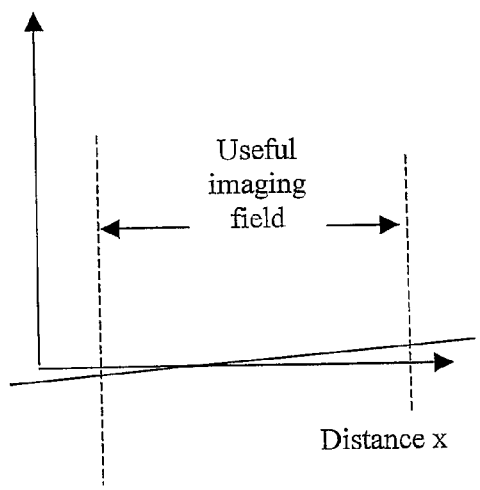
Fig.11c.

Fig. 28.
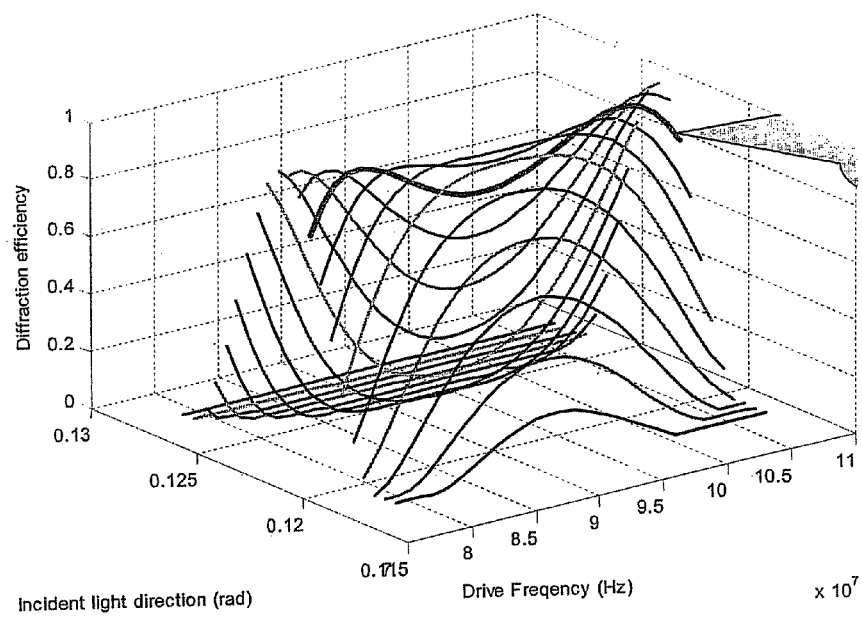
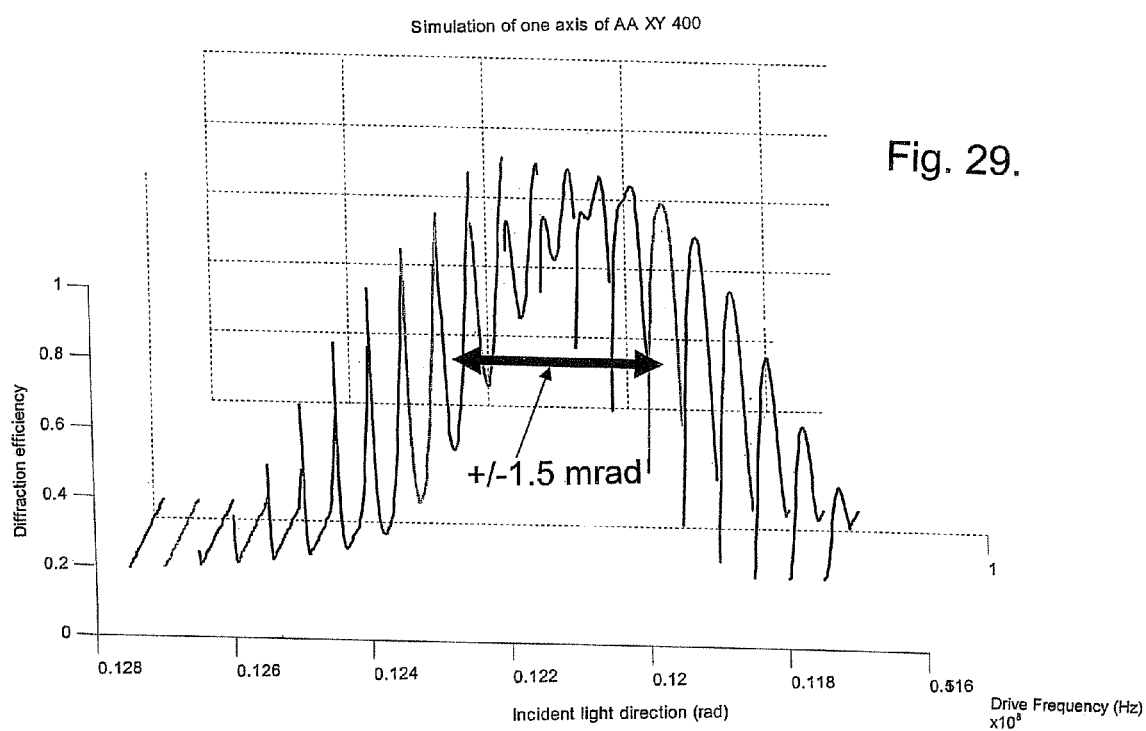
Fig. 29.

Fig. 40.
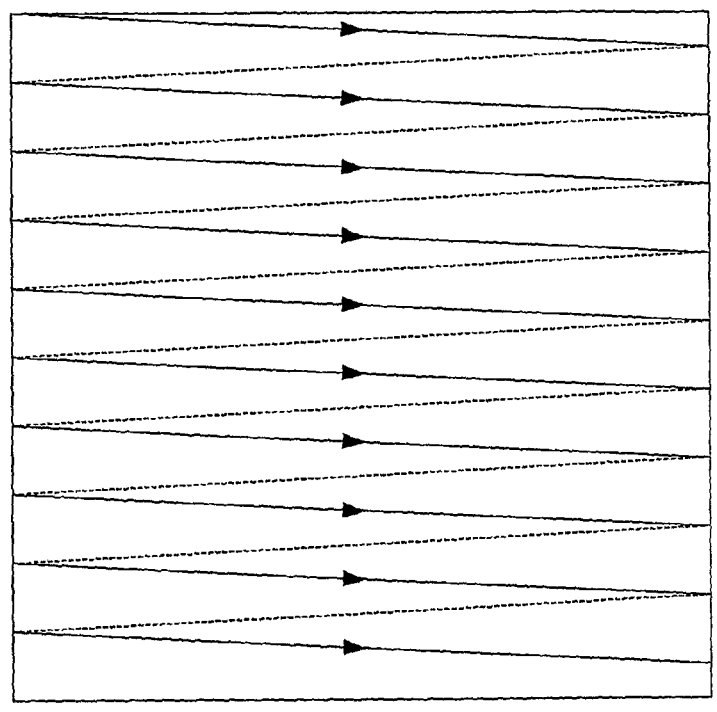
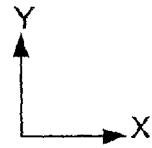

IMAGING APPARATUS AND METHODS

CROSS-REFERENCE TO RELATED APPLICATIONS

This application is a 371 U.S. National Stage of International Application No. PCT/GB2007/003455, filed 12 Sep. 2007, and published in English as WO 2008/032061 A2 on Mar. 20, 2008. This application claims the benefit of United Kingdom Patent Application No. GB 0617945.1, filed 12 Sep. 2006. The disclosures of the above applications are incorporated herein by reference.

The present invention relates to apparatus and methods involving the manipulation of a beam of electromagnetic radiation, such as a laser beam. More particularly, the invention relates to apparatus and methods which use a laser beam to image a target space, such as by selectively focussing the laser beam in the target space, which may be a 2D plane or a 3D volume. Several independent improvements to the state of the art are disclosed.

The ability to steer and focus electromagnetic radiation, such as a laser beam, rapidly in three-dimensions is very attractive for several applications in biology, microfabrication and data storage.

Laser scanning confocal imaging is an important and widely used tool in biology because it allows high contrast visualization of subcellular structures and monitoring of physiological processes with fluorescence indicators within living tissue by excluding contaminating of out-of focus light. Conventional confocal methods work best at relatively shallow depths where light penetration is good and scattering is minimal. Unfortunately, conventional confocal imaging cannot be used to image biological activity deep (>100 μm) within the living tissue. However, more recently, a new type of laser scanning confocal microscopy has been developed that relies on non-linear multiphoton excitation to selectively activate fluorophores where the light intensity exceeds the 2-photon threshold at the centre of the focal volume. Fluorescent light is emitted in all directions by these fluorophores and is picked up by a high numerical aperture lens system and photomultipliers. As the focal spot is scanned through the tissue the light intensity emitted by the fluorophores varies according to the intensity of staining by the fluorescence indicators in that part of the tissue. Combining the photomultiplier signal with the known position of the 2-photon focal volume enables a 2D or 3D image of the fluorescence intensity within the tissue to be reconstructed. This technique, known as two-photon microscopy, allows imaging at much greater depth because of the longer excitation wavelengths used for multiphoton excitation (wavelengths of 700-1000 nm), which scatter less than those used in conventional confocal imaging, and because confocality arises intrinsically from the excitation volume allowing all emitted photons to be used to construct the image. These properties together with the low levels of photodamage achievable have made 2-photon imaging an extremely powerful method for examining physiological processes at the cellular and subcellular levels both in vitro and in vivo.

Two-photon imaging has been particularly popular in neuroscience, as it has allowed the dynamic properties of neuronal network activity to be imaged in intact brain tissue using calcium indicators. The spatial resolution of 2-photon microscopy is well suited to this task even allowing the small synaptic connections between neurons to be resolved. Multiphoton excitation has also begun to be used to photolyse "caged compounds" that release neurotransmitters, allowing synaptic inputs onto a cell to be mimicked. This technique is potentially very important for understanding synaptic integration and thus determining how individual neurons carry out low-level computations.

Conventional laser scanning microscopes have traditionally used galvanometer mirrors to scan a laser beam. Such galvanometer mirrors are configured to scan in the X-Y plane only. Focussing in the Z direction is achieved by moving the apparatus relative to the sample (for example by moving the objective lens closer to or further away from the sample). The use of galvanometer mirrors has an inherent disadvantage in that the mirrors necessarily have a mass and the speed at which the mirror can be moved from one position to another is limited by inertia. In practical terms, this means that it takes of the order of 200-300 μs to move a mirror from one selected position to another selected position. In turn, this limits the number of spots upon which a laser beam can be focussed during a given time frame.

The temporal resolution of the present state of the art galvanometer-based two-photon imaging systems is one or two orders of magnitude too slow to accurately image signalling in a network of neurons. In such neurons, the elementary signal event (action potentials) occurs on the millisecond time scale. Moreover, the signals are spatially distributed in three-dimensions as they flow through the neural networks and building a 3-D stack of images using galvanometer-based technology takes minutes. Furthermore, galvanometers are too slow for studying synaptic integration in individual neurons using photolysis because the excitation beam needs to be moved to many (for example 30) sites within a millisecond in order to stimulate synapses distributed over the dendritic tree. For example, assuming that it takes 300 μs to move from one spot to another using a galvanometer mirror and assuming a dwell time at each spot of 5 μs, it would take 9.15 ms to image 30 sites. This is approximately 10 times too slow for current needs.

One approach suggested in the prior art to overcome some of the disadvantages is to use rapid acousto-optic deflectors (AODs) instead of galvanometers to steer the two-photon laser beam. The advantage of using AODs is that they allow the laser beam to be moved much more rapidly from point-to-point than in a galvanometer-based system (compare a movement time of 5-25 μs with AODs to 200-400 μs with galvanometers). This has several potential advantages. Firstly, images can be scanned rapidly. Secondly, multiple point measurements can be made with long dwell times at very high temporal resolution (e.g. using an AOD system with 15 μs movement time, 33 points can be simultaneously sampled at 1 KHz sample rate with a 15 μs dwell time or in other words 33 points can be monitored 1000 times per second). The use of AODs therefore allows more of the time to be devoted to collecting photons from the regions of interest rather than being taken up in moving the laser beam between sites.

As well as deflecting the laser beam in the X,Y plane, the use of two AODs per axis can, in principle, also be used to focus the laser beam in the Z dimension. For example, Kaplan et al describe in "Acousto-Optic Lens with Very Fast Focus Scanning" Optics Letters, Vol. 26, No. 14, Jul. 15, 2001, pp 1078-1080, the use of two or four AODs to focus a laser beam in the X and Z plane or anywhere in an X,Y and Z volume. To achieve focussing in a 3D volume, two AODs for focussing in the X-Z plane are followed by two AODs for focussing in the Y-Z plane.

One particular problem associated with multi-photon AOD scanning is spatial and temporal dispersion. Multi-photon applications typically require ultra-short laser pulses, for example of the order of 100 fs. However, the shorter the pulse, the larger the spread of wavelengths that exist in the pulse. The limiting example is an infinitely short pulse which has a completely flat frequency spectrum (i.e. a white spectrum). A pulse of 100 fs typically has a full-width, half-maximum spectral width of approximately 10 nm. The angle by which an AOD deflects a laser beam is related to the wavelength of the laser beam. Longer wavelengths are deflected more than shorter wavelengths. Thus, a form of spatial dispersion, also known as chromatic aberration, occurs when an ultra-short pulse is deflected by an AOD. When a laser pulse is diffracted through an AOD and then brought to a focus, the low frequency (long wavelength) parts of the pulse are focussed to a different position than the high frequency (short wavelength) parts of the pulse. This causes the pulse to be focussed to a line rather than a spot, the length of the line being related to the spectral width of the pulse. Further, different wavelengths of light travel at different speeds through the AOD which causes temporal dispersion, i.e. elongation of the pulse in time. These problems are described in "Compensation of Spatial and Temporal Dispersion for Acousto-Optic Multiphoton Laser-Scanning Microscopy" by Iyer et al, Journal of Biomedical Optics, 8(3), July 2003, pp 460-471.

These dispersion problems provide two system limitations—(i) they worsen the spatial resolution of the system, and (ii) they limit the excitation energy density that is achieved at the focus, thus reducing excitation efficiency.

Iyer et al propose the use of a diffraction grating matched to the central acoustic wavelength in order to relieve some of the spatial dispersion. However, this solution only corrects the chromatic aberration for a single spot in the image plane with the chromatic aberration steadily increasing as you move away from this spot in the image plane. This effect is known as magnification chromatic aberration because it can also be described by saying that the longer wavelength component of the image has greater spatial magnification than the shorter wavelength component.

Reddy & Saggau ("Fast Three-Dimensional Laser Scanning Scheme Using Acousto-Optic Deflectors", Journal of Biomedical Optics, 10(6), November/December 2005) and Salomé et al ("Ultrafast Random-Access Scanning in Two-Photon Microscopy using Acousto-Optic Deflectors", Journal of Neuroscience Methods, 154 (2006), pp 161-174) disclose a similar result in which two AODs are used to correct for chromatic aberration at one line in the image field but with chromatic aberration increasing as the deflection diverges from the compensation line. This is illustrated in FIG. 4c of Reddy & Saggau.

Thus, even with the best compensation systems disclosed in the prior art, chromatic aberration can be eliminated at one single point only in the field of view. The consequent focussing of a laser pulse to a line, rather than a diffraction limited spot, reduces the number of resolvable spots in the image plane. In a 3D image space, the effect of chromatic aberration can be quantified by considering the Number of Resolvable Detection Volumes (NRDV) in the image field. The detection volume of a 2-photon system is the volume of tissue or other excitable material that has sufficient intensity to be above its fluorescence activation threshold. As 2-photon processes are dependent on the square of optical intensity this volume is always smaller than the conventional focal volume of the point spread function of the focused laser beam. The prior compensation systems show increasing chromatic aberration as one moves away from the compensation point and thus the NRDV is much less than if the chromatic aberration were corrected for substantially the whole image space. Such prior compensation systems therefore do not give the desired spatial resolution to be used effectively for many applications, such as most 3D random access applications (e.g. neuroscience applications).

For such applications it is highly desirable to be able to randomly address any location in a volume of approximately 250×250×250 µm with a spatial resolution of 1×1×2 µm at a rate of 20-30 µs per point. This corresponds to a number of resolvable detection volumes (NRDV) of 7.8 million. Detailed modelling of the designs proposed to date has shown that the prior art methods struggle to achieve an NRDV in excess of 200,000. This is a factor of 40 below what is a desirable target for neuroscience applications.

Reddy & Saggau disclose coupling two adjacent AODs using telecentric relay optics (for example see FIG. 1c of their paper, supra). When four AODs are provided in a system capable of scanning a spot within a 3D volume, this necessitates at least three sets of telecentric relay optics. A typical length of a prior art telecentric relay, in the direction of the laser beam, is 400 mm. Thus, the requirement to utilise three telecentric relays adds 1.2 m to the length of the system in the path of the electromagnetic radiation. Accordingly, it is difficult to construct a device with a compact configuration and with minimal losses. It would be desirable to implement a shorter configuration, with less loss-introducing components, but maintaining the functionality of the AODs in focussing the laser beam.

When an AOD deflects a laser beam, it is the first order component that is usually of interest. The AOD will typically also pass an undeflected zeroth order component that can interfere with the signal. Kaplan et al solves this problem by ensuring that the two AODs deflect the laser beam in the same direction such that the undeflected zeroth order component does not reach the image field. An alternative configuration proposed by Reddy & Saggau of two parallel AODs suffers the potential problem that undeflected zeroth order components can reach the image field. Note that for the highest efficiency, the anisotropic crystals of the deflectors are used in the shear acoustic mode. These AODs have the property that the polarisation of the diffracted first order beam has its polarisation rotated through 90 degrees compared to the incoming laser beam and the zero order undeflected transmitted beam.

Another problem lies in the physical design of the AODs. Usually, the AOD devices are designed to have a good transmission efficiency (e.g. approximately 80%), but only for a very narrow range of input acceptance angles, (typically ±1.5 mrad). As the input acceptance angle varies, efficiency typically reduces. Thus, when two AODs are used in series, the second AOD will receive light at an angle defined by the deflection angle of the first AOD. Where the first AOD deflects the beam by a relatively large angle (e.g. greater than 1.5 mrad), this can cause the diffraction efficiency of the second AOD to be very low. It is therefore be desirable to design an AOD having higher efficiencies at a larger range of input acceptance angles.

There also exists a problem in that, for some applications, obtaining efficient transmission of the laser power is paramount, whereas for others, obtaining high spatial accuracy is paramount. For example, the use of a two-photon system for photolysis requires a much higher laser power than when used for imaging. Further, a reduced NRDV can be tolerated in photolysis applications. It would therefore be desirable to have a system in which the NRDV/power trade-off can be varied in accordance with the application to which the system is put.

It is convenient to be able to perform two-photon microscopy or photolysis at a selected wavelength. Typically, the useful wavelength range is 700 nm to 1000 nm. However, there is a problem in that diffractive optics inherently deflect by different amounts at different wavelengths (due to the fact that the diffraction angle increases as the wavelength increases). Providing a system that can operate under a range of different wavelengths is therefore difficult and would be desirable.

Furthermore, it would be desirable to provide a system that can provide selectable chromatic aberration correction. For example, it would be desirable to provide a system that can be configured easily to correct all the chromatic aberration in one X-Y plane. Such a system should preferably also be capable of being configured to correct all chromatic aberration in the Z plane. Preferably, such configuration should be via simple means such as moving lens systems, rather than by replacing components.

It is also desirable to provide a system that can operate in more than one mode. For example, a pointing mode in which a series of predetermined points can be visited sequentially is useful. Also, a scanning mode, in which the laser beam focus moves smoothly over the target is also useful. A system which can be easily switched between these modes is therefore very desirable.

It is furthermore desirable to provide a system which can perform scanning in a smooth fashion even though there are limits on the minimum and maximum frequencies that can be put through an acousto-optic deflector. These limits traditionally mean that scanning has to be stopped when the limit is reached. A system that can overcome this problem would be extremely desirable.

These and other problems are addressed by embodiments of the present invention.

In a first aspect, the present invention provides a system for selectively focussing a laser beam, said system comprising: diffractive optics for focussing the laser beam in an image field, said diffractive optics being such that, when said laser beam has spectral width, said diffractive optics will cause, in use, magnification chromatic aberration in said image field; and at least one optical element for at least partially correcting said magnification chromatic aberration, which at least one optical element is arranged to modify said image field such that the longer wavelength components are magnified less than the shorter wavelength components.

The diffractive optics for deflecting and/or focussing the laser beam are preferably one or more acousto-optic deflectors.

The spectral width of the laser beam (for example 10 nm for a 100 fs pulsed laser beam) causes chromatic aberration in the image field. Further there are different amounts of chromatic aberration at different positions in the image field. In the usual case, there is one point in the image field, known as the compensation point, where chromatic aberration is at a minimum. The chromatic aberration generally increases at positions away from this compensation point in the image field. If one takes a slice through the image field intersecting the compensation point, a graph of the chromatic aberration would cross the zero line at the compensation point as the aberration changed from negative to positive (or vice versa) and would thus increase in magnitude either side of the compensation point, usually in a straight line. The gradient of this line is known as the magnification chromatic aberration and the first aspect of the invention diminishes the magnification chromatic aberration by reducing the gradient of this line. Thus, the magnitude of the chromatic aberration existing at every point in the image field is reduced (except at the compensation point where the magnitude is already zero).

The system preferably comprises a laser for supplying the laser beam, which laser is preferably a pulsed laser having laser pulses of 2 ps or less, preferably 500 fs or less, more preferably still about 100 fs.

The centre frequency of the laser beam is typically in the range 600 to 1000 nm, preferably 700 to 900 nm, more preferably 800 to 875 nm, and more preferably still approximately 850 nm.

The correction can be carried out in a 2D image plane in which case it is possible to use either a modified microscope objective lens as the optical element for correcting the magnification chromatic aberration or an additional dispersive lens prior to the objective, for instance at the usual tube lens position or at some similar position earlier in the optical relay chain.

In one embodiment, a telecentric relay is used to provide the necessary correction. Preferably, the telecentric relay has first and second lenses and the rates of change of focal length with wavelength for the first and second lenses are of opposite sign. It is preferable that the rates of change of focal length with wavelength for the first and second lenses are of substantially the same magnitude. Preferably, the first lens (i.e. the one the laser beam encounters first) has a shorter focal length for longer wavelengths than for shorter wavelengths and the second lens has a longer focal length for longer wavelengths than for shorter wavelengths. This means that the longer wavelengths are magnified less by the telecentric relay and this provides the necessary correction to the magnification chromatic aberration.

The first and/or second lenses are preferably dispersive lenses and can be made from combinations of crown glass, flint glass and diffractive optical elements.

The use of a telecentric relay allows the magnification chromatic aberration to be at least partially corrected for all points in a 3D image field and not just in a 2D plane.

In one preferable embodiment, a compensation factor C can be defined, a value of C=1 providing perfect compensation for all of the chromatic aberration in the Z-direction, a value of C=2 providing perfect compensation for all of the chromatic aberration in the X and Y directions, and wherein C is selected to be less than 2.

Preferably, C is selected to be around 1.3.

In connection with the first aspect of the invention, there is also provided a method for at least partially correcting magnification chromatic aberration introduced into a laser beam by diffractive optics, said method comprising: passing said laser beam through at least one optical element so as to at least partially correct the magnification chromatic aberration.

The diffractive optics can be one or more AODs or any alternative dynamically controlled system for deflecting and focussing a laser beam. Such alternative dynamic diffractive systems might for example be based on liquid crystal holographic optical elements, magneto-optic arrays, digital micromirror arrays or any other spatial light modulator device.

In connection with the first aspect of the invention, there is also provided a magnification chromatic aberration correcting telecentric relay comprising: a first lens; second lens; wherein the rates of change of focal length with wavelength for the first and second lenses are of opposite sign in the wavelength range of interest.

Preferably, the rates of change of focal length of wavelengths for the first and second lenses are of substantially the same magnitude. Also, the first and second lenses can be separated by a distance approximately equal to the sum of their focal length for all wavelengths in the wavelength range of interest.

The lenses can be made of combinations of crown and flint glass. More preferably, the lenses comprise diffractive elements attached to conventional lenses.

A second aspect of the invention provides apparatus for selectively deflecting a laser beam, said apparatus comprising: a first acousto-optic deflector that is arranged to modulate a laser beam into at least (i) a zeroth order component of identical polarisation to the input laser beam and (ii) a first order component having a polarisation rotated by 90° compared to the input laser beam; a first half-wave plate that is arranged to rotate the polarisation of the output of said first acousto-optic deflector by 90°; a first polariser that is arranged to pass said polarisation-rotated first order component and to block said polarisation-rotated zeroth order component;

a second acousto-optic deflector that is arranged to modulate said passed first order component to produce at least (i) a second zeroth order component of identical polarisation to said passed first order component and (ii) a second first order component of polarisation rotated by 90° compared to said passed first order component; a second polariser that is arranged to pass said second first order component and to block said second zeroth order component.

The use of the half-wave plate and two polarisers allows the undesirable zeroth order components to be blocked effectively without substantially reducing the power of the desirable first order components.

The first and second acousto-optic deflectors can be used to deflect and focus the laser beam in the X-Z plane. Additional third and fourth acousto-optic deflectors may be provided to provide additional focussing in the Y-Z plane. An additional half-wave plate and a further two polarisers can be used to block the zeroth order components that may be created in the third and fourth acousto-optic deflectors.

This construction allows the wanted output beam (that is the first order diffracted beam from each AOD) to be diffracted first in one direction, then in the opposite direction by the counter propagating acoustic wave in the second crystal of each pair. Thus the final net beam deflection at the centre of the image field is zero. This makes the arrangement naturally self compensating for chromatic dispersion at the centre of the image field. The use of the polarisers has eliminated the potentially interfering zero order undeflected beams from each AOD.

In connection with the second aspect, there is also provided apparatus for selectively deflecting a laser beam, said apparatus comprising: a first acousto-optic deflector; a second acousto-optic deflector; a first polariser; and a second polariser.

The first polariser is preferably located between the first and second acousto-optic deflectors. This allows it to cut out the unwanted zero diffraction order and transmit the useful first diffraction order.

The first and second acousto-optic deflectors are conveniently arranged to deflect and focus a laser beam in a first plane, such as in the X-Z plane, and the first and second polarisers are conveniently arranged to pass only the first order components of diffraction (and block the zeroth order components of diffraction).

The first polariser preferably follows the first acousto-optic deflector and the second polariser preferably follows the second acousto-optic deflector.

To achieve additional deflection and focussing in the Y-Z plane, third and fourth acousto-optic deflectors can be provided together with third and fourth polarisers.

A particularly preferred configuration arranges the acousto-optic deflectors in the order first, third, second, fourth. This dispenses with the need for half-wave plates. Alternatively, the acousto-optic deflectors can be arranged in the order first, second, third, fourth and two half-wave plates can be arranged between the first and second and the third and fourth acousto-optic deflectors respectively.

In accordance with the second aspect, there is also provided a method for selectively deflecting a laser beam, said method comprising: using first and second acousto-optic deflectors to focus a laser beam in a first plane; and using first and second polarisers to pass the first order components of diffraction and to block any zeroth order components of diffraction.

Third and fourth acousto-optic deflectors are preferably used to focus the laser beam in the second plane and third and fourth polarisers are preferably used to pass the first order components of diffraction and block any zeroth order components of diffraction.

The polariser of the laser beam is preferably rotated by 90° subsequent to the laser beam exiting the first and third deflectors but prior to the laser beam entering the second and fourth polarisers respectively.

In accordance with a third aspect of the invention, there is provided apparatus for deflecting a laser beam, said apparatus comprising: a first acousto-optic deflector optimised for efficient transmission at the input laser beam angle; and a second acousto-optic deflector of lower peak efficiency than the first acousto-optic deflector but which accepts laser beams from a wider range of angles at better transmission efficiency than said first acousto-optic deflector.

This aspect of the invention addresses the problem that, in the prior art, the range of angles at which a laser beam could enter the second acousto-optic deflector of each X-Z or Y-Z pair is large which means that transmission efficiency is very poor at some input angles. In accordance with this aspect of the invention, the second acousto-optic deflector is designed so as to have an efficiency versus input angle curve having a flatter and broader peak than the first acousto-optic deflector. Thus, although efficiency is reduced at the optimum input angle, efficiency is increased at variations from the optimum angle such as to provide acceptable transmission throughout the whole range of possible input angles. To maintain sufficient output power from the system for 2-photon imaging great care needs to be taken to minimise other system losses. The loss of power can also be compensated by increasing the power of the source laser.

There thus exists an optimum designed acceptance angle for the second of each pair of AODs (i.e. the second and fourth AODs). As their acceptance angle increases so the NRDV increases as the scannable volume increases, but suddenly if the acceptance angle is increased beyond the optimum, the diffraction efficiency drops too low and the intensity of the laser spot reduces below the threshold required for 2-photon fluorescence and the NRDV drops rapidly (note the NRDV only counts detection volumes where the laser intensity is above the two-photon threshold). Examples of such optimisation curves can be seen in FIGS. 23 and 24.

The third aspect of the invention also provides a method of deflecting a laser beam, said method comprising: passing a beam through a first acousto-optic deflector that has been optimised for efficient transmission at the input laser beam angle; deflecting said beam using said first acousto-optic deflector; passing said deflected beam through a second acousto-optic deflector that has a lower peak efficiency than said first acousto-optic deflector but which accepts laser beams from a wider range of angles at better transmission efficiency that said first acousto-optic deflector; and deflecting said beam using said second acousto-optic deflector.

In a fourth aspect of the invention, there is provided apparatus for deflecting a laser beam, said apparatus comprising: first and second acousto-optic deflectors for focusing a laser beam in a first direction; and third and fourth acousto-optic deflectors for focusing a laser beam in a second direction; wherein said acousto-optic deflectors are arranged in this order along the path of the laser beam: first, third, second, fourth.

This particular order of acousto-optic deflectors dispenses with the need for half-wave plates to rotate the polarisation of the light. This first acousto-optic deflector will transmit a first order component of diffraction that is rotated by 90° compared to the input laser beam. The third acousto-optic deflector is well-suited for receiving this first order component of diffraction and will transmit a further first order component that is rotated by a further 90°. The second acousto-optic deflector is well-suited for receiving this laser beam and will again rotate the polarisation by a further 90°, making it suitable for reception by the fourth acousto-optic deflector. The inherent polarisation rotation introduced to the first order components of diffraction by the AODs are, when this order of AODs is used, compatible with the polarisation acceptance of the next AOD in the sequence.

In accordance with the fourth aspect, there is also provided a method of deflecting a laser beam, said method comprising: using first and second acousto-optic deflectors to focus a laser beam in a first direction; and using second and third acousto-optic deflectors to focus a laser beam in a second direction; wherein said acousto-optic deflectors are arranged in this order along the path of the laser beam: first, third, second fourth.

A fifth aspect of the invention provides an acousto-optic deflector comprising: a crystal for propagating an acoustic wave that will diffract an input laser beam; a first crystal transducer for supplying acoustic vibrations to the crystal; and a second crystal transducer for supplying acoustic vibrations to the crystal; wherein said first and second crystal transducers are located on the same side of the crystal.

The first crystal transducer is preferably arranged to create a more diverging acoustic wave in the crystal than said second crystal transducer.

The effect of the more diverging acoustic wave is preferably to allow the efficient diffraction of laser beams coming from a wider range of angles.

A more diverging acoustic wave can be created by adjusting the width of the first crystal transducer to be smaller in the direction parallel to the direction of light propagation. For example, a crystal transducer width of less than 1 mm can create an appropriate diverging acoustic wave.

The second crystal transducer is preferably wider in the direction of light propagation than the first crystal transducer. This allows the first crystal transducer to be one which supplies a more diverging acoustic wave and the second crystal transducer to be one which supplies a less diverging acoustic wave. The two transducers therefore are preferably designed to create acoustic waves having different properties giving added flexibility to the system.

Preferably, each crystal transducer can be independently selectable such that one or both may be excited to modulate the divergence of the acoustic wave in the crystal.

There can be provided any number of crystals, such as one, two, three, four or more.

A switch mechanism can be provided to selectively allow for only one transducer to be excited, two transducers to be excited together or three transducers to be excited together. The transducers are preferably adjacent to one another.

In a preferred embodiment, the width of each transducer increases in a geometric progression in a direction parallel to the direction of light propagation.

In accordance with a sixth aspect of the invention, and a selection switch is provided to allow either the first or second crystal transducer to be excited. In more particularity, the sixth aspect of the invention provides an acousto-optic deflector comprising: a crystal for propagating an acoustic wave that will diffract an input laser beam; a first crystal transducer for supplying acoustic vibrations to the crystal; a second crystal transducer for supplying acoustic vibrations to the crystal; and a selection switch for selecting whether the first or second crystal transducer is excited.

The sixth aspect of the invention provides a method of deflecting a laser beam, said method comprising: selecting one of a first or second crystal transducer arranged to supply acoustic vibrations to a crystal; exciting said selected crystal transducer so as to propagate an acoustic wave in said crystal; and diffracting said laser beam with said acoustic wave.

In accordance with a seventh aspect of the invention, the crystal of the acousto-optic deflector has a particular orientation. More specifically, the seventh aspect of the invention provides an acousto-optic deflector comprising: a crystal having a laser input direction defined by the negative Z-axis; wherein said crystal structure is rotated by approximately 2° about the X-axis and approximately 3° about the Y-axis.

Also in accordance with the seventh aspect of the invention, there is provided an acousto-optic deflector comprising: a crystal oriented such that acoustic waves propagating therethrough will have approximately 20° between their wave vector and their Poynting vector.

Preferably, the second of a pair of acousto-optic deflectors has a construction in accordance with the second aspect of the invention. In such a case, it is useful that the first deflector in the pair also has the same construction.

According to an eighth aspect of the invention, there are provided systems and methods which can account for a non-zero effective optical separation between adjacent AODs.

This can preferably be achieved by providing a system for manipulating a beam of electromagnetic radiation, said system comprising: a first acousto-optic deflector; a second acousto-optic deflector positioned downstream of said first acousto-optic deflector and being separated from said first acousto-optic deflector by an effective optical separation; a driver for providing acoustic waves in said first and second acousto-optic deflectors, said acoustic waves being chirped at different ramp rates to account for said effective optical separation between said first and second acousto-optic deflectors.

Preferably, the driver is arranged to provide acoustic waves that cause the electromagnetic radiation to be focused to a stationary line in space.

Preferably, there is provided a system wherein said driver provides an acoustic wave with a ramp rate $a_1$ to said first acousto-optic deflector and provides an acoustic wave with a ramp rate $a_2$ to said second acousto-optic deflector, and wherein said ramp rates are related by:

$$\frac{a_1}{a_2} = \frac{2d_2'}{2d_2' = d_1}$$

where $d_1$ is the effective optical separation between said first and second acousto-optic deflectors and $d_2'$ is the effective optical distance to the focal line from the second acousto-optic deflector.

In preferred embodiments, the system further comprises a third acousto-optic deflector; a fourth acousto-optic deflector positioned downstream of said third acousto-optic deflector and being separated from said third acousto-optic deflector by an effective optical separation; wherein said driver is arranged to provide acoustic waves in said third and fourth acousto-optic deflectors, said acoustic waves being chirped at different ramp rates to account for said effective optical separation between said third and fourth acousto-optic deflectors.

The driver is preferably arranged to select frequencies of the acoustic waves that scan a target in the X and/or Y direction.

The driver is preferably arranged to select frequencies for said first and second acousto-optic deflectors such as to achieve an angular scan rate of $\delta\theta/\delta t$ by adjusting the ramp rate $a_1$ of the first acousto-optic deflector to be:

$$a_1 = \frac{\frac{V}{\lambda}\left(\frac{V}{2d_2'} - \frac{\delta\theta}{\delta t}\right)}{2 + \frac{d_1}{d_2'} - \frac{d_1}{V}\frac{\delta\theta}{\delta t}}$$

and by adjusting the ramp rate $a_2$ of the second acousto-optic deflector to be:

$$a_2 = \frac{V^2}{2\lambda d_2'} + \frac{V}{2\lambda}\frac{\delta\theta}{\delta t}$$

where V is the speed of sound in the first and second acousto-optic deflectors, $\lambda$ is the wavelength of the laser beam to be deflected, $d_2'$ is the distance to the focal line/point from the second acousto-optic deflector and $d_1$ is the effective optical separation between said first and second acousto-optic deflectors.

The driver preferably provides acoustic waves such as to scan a target in the Z and/or Y direction, said scan being composed of a series of mini-scans, with a non-active scan period between each active scan time of each mini-scan.

This non-active period can be used to adjust the value of the frequencies without moving the focus position and preferably consists of a frequency resetting time and a AOD fill time.

The non-active time starts at the end of the active scan time of one mini-scan and ends at the beginning of the active scan time of the subsequent mini-scan.

The active scan time is preferably that time for which measurements are taken and, generally, measurements are not taken during the non-active time duration. Also included in the eighth aspect of the invention is a method of manipulating a beam of electromagnetic radiation, said method comprising passing said electromagnetic radiation through a first acousto-optic deflector and a second acousto-optic deflector downstream of said first acousto-optic deflector, the deflectors containing first and second acoustic waves respectively; wherein said first and second acoustic waves are chirped at different ramp rates to account for the effective optical separation between said first and second acousto-optic deflectors.

In accordance with the ninth aspect of the invention, there is provided a method of scanning a target volume with a beam of electromagnetic radiation, said method comprising passing said electromagnetic radiation through a first acousto-optic deflector and a second acousto-optic deflector downstream of said first acousto-optic deflector, the deflectors containing first and second acoustic waves respectively so as to move a focus position of said beam along a scan path in said target volume; wherein said first and second acoustic waves are chirped to have a constantly increasing or decreasing frequency; and when one of said acoustic waves is at a predetermined maximum or minimum frequency value, offsetting the frequency of each acoustic wave such that the acoustic waves may continue to be chirped while having frequencies lower than said predetermined maximum frequency and higher than said predetermined minimum frequency.

The frequency offsetting can be carried out whether or not the acousto-optic deflectors are telecentrically coupled or there is a real optical separation between the deflectors. Preferably, said first and second acousto-optic deflectors are separated by an effective optical separation $d_1$ and said focal position is an effective optical distance $d_2'$ from said second acousto-optic deflector, said offsets satisfying:

$$\frac{\Delta f_1}{\Delta f_2} = \frac{2d_2'}{2d_2' + d_1}$$

where $\Delta f_1$ is the frequency offset for the first acoustic wave and $\Delta f_2$ is the frequency offset for the second acoustic wave.

Preferably, the target volume is scanned as a series of mini-scans, the active scan time of each mini-scan terminating approximately at the point where the frequency of each acoustic wave is offset and the active scan time of subsequent mini-scans beginning after a non-active period from said termination point of the previous mini-scan.

Also in accordance with the ninth aspect of the invention there is provided a system for scanning a target volume, said system comprising a first acousto-optic deflector; a second acousto-optic deflector positioned downstream of said first acousto-optic deflector; a driver for providing acoustic waves in said first and second acousto-optic deflectors; wherein said driver is arranged to offset the frequency of each acoustic wave when one of said acoustic waves reaches a predetermined maximum or minimum frequency value so as to maintain a predetermined chirp rate for said acoustic weaves while keeping the absolute frequency value for said first and second acoustic waves between said predetermined minimum and maximum frequency values.

In accordance with the tenth aspect of the invention, there is provided a system for selectively focussing a beam of electromagnetic radiation, said system comprising diffractive optics for focussing the beam in an image field, said diffractive optics causing chromatic aberration in said image field; corrective optics for at least partially correcting said chromatic aberration, said corrective optics being adjustable such that said chromatic aberration can be at least partially corrected when the electromagnetic radiation has a wavelength falling within a range of wavelengths of interest.

Preferably, the corrective optics is capable of ensuring that the beam of electromagnetic radiation fills the same design system aperture for substantially all wavelengths falling within the range of the wavelength of interest. For example, the radiation can be made to fill the aperture of the system objective lens to provide the maximum focussing resolution.

The corrective optics preferably comprises first and second diffractive correction plates.

These correction plates may also be comprised of conventional lenses.

Preferably, the first correction plate has a first diffractive element having positive power attached to a negative focal length real lens and the second correction plate has a second diffractive element having negative power, attached to a positive focal length real lens. The attachment is preferably intimate, for example by optical gluing.

The diffractive optical element and real lens in each correction plate is preferably balanced such that at a predetermined wavelength in the mid-operating range (for example 800-850 nm), both correction plates are of close to zero effective power.

Further lenses can be placed either side of the correction plate.

These further lenses can be implemented by a pair of zoom lenses.

In accordance with the tenth aspect, there is provided a method of selectively focussing a beam of electromagnetic radiation, said method comprising passing said beam of electromagnetic radiation through diffractive optics to focus the beam in an image field, said diffractive optics causing chromatic aberration in said image field; adjusting corrective optics when the wavelength of said electromagnetic radiation is changed within a range of wavelengths of interest; passing said electromagnetic radiation through said adjusted corrective optics to at least partially correct said chromatic aberration.

In accordance with an eleventh aspect of the invention, there is provided a system for selectively focussing a beam of electromagnetic radiation, said system comprising diffractive optics for focussing the beam in an image field, said diffractive optics causing chromatic aberration in said image field; corrective optics for at least partially correcting said chromatic aberration, said corrective optics being capable of substantially fully correcting chromatic aberration in an X-Y plane when a compensation factor C is equal to 2 and being capable of substantially fully correcting chromatic aberration in a Z plane when said compensation factor C is equal to 1, said compensation factor being user selectable.

The compensation factor C is preferably set by moving diffractive elements.

The system is preferably arranged to receive from a user a desired compensation factor and a desired electromagnetic radiation wavelength.

Preferably, upon receiving such input, the system moves elements of the corrective optics so as to provide a chromatic aberration correction in accordance with the compensation factor at the desired wavelength.

In accordance with the eleventh aspect, there is provided a method of selectively focussing a beam of electromagnetic radiation, said method comprising passing said electromagnetic radiation through diffractive optics, said diffractive optics causing chromatic aberration in an image field; selecting a compensation factor C; configuring corrective optics in accordance with said selected compensation factor C; passing said electromagnetic radiation through said corrective optics to at least partially correct said chromatic aberration, wherein said corrective optics are capable of substantially fully correcting chromatic aberration in an X-Y plane when said compensation factor C is equal to 2 and are capable of substantially fully correcting chromatic aberration in a Z plane when said compensation factor C is equal to 1.

In accordance with the twelfth aspect of the invention, there is provided a system for manipulating a beam of electromagnetic radiation, said apparatus comprising a first acousto-optic deflector; a second acousto-optic deflector; a driver for providing first and second acoustic waves to said first and second acousto-optic deflectors respectively; a user operated switch for selecting between a random access mode and a scanning mode.

Preferably, when said random access mode is selected, a series of points in a target volume can be programmed into the system and the acousto-optic deflectors are thereafter used to focus a beam of electromagnetic radiation to each of said plurality of points in the target volume for a predetermined dwell time.

Preferably, when the scan mode is selected the system is arranged to scan a focal position along a predetermined path using said acousto-optic deflectors.

Preferably, the scan is made up of a plurality mini-scans having a duration determined in part by the Z-position at which scanning takes place.

Preferably, the apparatus is configured to perform the following method: scanning a target in three dimensions; presenting to a user images of the target; receiving inputs from the user identifying a plurality of points within the target; calculating the signals to provide to said driver for causing the beam of electromagnetic radiation to sequentially point to said selected plurality of points in the target; and pointing the beam of electromagnetic radiation sequentially to said selected points.

This aspect of the invention also provides a method of manipulating a beam of electromagnetic radiation, said method comprising determining a selection from a user; passing said beam of electromagnetic radiation through first and second acousto-optic deflectors, said first and second acousto-optic deflectors respectively containing first and second acoustic waves; wherein when a user has selected a random access mode, said waves are configured to cause said beam of electromagnetic radiation to sequentially point to a series of points within a three-dimensional volume for a predetermined respective dwell time; and when said user has selected a scanning mode, said waves are configured to cause said beam of electromagnetic radiation to scan a path in said three-dimensional volume at a predetermined scan rate.

In addition, this aspect can provide a method of manipulating a beam of electromagnetic radiation, said method comprising: scanning a beam of electromagnetic radiation around a path in a three-dimensional volume so as to provide an image of said volume; receiving an identification of a plurality of points within said target volume from a user; sequentially pointing said beam of electromagnetic radiation to said plurality of identified points.

In accordance with a thirteenth aspect of the invention, there is provided a method of scanning a target volume with a beam of electromagnetic radiation, said method comprising passing said electromagnetic radiation through a first acousto-optic deflector and a second acousto-optic deflector downstream of said first acousto-optic deflector, the deflectors containing first and second acoustic waves respectively so as to move a focus position of said beam along a scan path in said target volume at an angular scan rate given by $\delta\theta/\delta t$; wherein said first and second acoustic waves are chirped to have a constantly increasing or decreasing frequency; and wherein the ramp rates of said chirped acoustic waves are selected in accordance with:

$$a_1 = \frac{\frac{V}{\lambda}\left(\frac{V}{d_2'} - \frac{\delta\theta}{\delta t}\right)}{2 + \frac{d_1}{d_2'} - \frac{d_1}{V}\frac{\delta\theta}{\delta t}}$$

$$a_2 = \frac{V^2}{2\lambda d_2'} + \frac{V}{2\lambda}\frac{\delta\theta}{\delta t}$$

where $a_1$ is the ramp rate in the first acousto-optic deflector, $a_2$ is the ramp rate in the second acousto-optic deflector, V is the speed of sound in the first and second acousto-optic deflectors, $\lambda$ is the wavelength of the electromagnetic radiation beam, $d_1$ is the effective optical separation between the first and second acousto-optic deflectors and $d_2'$ is the distance to the focus position from the second acousto-optic deflector.

The value $d_1$ can be made zero, in which case the acousto-optic deflectors can be coupled together by a telecentric relay.

Alternatively, the value of $d_1$ can be made non-zero and the values of the chirp rates can be found in accordance with the above equations (taking into account the small corrections to these equations that may be needed to account for small errors in the alignment of components).

Preferably, the ramp rate $a_2$ of the acoustic wave in the second acousto-optic deflector is determined such that the additional curvature provided to the wavefront of said electromagnetic radiation by said second acousto-optic deflector is a predetermined amount more or less than the curvature of the wavefront as it arrives at said second acousto-optic deflector from said first acousto-optic deflector, such as to provide for the scanning of said focal position.

In accordance with this aspect there is provided a system for scanning a target volume with a beam of electromagnetic radiation, said system comprising: a first acousto-optic deflector; a second acousto-optic deflector positioned downstream of said first acousto-optic deflector and being separated from said first acousto-optic deflector by an effective optical separation; a driver for providing respective first and second acoustic waves in said first and second acousto-optic deflectors, said first acoustic wave having a ramp rate given by;

$$a_1 = \frac{\frac{V}{\lambda}\left(\frac{V}{d_2'} - \frac{\delta\theta}{\delta t}\right)}{2 + \frac{d_1}{d_2'} - \frac{d_1}{V}\frac{\delta\theta}{\delta t}}$$

and said second acoustic wave having a ramp rate given by:

$$a_2 = \frac{V^2}{2\lambda d_2'} + \frac{V}{2\lambda}\frac{\delta\theta}{\delta t}$$

where $a_1$ is the ramp rate in the first acousto-optic deflector, $a_2$ is the ramp rate in the second acousto-optic deflector, V is the speed of sound in the first and second acousto-optic deflectors, $\lambda$ is the wavelength of the electromagnetic radiation beam, $d_1$ is the effective optical separation between the first and second acousto-optic deflectors and $d_2'$ is the distance to the focus position from the second acousto-optic deflector.

In any of the aspects of the present invention, the following are preferable features.

The electromagnetic radiation is selectively focussed to a line and/or to a point.

The electromagnetic radiation passes through a system comprising microscope optics, for example a system including a microscope objective lens.

The method, apparatus and system of the present invention is particularly useful for implementing non-linear optical processes, such as multi-photon processes or two-photon processes.

In all embodiments, chromatic aberration is preferably substantially corrected over a 3D image field.

Any of the acousto-optic deflectors of the present invention are preferably made from a higher frequency anisotropic acousto-optic crystal of which $TeO_2$ is one example.

The present invention will now be further described, by way of non-limitative example only, with reference to the accompanying schematic drawings, in which:

FIGS. 7a-7c show how a lens 70 can be used to focus the AOD output to a real position in a target;

FIGS. 11a, 11b and 11c show graphs of the chromatic aberration versus the distance X in the image field. FIG. 11a shows the completely uncorrected graph, FIG. 11b shows a graph corrected at a single point in the image field and FIG. 11c shows a graph in which magnification chromatic aberration has also been corrected;

FIG. 28 is a three-dimensional plot of the diffraction efficiency of a known AOD;

FIG. 29 is the same as FIG. 28, but viewed from a different direction;

FIG. 40 shows a scan pattern in the X-Y plane;

TECHNICAL BACKGROUND

Figure 1:
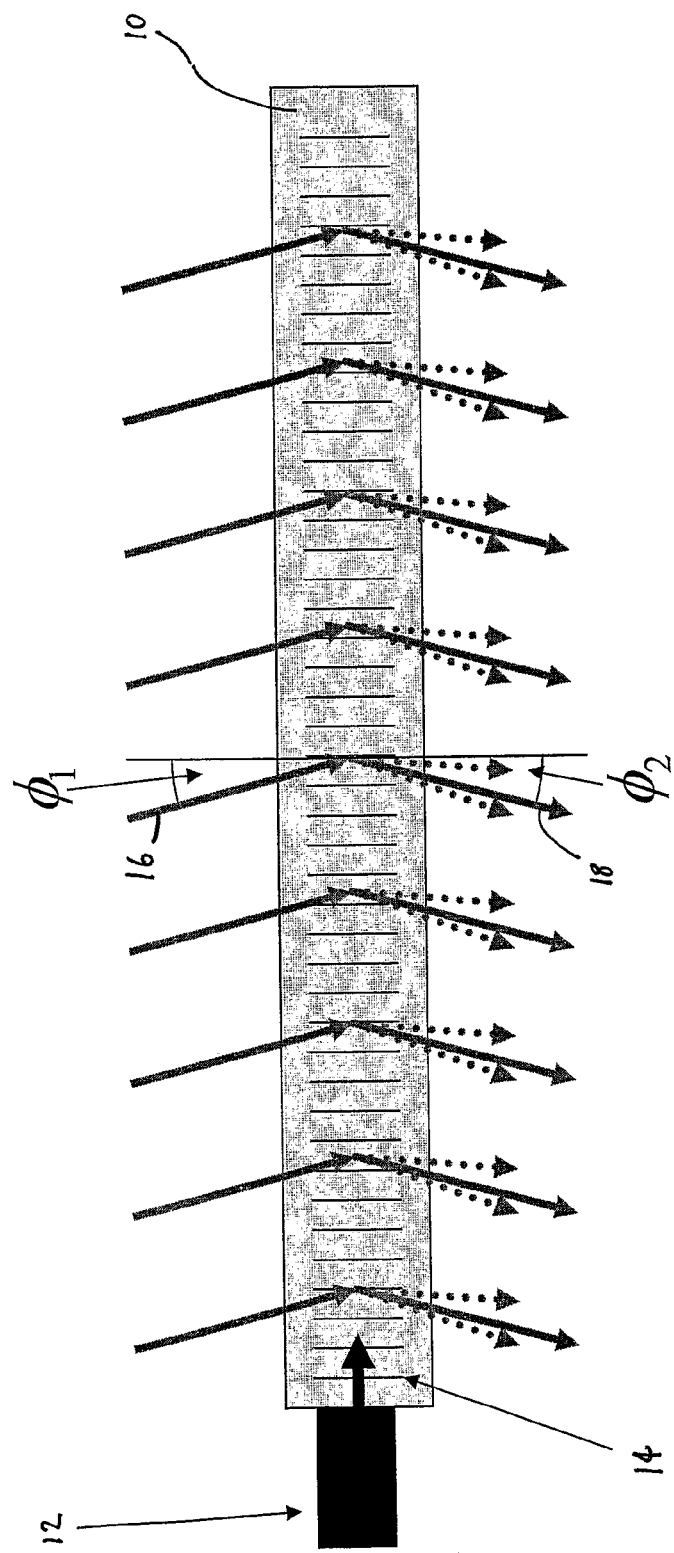
FIG. 1 shows an acousto-optic deflector (AOD) and the principle of diffraction of a laser beam using an ultrasonic acoustic wave.

In order to fully understand the invention, it is useful to explain the technical effects relevant to the invention. FIG. 1 illustrates the principle of Bragg diffraction in an acousto-optic deflector.

The acousto-optic deflector comprises a crystal 10 and a crystal transducer 12. The crystal is preferably a high-efficiency anisotropic acousto-optic crystal such as a $TeO_2$ crystal. The crystal transducer 12 is attached to one side of the crystal and is arranged to propagate an ultrasonic acoustic wave 14 through the crystal, preferably using the slow shear mode of propagation.

An incoming laser beam 16 entering the crystal at an angle $\Phi_1$ will be diffracted by the acoustic wave and the first order component of diffraction will have an angle $\Phi_2$ as shown in FIG. 1. The first order component of diffraction is labelled 18 in FIG. 1. There will also be a zeroth order component of diffraction which is simply a continuation of the input laser beam 16, i.e. the zeroth order of diffraction is an undeflected laser beam.

The laser beam 16 typically has a width of 10 to 15 mm and the plural beams illustrated in FIG. 1 are merely illustrative of a single wide laser beam.

The equation governing the angle of diffraction is:

$$\phi_2 - \phi_1 = \frac{\lambda_0 f_{ac}}{V_{ac}} \tag{1}$$

where $\Phi_2-\Phi_1$ is the angle of diffraction, $\lambda_0$ is the wavelength of the laser beam, $f_{ac}$ is the frequency of the acoustic wave propagating in the crystal and $V_{ac}$ is the velocity of the acoustic wave propagating in the crystal. In FIG. 1, the acoustic wave has a constant frequency $f_{ac}$.

It is apparent from this equation that the amount of deflection that the laser beam undergoes is directly proportional to the wavelength of the laser beam. Thus, higher wavelength components of light will be deflected by more than lower wavelength components.

By manipulating the acoustic wave propagating in the crystal, special effects can be achieved.

For example, the acoustic wave can be "chirped" such that its frequency linearly increases or decreases with time, for example by giving it the form:

$$f_{ac}(t)=f_{ac}(0)+at \tag{2}$$

Figure 2:
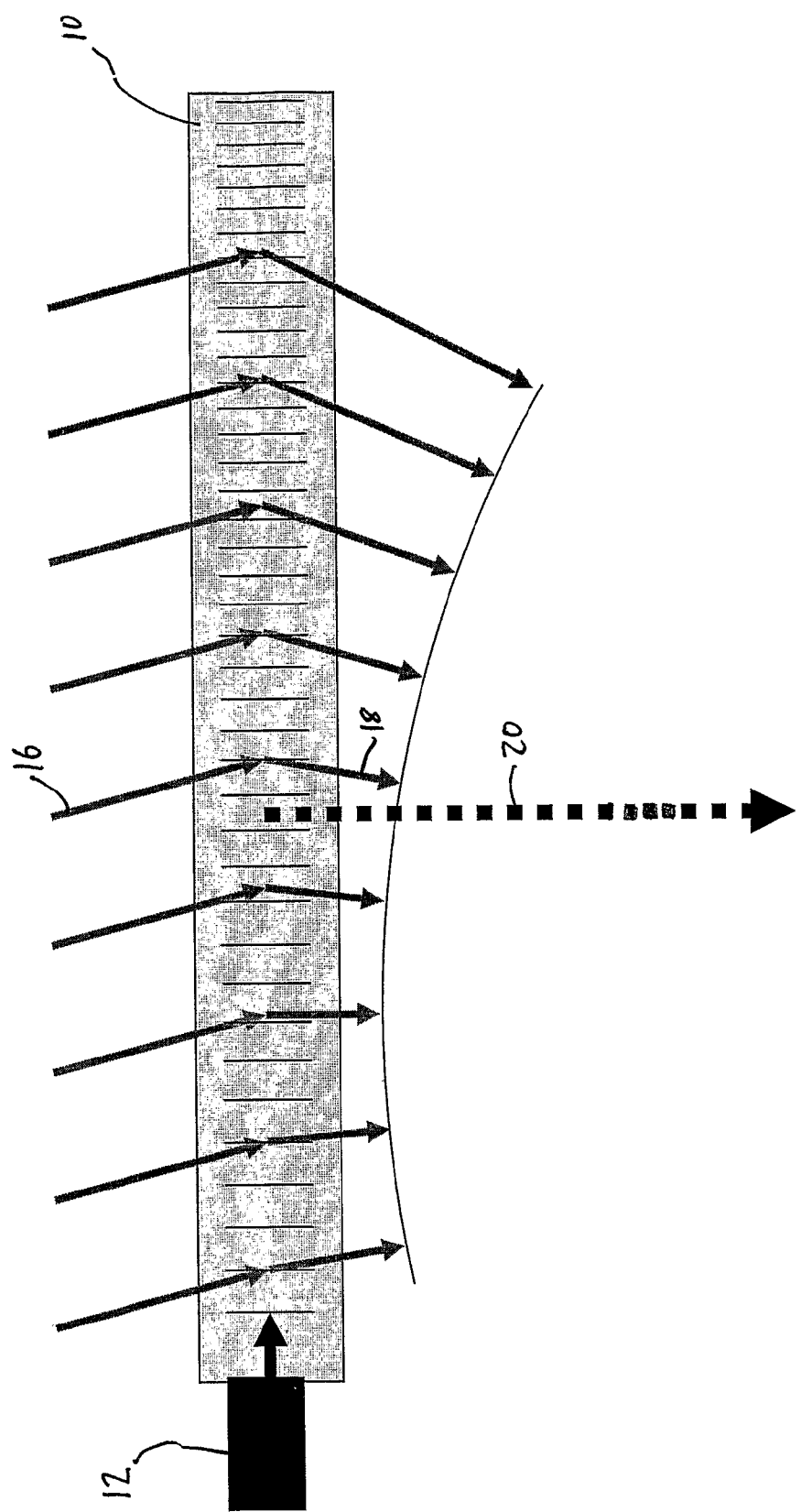
FIG. 2 shows an AOD focussing a laser beam.

In this equation the constant a is known as the "chirp rate" and is measured in MHz per second. It is clear from this equation that the frequency of the ultrasonic wave is a linear function of time. FIG. 2 shows the situation where the chirp rate a is negative, i.e. the frequency of the acoustic wave linearly decreases with time. As the angle of diffraction is proportional to the frequency of the acoustic wave, those parts of the laser beam that are deflected by the high-frequency portion of the acoustic wave will be deflected more than those parts which are diffracted by the low frequency portion. This is illustrated in FIG. 2 and it can be seen that the effect is to focus the laser beam at a position in the general direction of the dotted arrow 20 in FIG. 2. The distance D to the focal position in the vertical direction is given by the following equation:

$$D = \frac{V_{ac}^2}{\lambda_0 a} \quad (3)$$

Figure 3:
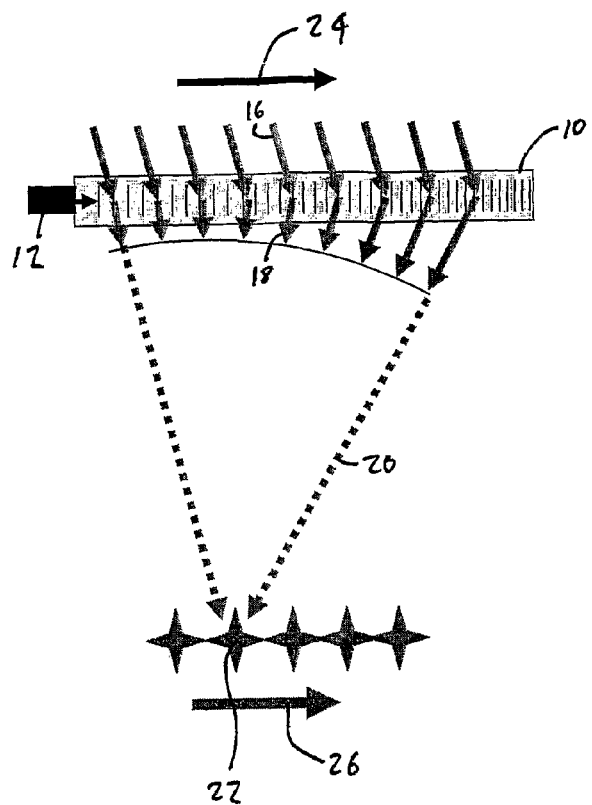
FIG. 3 shows the moving focal spot obtainable with a single AOD.

As illustrated in FIG. 3, the acoustic wave moves in the direction of arrow 24 at the acoustic wave velocity $V_{ac}$. The focal position 22 created by the converging laser beam will thus also move in the direction of arrow 26 at the acoustic velocity. Accordingly, one AOD can be used to focus a laser to a position that moves at the acoustic velocity $V_{ac}$.

Figure 4A:
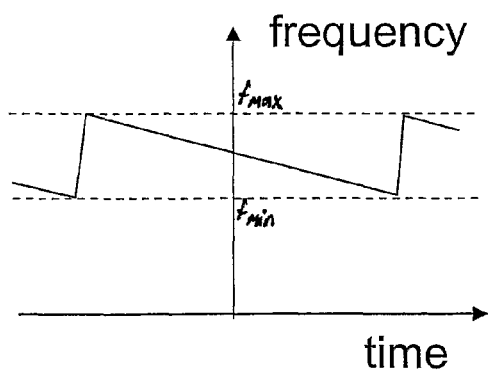
FIG. 4a shows a graph of the frequency of the acoustic wave as it varies with time.

It is also pertinent to point out that the range of acoustic frequencies that may be propagated through the crystal 10 is limited because the diffraction efficiency drops rapidly outside the design range of the AOD. FIG. 4a shows the frequency of the acoustic wave as it varies with time and FIG. 4b shows the frequency of the acoustic wave as it varies with distance.

As can be see from FIG. 4a, it is necessary to keep the frequency of the acoustic wave between the limits $f_{min}$ and $f_{max}$. It is therefore not possible to indefinitely chirp the frequency of the acoustic wave and, once the frequency reaches $f_{min}$ it is necessary to very quickly change the frequency to $f_{max}$ such that the chirping can continue. This creates a "saw-tooth" graph in FIG. 4a. This same saw-tooth pattern occurs in FIG. 4b, but it is reversed because the frequencies present in the acoustic wave on the right-hand side of the crystal represent frequencies at an earlier time point than the frequencies present in the acoustic wave at the left-hand side of the crystal.

For one design of AOD, typical values for $f_{min}$ are 50-60 MHz and typical values for $f_{max}$ are 90-100 MHz. However, a special design of AOD may be provided that is more efficient at lower frequencies, for example 20-50 MHz, more preferably 25-45 MHz, more preferably still 30-40 MHz and more preferably still 32-37 MHz. $f_{min}$ and $f_{max}$ may thus be chosen in accordance with these lower and upper limits. A low range of acoustic frequencies are useful because they minimise the deflection provided by any one AOD and reduce the need to provide AODs that have large acceptance angles. This allows the efficiency to be kept high.

Figure 4B:
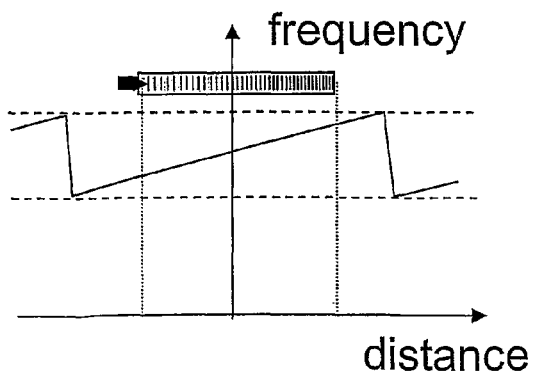
FIG. 4b shows a graph of the frequency of the acoustic wave as it varies with distance across the AOD.

For those points in time where the "fly-back" portion of the graph is present in the central region of FIG. 4b or, in other words, for those points in time where the discontinuity between the highest and lowest frequency exists in the crystal of the AOD, proper focussing cannot be achieved. There are therefore certain periods of time for which the AOD cannot be used for focussing. In two-photon applications, it is therefore important to measure signals induced by the laser pulses only at points in time where there is minimal discontinuity in chirped frequency across the AOD. There is therefore a "duty cycle" limitation on the AOD which duty cycle is the amount of time, expressed as a percentage, that the AOD may be used for useful focussing. It is apparent that this duty cycle will be reduced by increasing the gradient of frequency increase/decrease in FIGS. 4a and 4b.

Figure 5:
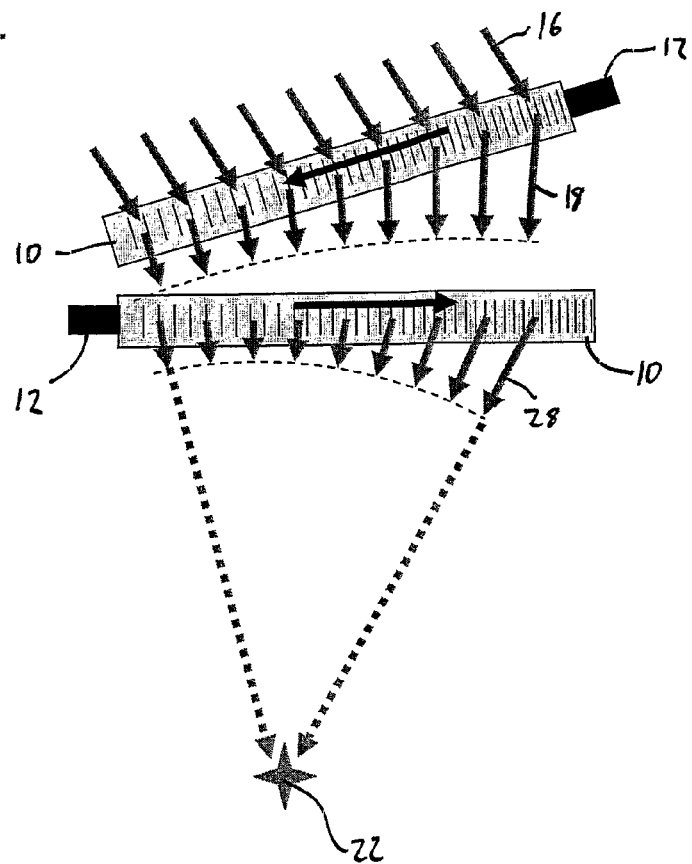
FIG. 5 shows a configuration comprising two AODs which allow a laser beam to be focussed to a fixed spot in the X-Z plane.

The focal spot 22 can be made stationary by utilising a second AOD, as described by Kaplan et al (supra) and as illustrated in FIG. 5.

In this configuration, a second AOD crystal 10 and ultrasonic transducer 12 is utilised and the ultrasonic waves in the AODs are made to propagate in substantially opposite directions. In FIG. 5, the first (upstream) AOD has an ultrasonic wave propagating from the right to the left and the second AOD has an ultrasonic wave propagating from the left to the right. The first AOD modifies the input laser beam 16 to be a focussed laser beam 18 with the focal spot moving substantially from the right to the left and the second AOD modifies the laser beam 18 to be a stationary focussed laser beam 28. As illustrated in FIG. 5, resultant focal spot 22 does not move.

Figure 6:
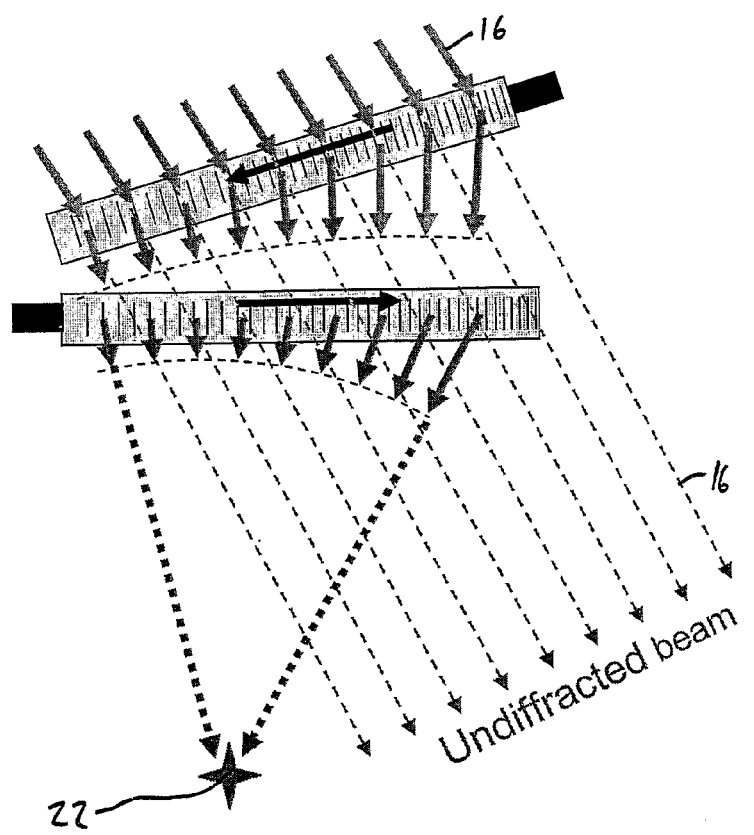
FIG. 6 is a similar view to FIG. 5 but additionally shows the undiffracted zeroth order component of diffraction.

FIG. 6 shows the same set up as FIG. 5 but additionally shows the undiffracted beam (known as the "zeroth order component of diffraction") that is transmitted through the first AOD. Due to the offset positioning of the AODs, the undiffracted beam passes well to the right of the focal spot 22 and so does not interfere with the light reaching the focal spot 22. Baffles or other mechanisms may be used to cut the undiffracted beam out of the system altogether.

For the sound wave direction and diffraction order illustrated, utilising a chirp rate of zero (as shown in FIG. 1) provides a parallel laser beam. Utilising a negative chirp rate (as shown in FIG. 2) provides a converging laser beam. Utilising a positive chirp rate provides a diverging laser beam. These three possibilities are illustrated in FIGS. 7a, 7b and 7c. In any practical system the AODs will be followed by one or more lenses 70 which serve to provide further focussing. Thus, whether the laser beam leaving the AOD system is converging (FIG. 7a), parallel (FIG. 7b) or diverging (FIG. 7c) the subsequent lens system brings the laser beam to a real focus. The system is preferably calibrated such that when the laser beam leaving the AOD system is parallel (FIG. 7b) the point at which the subsequent lens system 70 focuses the beam is designated the Z=0 point. Then, for this configuration, applying a positive chirp rate moves the resultant focal point upwards (see FIG. 7a) and applying a negative chirp rate moves the focal point downwards (see FIG. 7c). In practice, the laser beam passes through several lenses before reaching the physical target.

It will be apparent from FIG. 6 that a problem can arise when the first and second AODs are aligned so as to be parallel. In this case, the undiffracted beam 16 can interfere with the beams reaching the focal point 22. This problem is alleviated in accordance with the second aspect of the invention (please see later).

Figure 8:
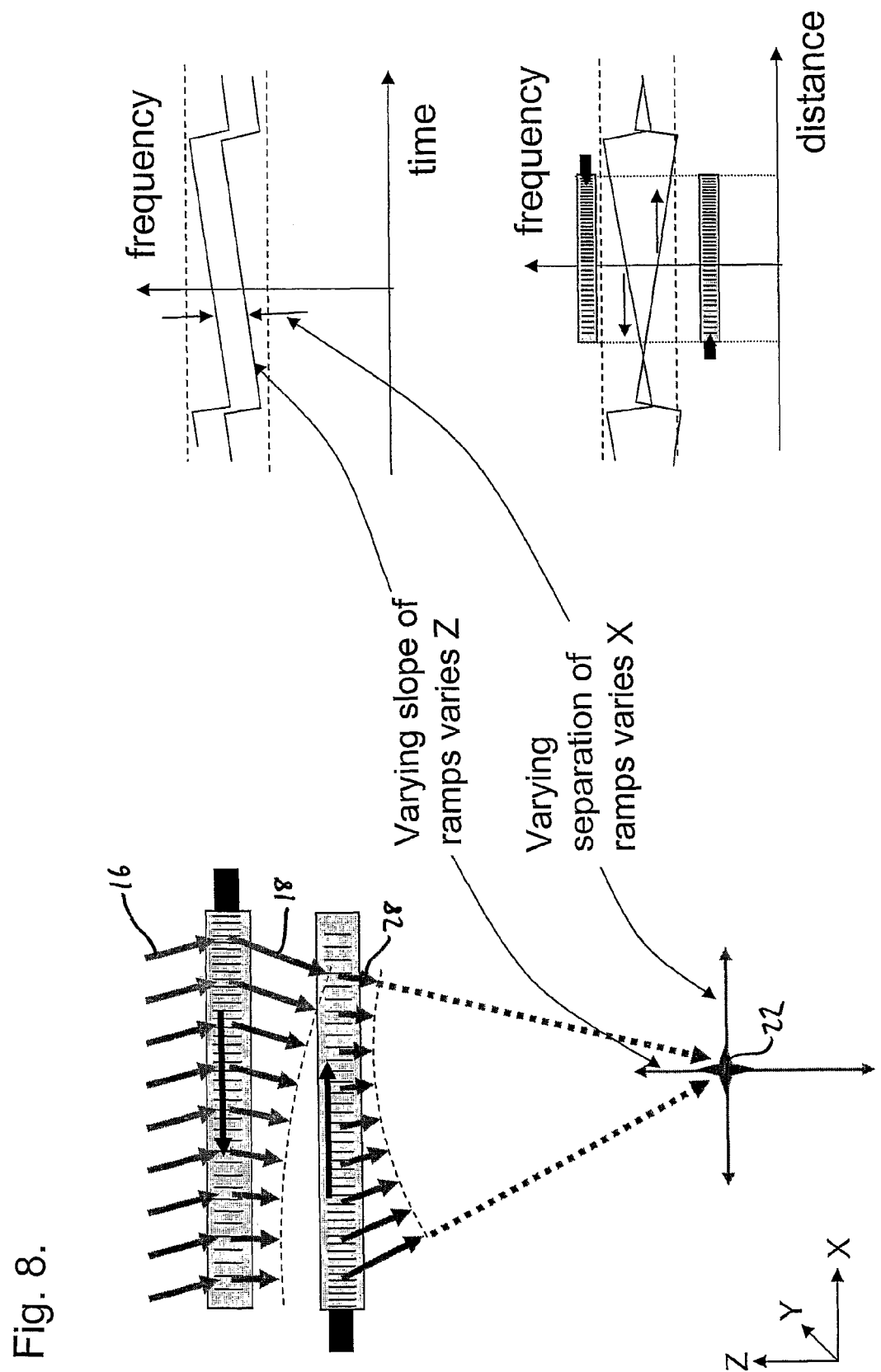
FIG. 8 shows a configuration of two parallel AODs in accordance with the present invention.

FIG. 8 illustrates how the focal spot 22 can be moved within the target volume. The following and subsequent explanations ignore the effect of subsequent lens systems (such as the lens 70 in FIG. 7) in order to provide clarity. In any practical embodiment, such a lens system will be present and the principles below apply equally to the case when the AODs themselves provide a diverging laser beam (in which case there is a virtual focus above the laser beams that is relayed by the subsequent lens optics to a negative Z position). In order to assist in understanding this aspect of the invention the following Figures take the example when the chirp rate is positive which in this configuration produces a converging laser beam.

As explained above, the distance to the focal position is inversely proportional to the chirp rate a. Increasing the chirp rate therefore brings the focal position upward in the Z direction and decreasing the chirp rate brings the focal position downward in the Z direction. As explained in FIG. 8, varying the slope of the frequency time graph (i.e. modifying the chirp rate a) serves to move the focal position 22 in the Z direction. As also illustrated in FIG. 8, the focal position 22 may be moved in the X direction by varying the separation between the two ramps in the frequency-time graph. When the two AODs are excited with acoustic waves that are identical and without any chirp, the resultant focal position is defined as the X=0, Z=0 position. When a chirp is introduced, this moves the focal position in the Z direction. When the absolute frequency of the waves applied to the two AODs differs, this causes the focal position 22 to be moved in the X direction.

Figure 9:
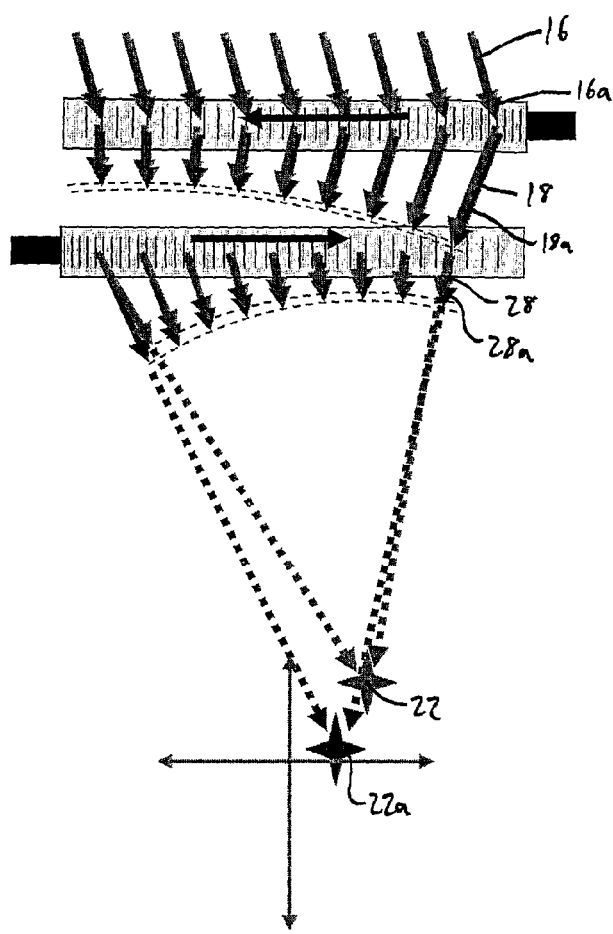
FIG. 9 is similar to FIG. 8 and shows the chromatic aberration that can occur when the input laser has a spectral width.

FIG. 9 illustrates the problem of chromatic aberration and how it causes a laser beam having any sort of spectral width to be focussed to a blurred area, rather than to a distinct position in the X-Z plane.

In FIG. 9, the input laser beam 16 has a certain spectral width. The input laser beam might be a continuous laser beam having several spectral components or might be a pulsed laser beam of a single frequency. When a laser beam is pulsed (that is to say time-windowed by mode locking the laser) this introduces a spectral width to the laser beam. The longest wavelength component of the pulse is shown by the arrows 16, 18, 28 (displayed in grey in FIG. 9) and the shortest wavelength component of the pulse is shown by the arrows 16a, 18a, 28a (drawn darker in FIG. 9).

It can be seen from FIG. 9 that the longer wavelengths are diffracted through a larger angle.

As illustrated in FIG. 9, the focal point 22 for the long wavelength component does not coincide with the focal point 22a for the shorter wavelength component. Wavelengths in between the two illustrated will be focussed to a point somewhere on the line linking focal spot 22 with focal spot 22a. The effect of the AODs is therefore to not property focus a laser beam having spectral width to a unique point.

This problem can be alleviated by using longer laser pulses (which can have a narrower spectral width). However, making the pulses longer makes them less suitable for two-photon microscopy applications as the two-photon microscopy effect is predicated on being able to supply a large number of photons in a very short space of time.

Two-Photon Microscopy System

Figure 10:
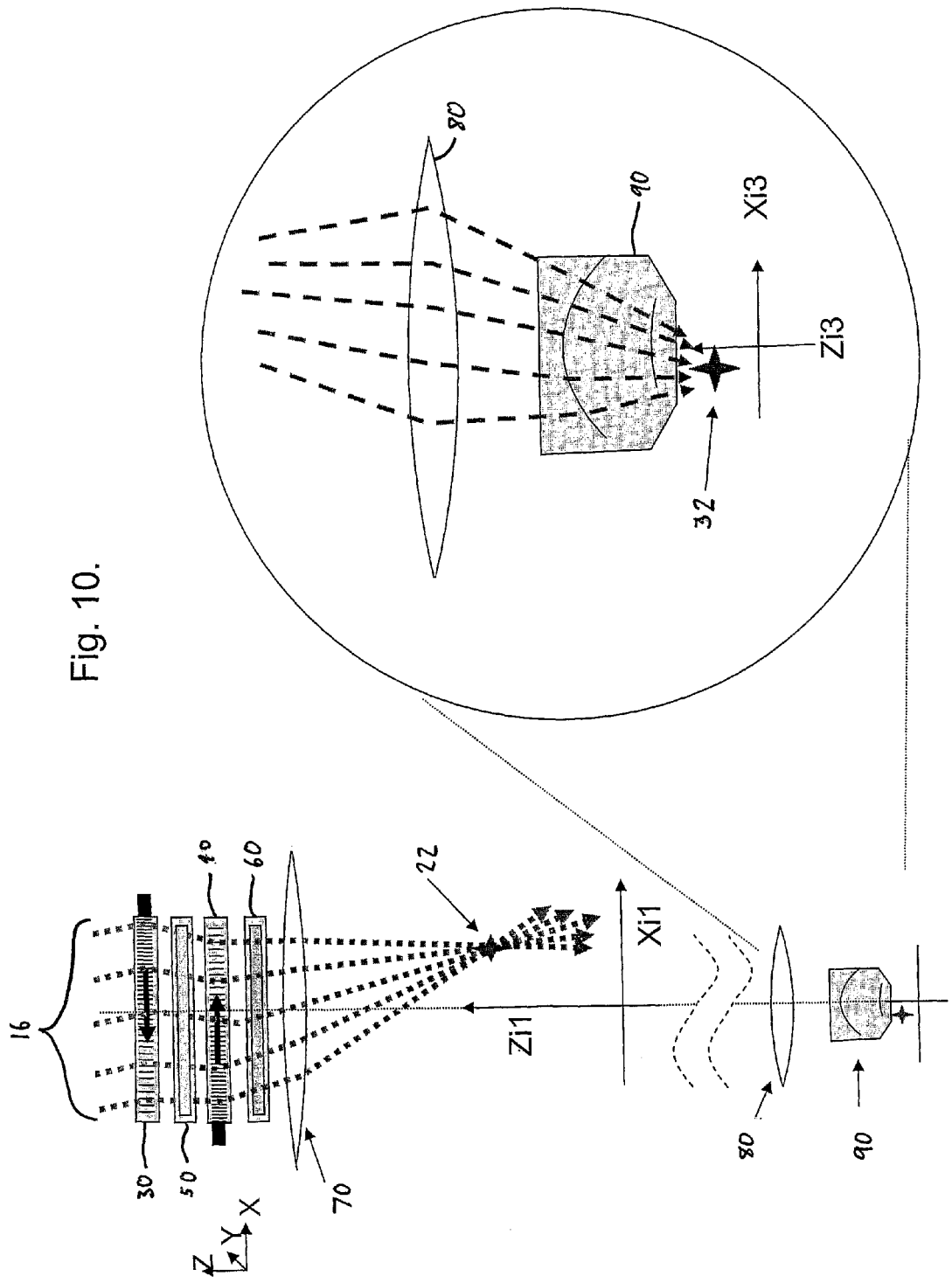
FIG. 10 shows an overview of the components of a two-photon system according to the present invention.

FIG. 10 shows a two-photon microscopy system in accordance with the present invention.

An input laser beam 16 is passed through four acousto-optic deflectors 30, 40, 50, 60 and a lens 70. The laser beams forms a focal spot 22 in the first image field which has Cartesian axes Xi1, Yi1, Zi1. This image is projected through other relay optics (not shown for clarity) which can create a second image field Xi2, Yi2, Zi2. This is projected by a tube lens 80 through a microscope objective lens 90 to form a focal spot 32 in the third image field Xi3, Yi3, Zi3. This third image field is the target field and, in two-photon applications, the target is placed in this field. Such a target might be a slice of brain tissue or other biological material with a fluorescent dye that requires imaging.

The input laser beam 16 in two-photon applications takes the faun of an ultra-short femtosecond or picosecond pulse in order to get sufficiently intense electric fields at the focal point. The pulses are typically spaced in time by a duration very much larger than the pulse length. Typical pulse lengths are 2 ps or less, preferably 500 fs or less, even more preferably 50 to 200 fs. The pulses are typically repeated at a frequency of 50 to 200 MHz (e.g. 80 MHz).

Two distinct experiments can be carried out with a two-photon microscopy system. The first experiment is to image fluorescent materials and such experiments typically require powers of 10 mW to be focussed to an area of just over 1 $\mu m^2$ (corresponding to a power density of around 600,000 W/$cm^2$). Typical laser wavelengths of 800-1000 nm (e.g. 850 nm) are utilised. The second experiment is photolysis in which the laser is used to uncage biologically active compounds. Lasers having a wavelength of 720 nm are often used and the power requirement is much higher, there being a need for in excess of 100 mW of power per micron squared.

In a preferred embodiment of the invention, the laser is supplied by a mode locked Ti sapphire laser tuneable in the near infrared region having an average power of 1 to 10 W and supplying 100 fs pulses at 80 MHz.

Sensitive collection photomultipliers are utilised near to the target area to pick up any florescence from the two-photon excitation of fluorophores in the target. This enables a 3D image to be constructed in imaging applications and further enables any sequence of spots in 3D space to be interrogated by the laser beam for repeatedly monitoring the state of tissue at each spot during dynamic biological processes.

The AODs used in the present invention are preferably shear-mode anisotropic AODs. Suitable materials for the AOD crystal are $TeO_2$ crystals. Such AODs rotate the polarisation of incoming laser light by 90°. The AODs 30, 40, 50, 60 are schematically illustrated in FIG. 10 (and in other Figures of the present application) with no intervening components between them. However, in practice, such components will be present. Typically, these components may include half-wave plates and polarisers (the reason will be explained later). Furthermore, a telecentric relay can be used between each AOD (as disclosed by Reddy & Saggau) to properly couple the AODs together. If such a telecentric relay were not used, then it would be difficult to achieve a stationary focal position, without taking other measures.

The light emitted by the fluorophores is picked up by a photomultiplier (not shown) coupled to the system by a dichroic mirror in the standard fashion.

FIGS. 11a and 11b graphically exemplify how chromatic aberration can be corrected for a single point in the image field according to the prior art. FIG. 11a shows the situation prior to correction. The chromatic aberration has a positive magnitude for all points in the image field and, as can clearly be seen from FIG. 11a, the magnitude of the chromatic aberration varies across the image field in a generally linear fashion. In FIG. 11a, the chromatic aberration at the right-hand side of the imaging field is larger than the chromatic aberration at the left-hand side of the imaging field. Using the best compensation methods known in the art, the chromatic aberration can be corrected for a single point in the image field, as shown in FIG. 11b. The single point is here selected to be the centre of the image field such that the magnitude of the chromatic aberration at the extremities of the image field is equal and opposite. This provides the least overall chromatic aberration. However, it is apparent from FIGS. 11a and 11b that the slope of the line defining the chromatic aberration has not at all been changed. The present invention discloses apparatus and methods for modifying this slope so that a chromatic aberration graph similar to FIG. 11c can be obtained. Modifying this slope is referred to herein as at least partially correcting the magnification chromatic aberration.

Chromatic Aberration Correction

Figure 12:
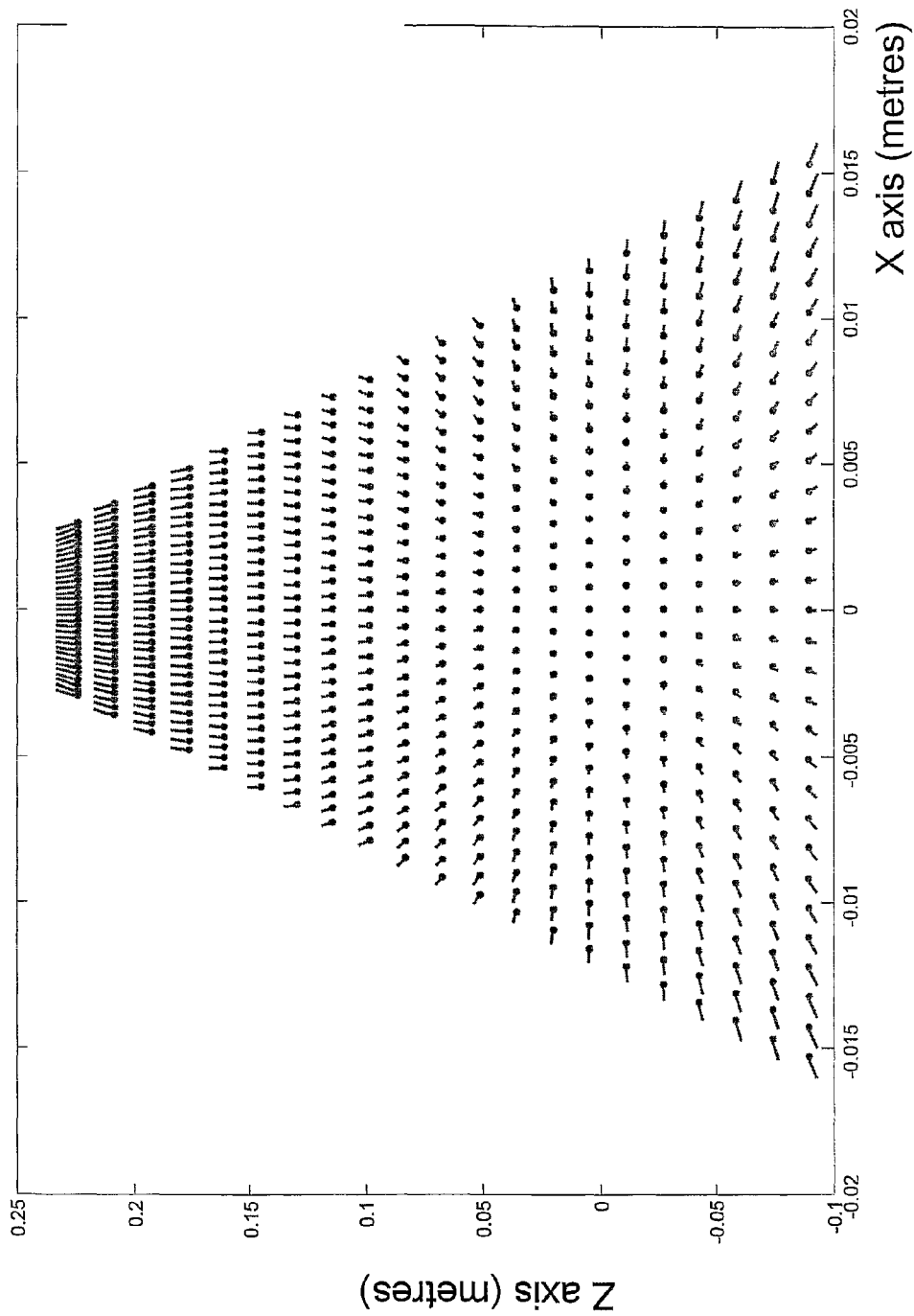
FIG. 12 is a graph showing the chromatic aberration at various points in the image field.

FIG. 12 shows the effect of chromatic aberration (as explained in FIG. 9) for points in the first image field Xi1, Yi1, Zi1 of FIG. 10.

In this embodiment, the lens 70 has a focal length of 0.3 m and this focal point is allocated the zero point along the Z-axis. The zero point along the X-axis is the point of symmetry (i.e. the centre line) of the lens 70. The dots in FIG. 12 show positions in the image field that the shortest wavelength components of a 1 ps laser pulse at 850 nm can be focussed to by varying the chirp and frequency difference between the first and second AODs used to focus in the X-Z plane. The lines emanating from the dots show the points where the other frequency components of the 1 ps pulse will be focussed.

Thus, the end of the line furthest from the dot represents where the longest wavelength components of the pulse will be focussed.

Some observations can be made about the nature of the chromatic aberration. Firstly, in common with the results of Kaplan, Salomé and Reddy & Saggau (supra), there is no chromatic aberration at the point Xi1=Zi1=0. The reason for this is that, at this point, there is no net X deflection and the AODs are being operated with acoustic waves having a single frequency and there is no chirp to produce Z focussing. All frequency components are therefore focussed to the same spot. As one moves along the X-axis from this "compensation point" the amount of chromatic aberration increases accordingly. Similarly, as one moves along the Z-axis, the amount of chromatic aberration increases. Looking at FIG. 12 as a whole, for positions in the image plane at Z<0.15 m, the chromatic aberration seems to have the effect of magnifying the longer wavelength components in the image plane more than the shorter wavelength components. In other words, if FIG. 12 were re-drawn such that the longer wavelength components were shown as dots, this graph would look like a magnified version of the dots representing the shorter wavelength components. This magnifying effect of the chromatic aberration is referred to herein as magnification chromatic aberration.

FIG. 12 is illustrated for a 1 ps pulse. For even shorter pulses, such as 100 fs, even more chromatic aberration is apparent.

Another observation from FIG. 12 is that the X dispersion (i.e. the chromatic aberration in the direction of the X-axis) reduces to zero for the value of Z=0.15. Analysis shows that, for the case when the imaging lens 70 is very close to the final AOD, this will occur generally for values of Z at approximately half the focal length of the lens 70.

Figure 13:
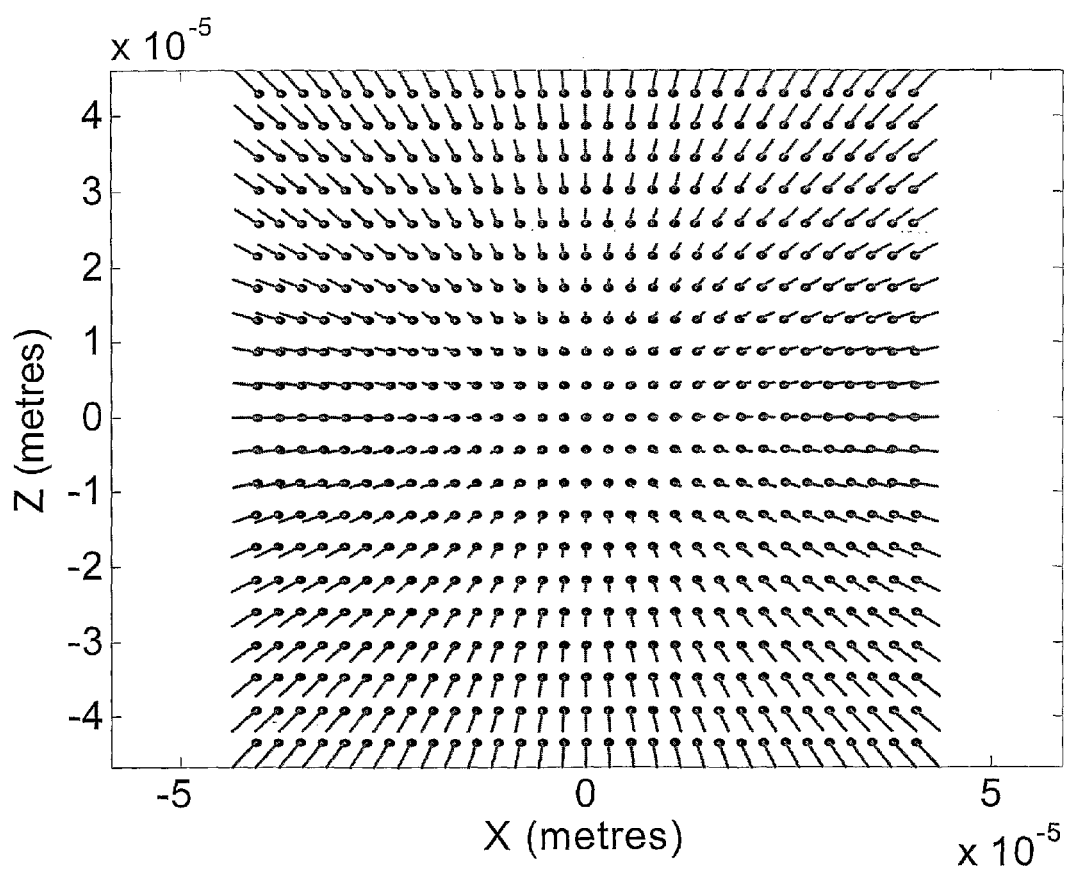
FIG. 13 is a graph similar to FIG. 12 showing the chromatic aberration at various points in the image field.

FIG. 13 shows a view similar to FIG. 12 although here the image is that obtainable under an objective lens having 40× magnification. As with FIG. 12, the tails indicate the direction and relative size of chromatic aberration. In this case the system lenses have been placed in telecentric positions so that the image field is rectangular rather than trapezoidal. As in FIG. 12, chromatic aberration has been reduced to zero for X=Z=0 but has increasing values further away from this compensation point.

The present invention teaches to at least partially correct the magnification chromatic aberration by utilising at least one optical element.

In a first embodiment, this at least one optical element can be a specially manufactured tube lens 80 or microscope objective lens 90.

For a particular X-Y plane at a certain value of Z, all of the chromatic aberration will be in a direction that is directed radially away from the objective lens 90. This fact can be taken advantage of by manufacturing the objective lens 90 so as to have a dispersive quality. That is to say, the objective lens 90 is manufactured from a material which magnifies the longer wavelengths less than the shorter wavelengths. Such lenses can be made from combinations of conventional crown and flint glasses or from diffractive elements. If the correct amount of dispersion is introduced into the objective lens 90 (or alternatively the tube lens 80) the chromatic aberration in the whole of the selected X-Y plane can be substantially corrected. This can increase the NRDV in that X-Y plane by a factor of 50 or more.

Figure 14:
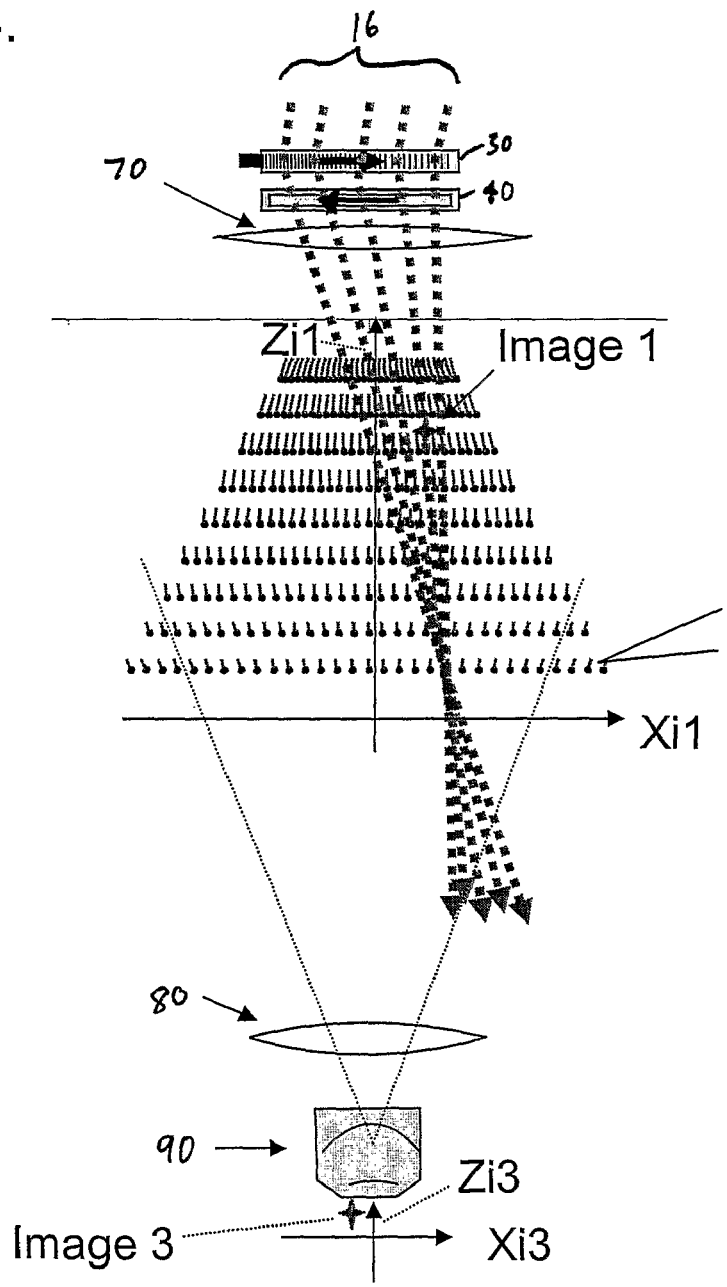
FIG. 14 shows a system with a modified tube lens or microscope objective lens in accordance with the present invention.

FIG. 14 shows a slice through the X-Z plane and also shows first and second AODs 30, 40 designed to allow focussing in this plane. Naturally, a preferred embodiment also includes third and fourth AODs for focussing in the Y-Z plane and the compensation element 80 or 90 can equally correct the magnification chromatic aberration in the Y direction.

The provision of a dispersive lens to correct the magnification chromatic aberration is thus a significant advance in the art as the chromatic aberration can be corrected not just at a single point X=Y=Z=0 but for a whole plane in the image field.

A more preferred embodiment, representing the best mode of operating the invention, provides for significant correction of the magnification chromatic aberration not just in a 2D plane but throughout the majority of the 3D image field. This can be achieved in the present embodiment by utilising a telecentric relay to correct the magnification chromatic aberration.

Figure 15:
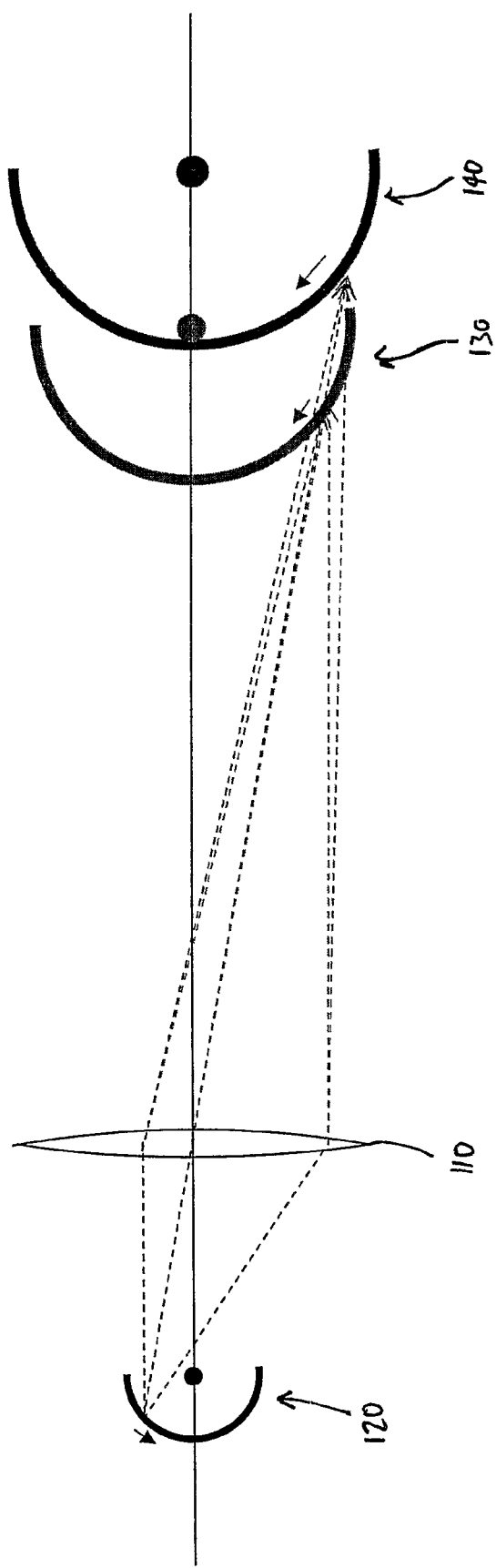
FIG. 15 shows a dispersive lens in accordance with the present invention.

The telecentric relay advantageously comprises two lenses both having dispersive qualities. The first lens is preferably one in which the focal length decreases with increasing wavelength. The second lens is preferably one in which the focal length increases with increasing wavelength. Accordingly, the first lens will tend to project the longer wavelength components to a point nearer to the first lens than the shorter wavelength components. This is illustrated in FIG. 15. An image 120 (here of a semi-circle with a dot at the centre of the curvature of the semi-circle) is projected through a dispersive lens 110 which has a quality of having a reduced focal length with increasing wavelength. Assuming that the light making up the image 120 has some spectral width, the long wavelength components will be projected to form the image 130 and the short wavelength components will be projected to form the image 140. As can be seen in FIG. 15, the long wavelength components are projected to a point closer to the lens 110 than the short wavelength components 140. As a result of this, the long wavelength components 130 are magnified less than the short wavelength components 140. Another way to explain the qualities of the dispersive lens 110 is to state that it has a negative $dF/d\lambda$ wherein F is the focal length and $\lambda$ is the wavelength of light being transmitted through the lens 110.

Figure 16:
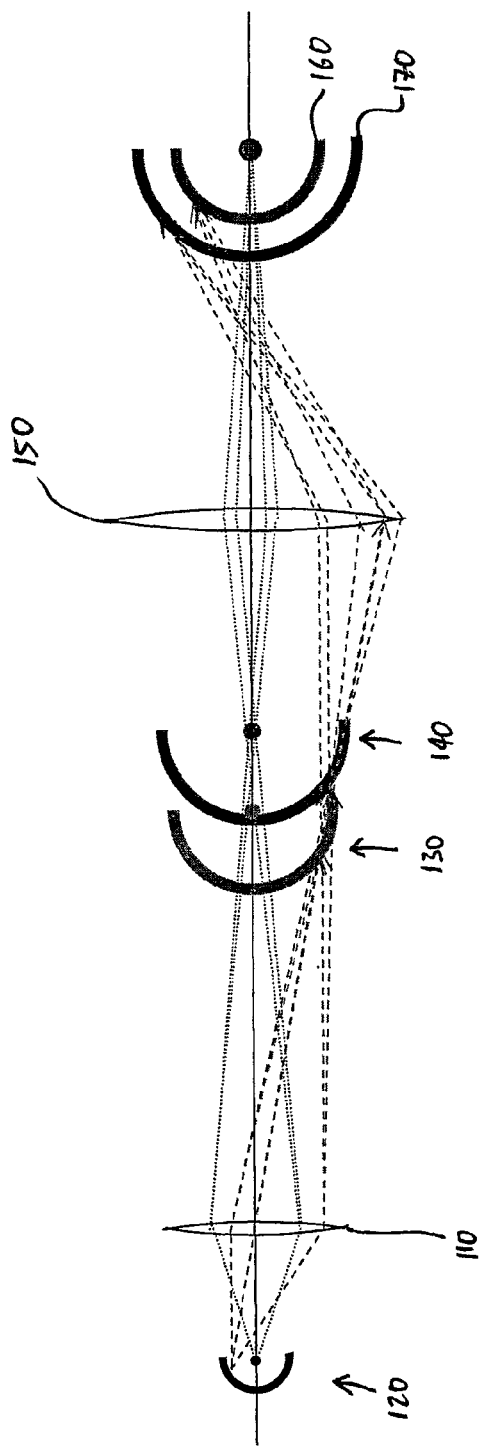
FIG. 16 shows a telecentric relay in accordance with the present invention.

FIG. 16 shows a telecentric relay having first lens 110 and second lens 150.

The second lens 150 has the quality of positive $dF/d\lambda$. In other words, the focal length for longer wavelengths is greater than the focal length for shorter wavelengths. As the longer wavelength components 130 of the projected image 120 are further away from the lens 150 than the shorter wavelength components 140, projection through the lens 150 will tend to realign the centre points of the images 130, 140 to form projected images 160, 170 respectively (see FIG. 16). Furthermore, because the longer wavelength components 130 are further away from the lens 150 than the shorter wavelength components 140, they will be magnified less than the shorter wavelength components. Thus, what results is an image comprising long wavelength components 160 and short wavelength components 170 which are centred on one another but at which the long wavelength components are magnified less than the short wavelength components.

Such a telecentric relay can be utilised in the system of FIG. 10 to project the first image (in the Xi1, Yi1, Zi1 coordinates) to the second image (not shown) or to project the second image to the third image (in the Xi3, Yi3, Zi3 coordinates). As will be apparent from a consideration of FIG. 12, the effect of the relay in reducing the magnification of the longer wavelength components will be to substantially correct the magnification chromatic aberration that exists in the first image.

The lenses of the telecentric relay can be made of any dispersive material such as combinations of conventional crown and flint glass lenses and diffractive elements. Furthermore, the invention is not limited to utilising two lenses and more or less may be used.

Figure 17:
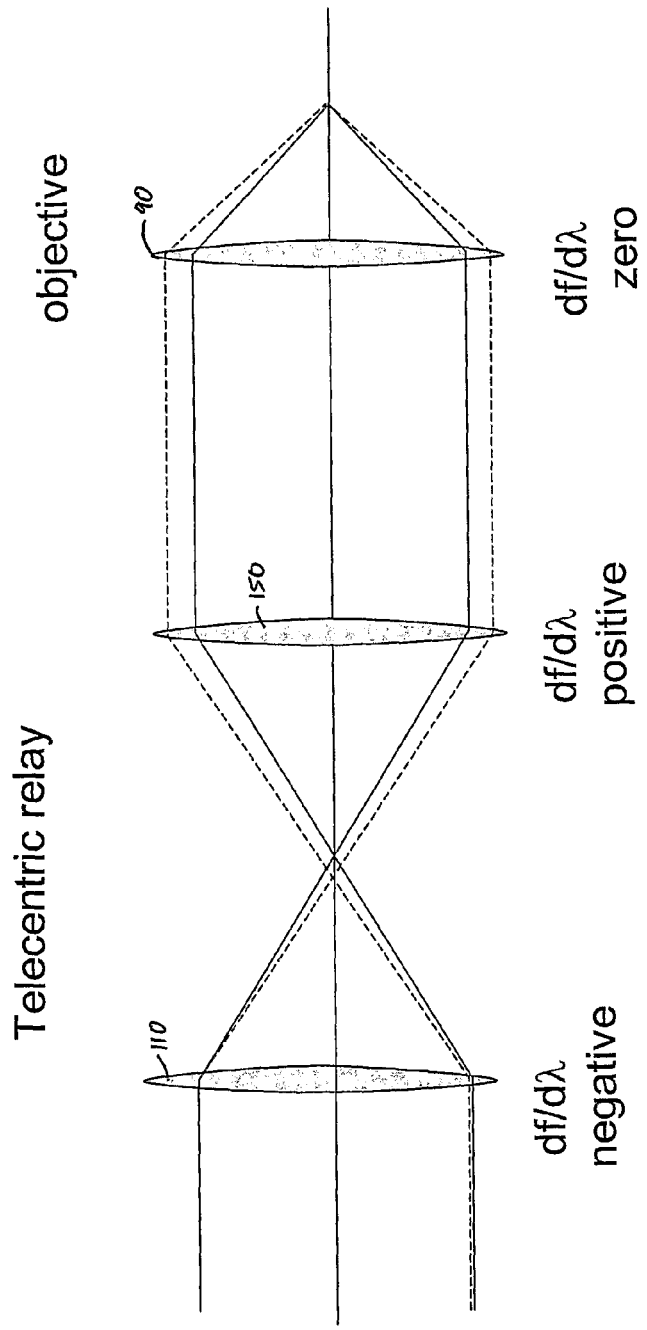
FIG. 17 shows the telecentric relay in accordance with the present invention together with an objective lens.

FIG. 17 shows a view similar to FIG. 16 but also including the microscope objective lens 90. As in FIG. 16, the first lens 110 has a negative $dF/d\lambda$ whereas the second lens 150 has a positive dF/dλ. The objective lens 90 has a dF/dλ of zero. The dotted line of FIG. 17 shows light of a longer wavelength than the solid line. At the final image, the fact that the longer wavelength is focussed on the image from a larger numerical aperture shows that it has a smaller magnification.

Figure 18:
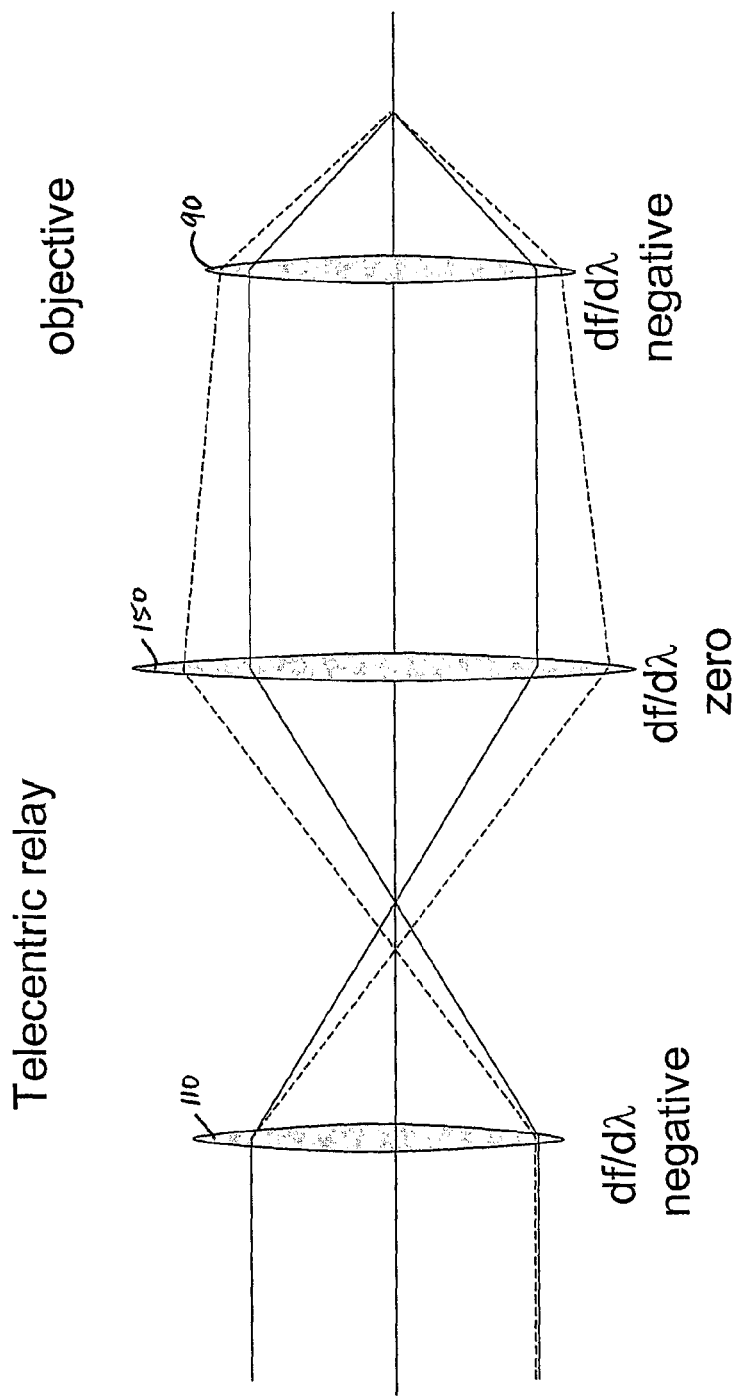
FIG. 18 shows a telecentric relay and objective lens in accordance with another configuration of the present invention.

FIG. 18 shows an alternative embodiment in which first lens 110 has a negative dF/dλ, second lens 150 has zero dF/dλ and objective lens 90 has a negative dF/dλ. It is apparent from this diagram that, yet again, the longer wavelengths are magnified less than the smaller wavelengths.

Figure 19:
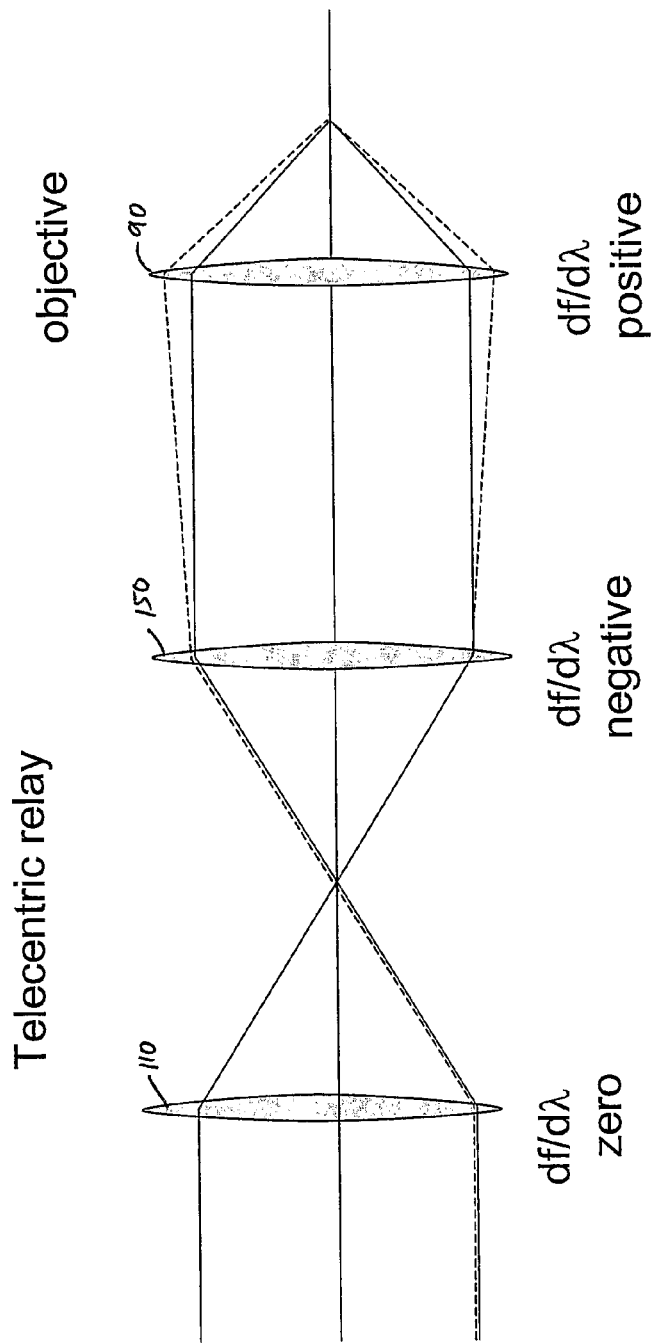
FIG. 19 shows a telecentric relay and objective lens in accordance with a further configuration of the present invention.

FIG. 19 shows a further alternative embodiment. Here, first lens 110 has zero dF/dλ, second lens 150 has a negative dF/dλ and objective lens 90 has a positive dF/dλ. As in the other embodiments, the longer wavelengths are magnified less than the shorter wavelengths.

It will be apparent to one of ordinary skill in the art that various other combinations of lenses can be utilised to achieve the technical effect of magnifying the longer wavelengths less. The Figures presented herein are just some examples from a multitude of possibilities.

Figure 20:
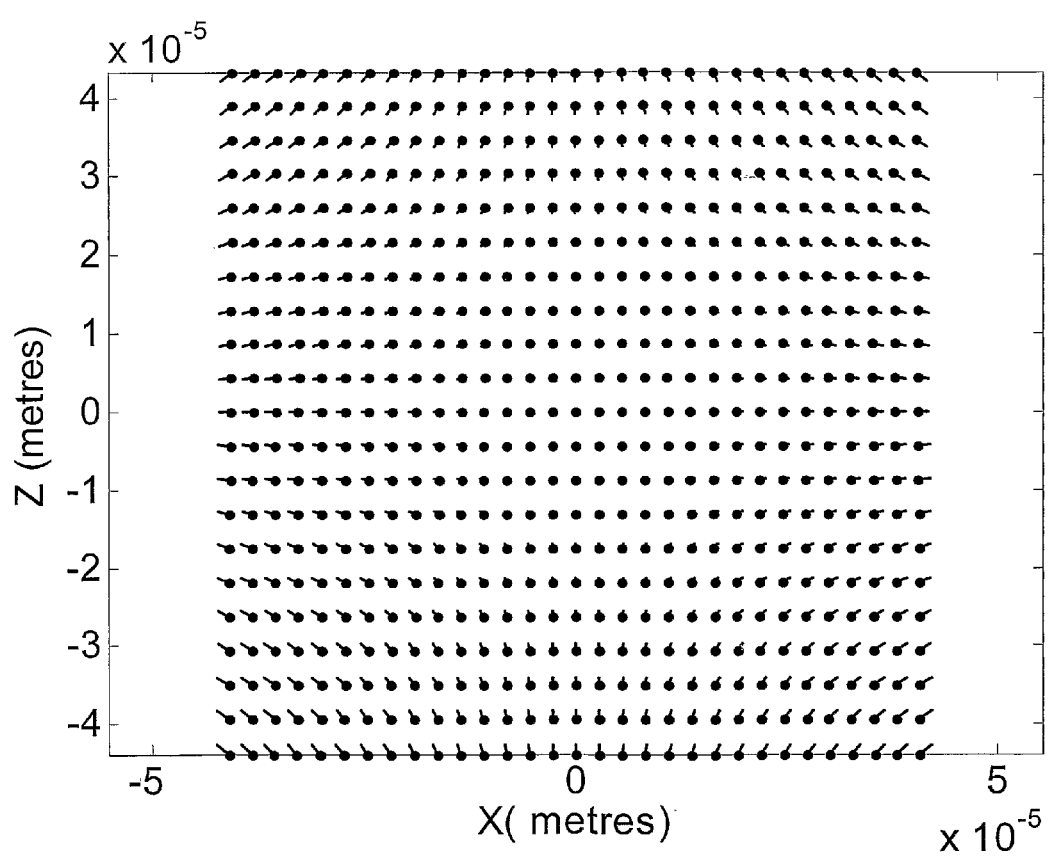
FIG. 20 is a graph showing the improvement in magnification chromatic aberration obtainable with the present invention.

FIG. 20 shows the image after correction and it can immediately be seen that the lines representing the chromatic aberration are much shorter. This translates into an increase in NRDV of over 30 times.

Using the system of the present invention, the magnification achievable is not isotropic in the X, Y and Z volume. In general the magnification in the Z-direction is equal to the square of the magnification in the X and Y-directions. Thus, if the X and Y coordinates are magnified by two times, the Z coordinates will be magnified by four times. Similarly, if the X and Y coordinates are magnified by 0.5, the Z components will be magnified by 0.25.

Figure 21:
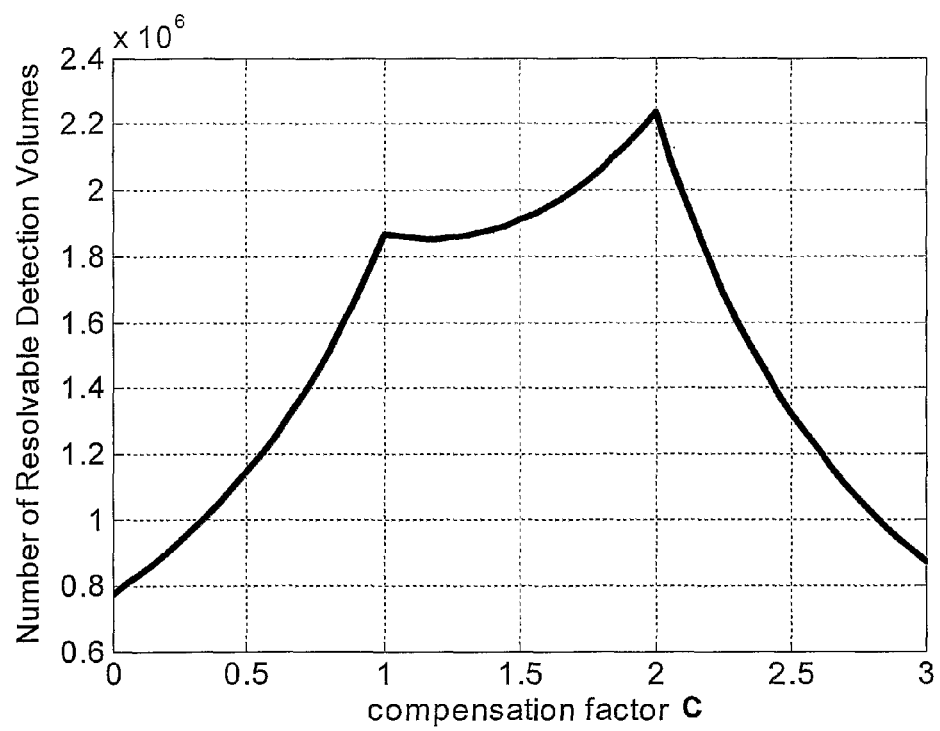
FIG. 21 is a graph showing the number of resolvable detection volumes (NRDV) and how this varies with a correction factor C related to the amount of magnification that the shorter wavelengths are subjected to compared to the longer wavelengths.

FIG. 21 shows a graph of how the NRDV varies with a "compensation factor" C. A compensation factor C=1 is selected to coincide with the amount of chromatic dispersion in the compensator that gives perfect compensation for all the chromatic aberration in the Z-direction. A value of twice this chromatic dispersion (C=2) gives perfect compensation in the X and Y-directions. The compensation factor can be selected in accordance with the application to which the apparatus is put. For example, if the apparatus is being applied in a 2D imaging scenario, where focussing to different points in different Z-positions is not required, the compensation factor C can be set equal to 2 so as to achieve perfect chromatic aberration correction in the whole X-Y plane. This compensation factor also gives the highest NRDV and is suitable for imaging 3D spaces where the depth of interest remains within the high resolution Z range. If greater resolution imaging is required over the largest possible Z range then a compensation factor of near 1 is better albeit at the expense of some loss of resolution at the extremes of X and Y range (see FIG. 21).

Figure 22:
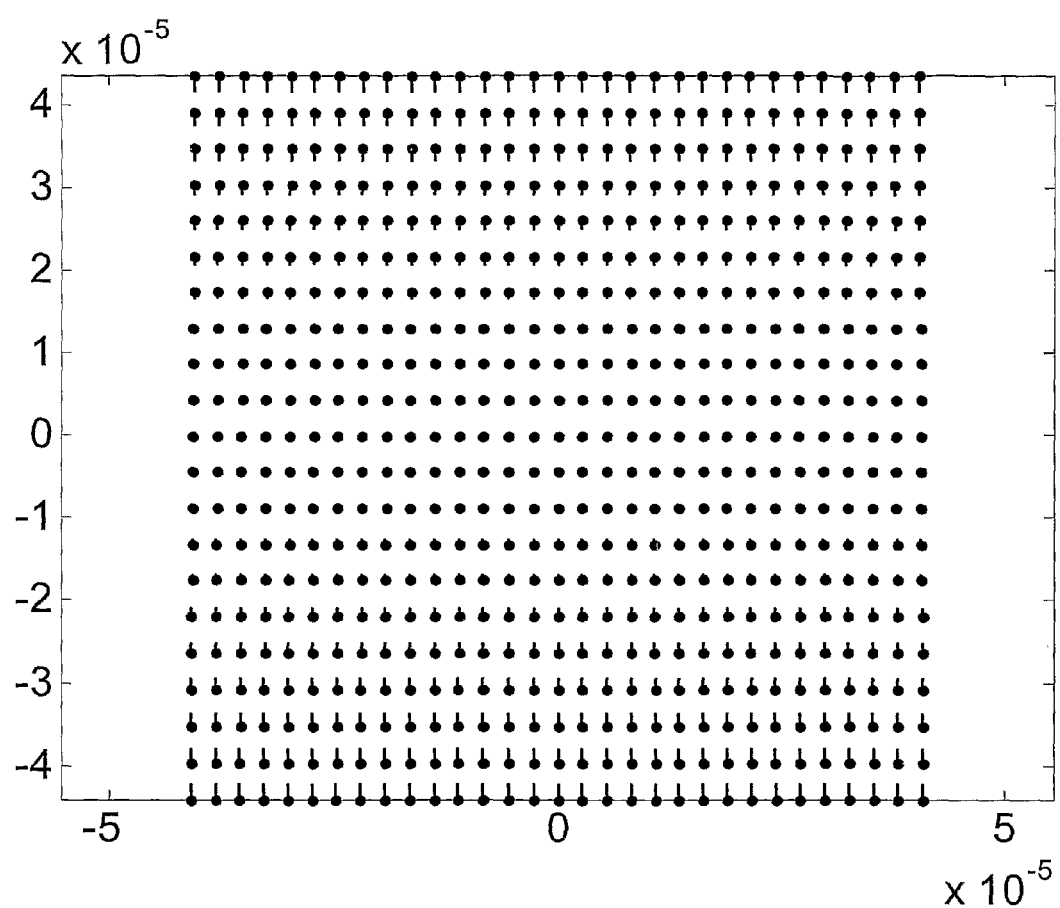
FIG. 22 is a graph similar to FIG. 20 in which the chromatic aberration has been corrected perfectly in the X-direction.
Figure 23:
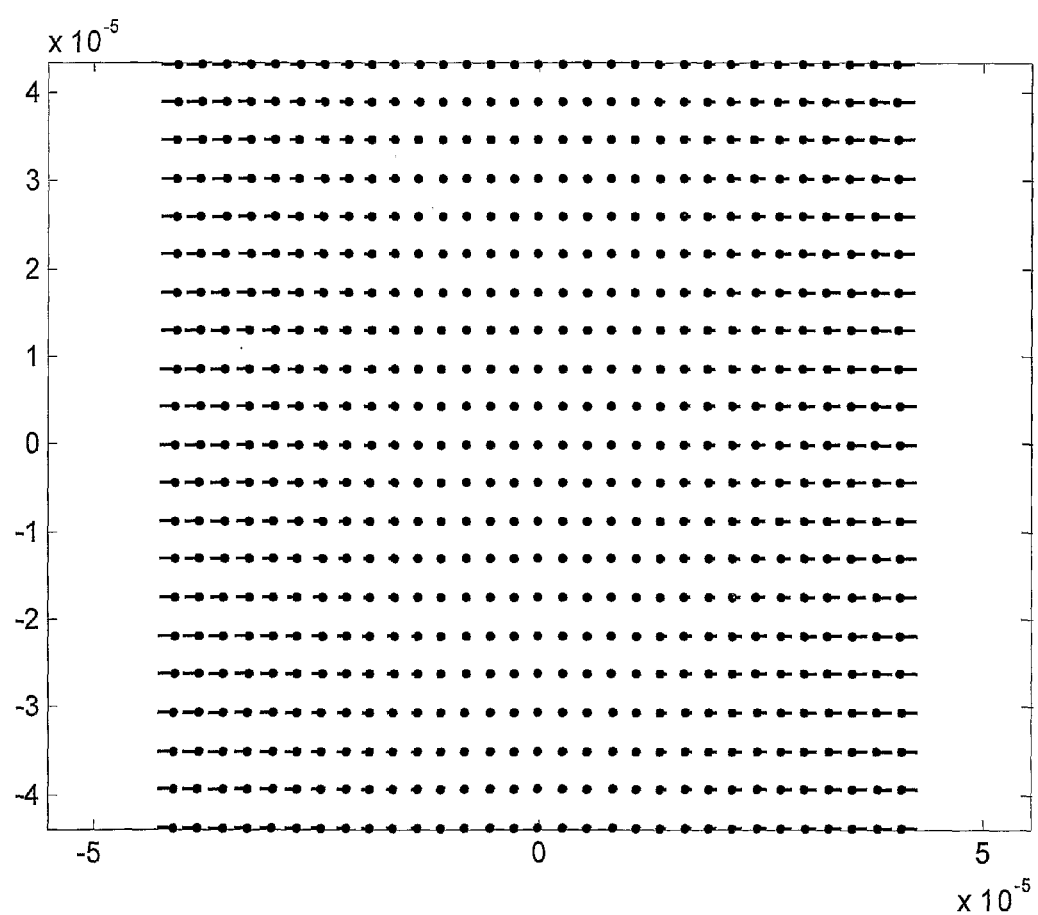
FIG. 23 is a graph similar to FIG. 20, in which the chromatic aberration has been corrected perfectly in the Z-direction.

The parameter C in FIG. 21 can be further defined with reference to FIG. 17. In this symmetrical case, at the design mid wavelength, the rate of change of focal length of the first lens 110 is equal to the positive rate of change of the focal length of the second lens 150, and the input and output beams are parallel and of equal diameter, $$C = \frac{-4\lambda}{f_1} \frac{\partial f_1}{\partial \lambda} = \frac{4\lambda}{f_2} \frac{\partial f_2}{\partial \lambda}$$

where
$f_1$=focal length of lens 110
$f_2$=focal length of lens 150
λ=operating wavelength FIG. 20 shows that the longer wavelength components of the original image have been magnified by less than the shorter wavelength components of the original image. The compensation is such as to slightly overcompensate in the Z-direction and slightly undercompensate in the X-direction (C=1.3). Depending on the application, it is possible to select or position lenses that perfectly compensate in the X-direction (but not perfectly in the Z-direction) (C=2, see FIG. 22) or which perfectly compensate in the Z-direction (but not perfectly in the X-direction) (C=1, see FIG. 23). The example of FIG. 20 is a compromise solution (C=1.3).

Figure 24:
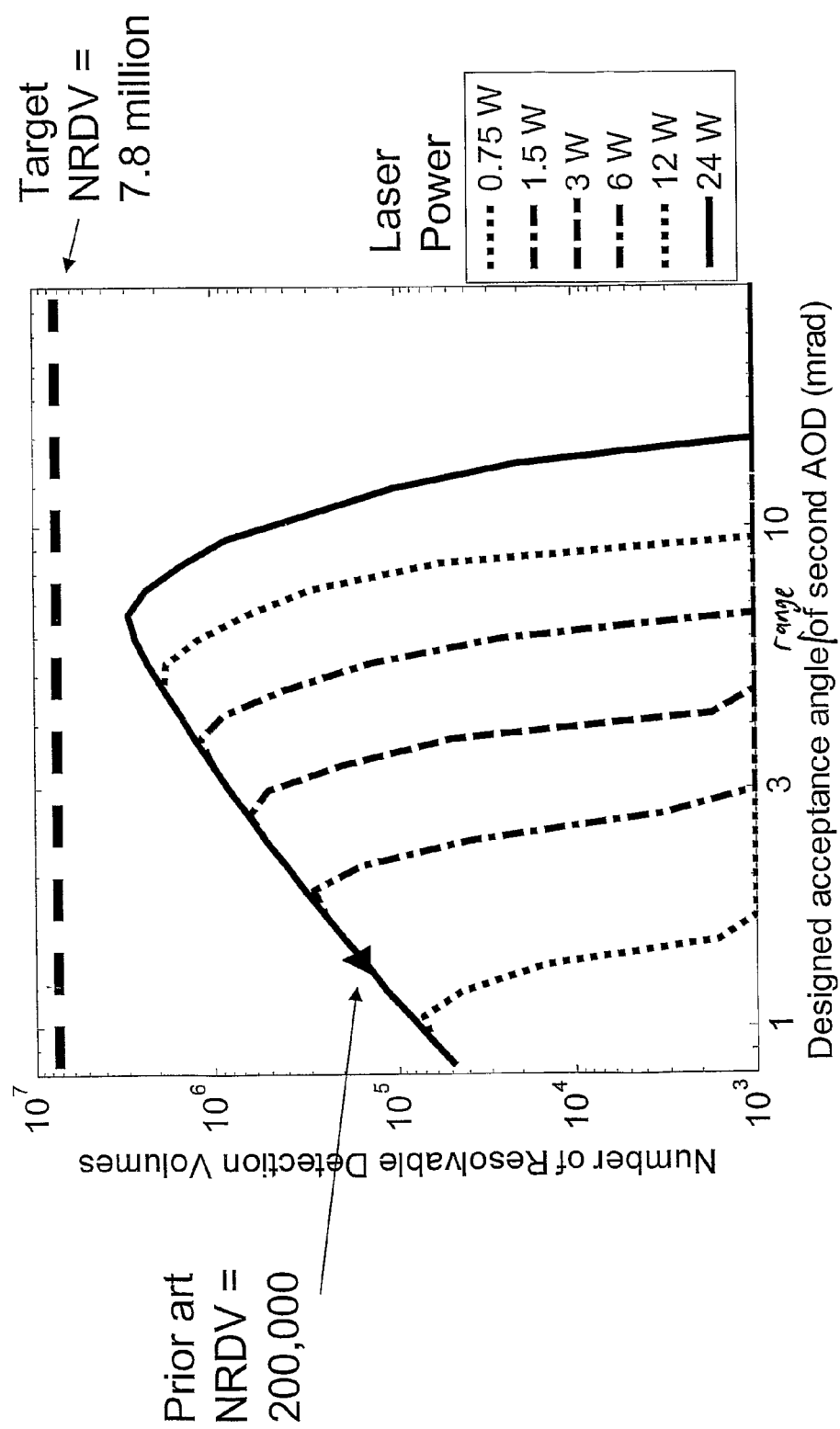
FIG. 24 is a graph showing the number of resolvable detection volumes (NRDV) and how this varies with design acceptance angle range of the second AOD in an AOD pair according to the prior art.
Figure 25:
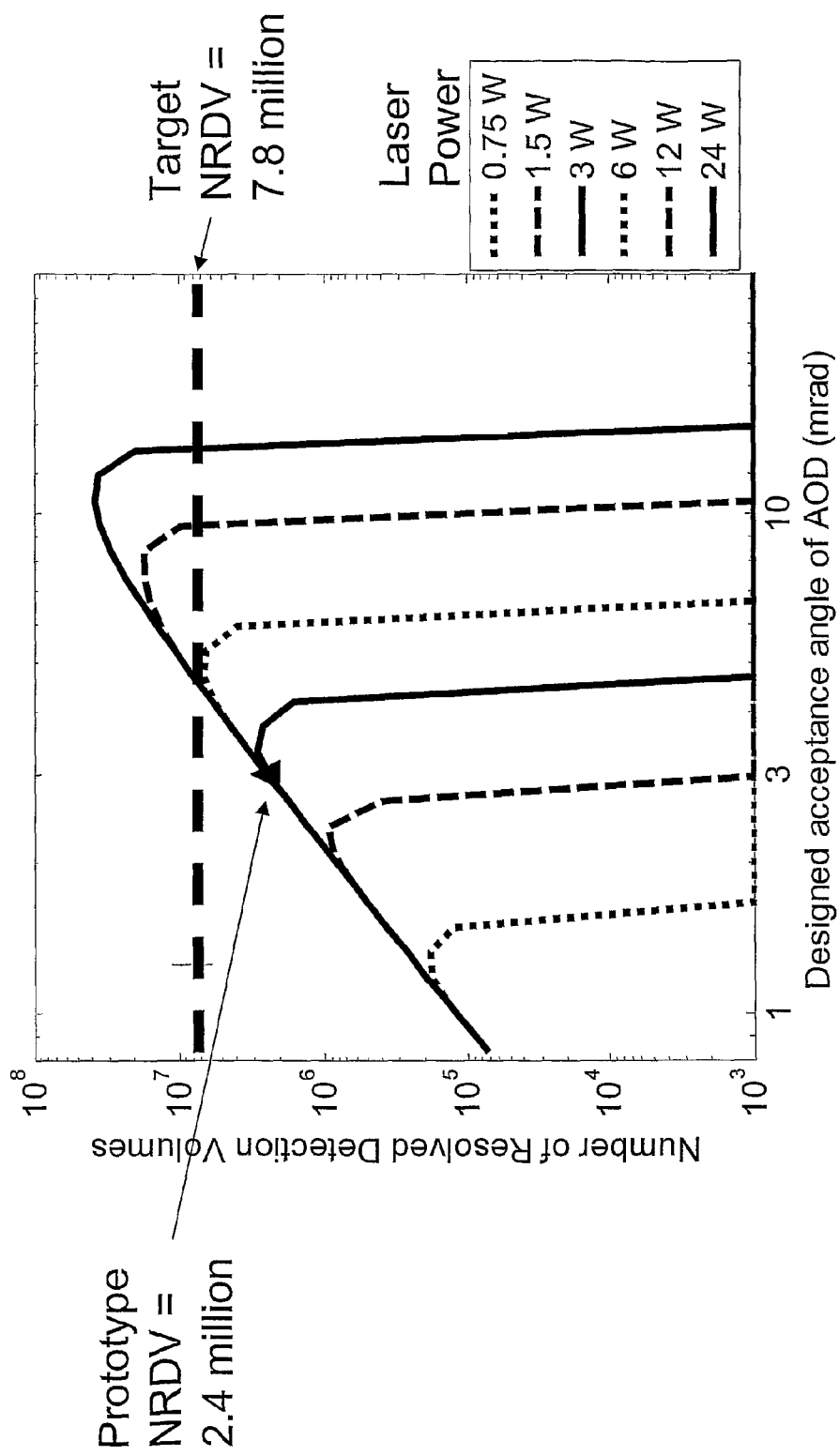
FIG. 25 is a graph showing the number of resolvable detection volumes (NRDV) and how this varies with design acceptance angle range of the second AOD in an AOD pair according to the present invention.

FIGS. 24 and 25 illustrate the effect of the invention in another way.

FIG. 24 shows the NRDV for a prior art system in which the second AOD of the AOD pair has an acceptance angle range of ±1.5 mrad. As can be seen from FIG. 23, this leads to a maximum NRDV of approximately 200,000. The NRDV is calculated as the number of distinguishable points in the image field where enough power can be supplied to achieve the two-photon effect. The threshold density selected for achievement of the two-photon effect is 600,000 W/cm² and FIG. 24 takes account of losses in each optical component.

FIG. 24 also shows notional graphs for laser powers of 6 W, 12 W and 24 W. The best currently commercially available lasers have powers of 3 W. Thus, FIG. 24 graphically illustrates that, even if a laser having a power of 24 W was available, the target NRDV of 7.8 million could never be reached using the prior art systems. Indeed, FIG. 24 shows that, using prior art AOD input acceptance angles of ±1.5 mrad leads to a system having an NRDV of approximately 200,000.

FIG. 25 shows a graph similar to FIG. 24, but taking into account the magnification chromatic aberration correction provided by the present invention. It is firstly apparent from FIG. 25 that, even when an input acceptance angle range for the second AOD in the pair is selected at ±1.5 mrad, the NRDV is larger than in the prior art. Furthermore, the magnification chromatic aberration correction has moved the graphs such that it is now possible to obtain an NRDV of 2.4 million using a 3 W laser. This was simply impossible in the prior art. This represents a 12 times improvement in NRDV compared to the prior art. The present inventors also believe that further optimisation can be carried out to achieve the target NRDV of 7.8 million. For example the threshold 600,000 W/cm² was determined experimentally using laser pulses estimated to be 400 fs long (to account for temporal dispersion in the microscope). Using an optical pre-chirper (as suggested by Iyer et al) to pre-compensate the laser pulses entering the microscope would enable the 100 fs pulses to be delivered from the objective and would thus reduce this threshold considerably and enable wider acceptance angle range AODs to be used. This would easily enable the 7.8 million MRDV target to be achieved.

Zeroth Order Component Blocking

A comparison of FIGS. 6 and 8 above reveals that any zeroth order components of diffraction occurring in the first AOD of FIG. 8 will be transmitted through the second AOD and can interfere with the image field. The reason for this is that FIG. 8, unlike FIG. 6, has the AODs mounted in a parallel configuration such that the undiffracted beam passes in a very similar direction to the diffracted beam. This problem is alleviated by the second aspect of the invention which involves the use of polarisers and optional half-wave plates to prevent the zeroth order components of diffraction being transmitted.

Figure 26:
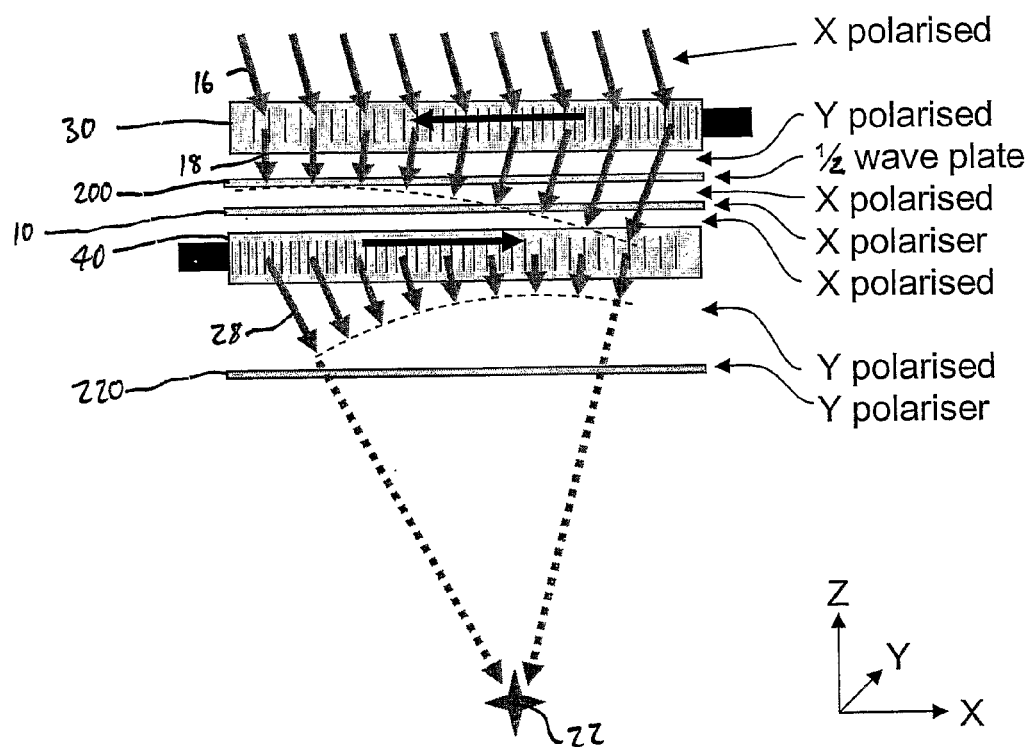
FIG. 26 is an arrangement of two AODs according to the present invention.

In order to be accepted and successfully diffracted by an AOD, the light must have the correct polarisation. In particular, for high efficiency slow acoustic wave AODs (using for example anisotropic tellurium dioxide crystals), the optical input polarisation needs to be aligned with the direction of propagation of the acoustic wave. Thus, where the acoustic wave is such as to cause focussing of an input laser beam in the X-Z plane, the input laser beam needs to be X polarised. Any first order components of diffraction transmitted by the AOD will have had their polarisation rotated by 90° such that they are Y polarised. Such light is not compatible with the second AOD shown in FIG. 7 for example. Thus, according to this aspect of the present invention, a half-wave plate and a pair of polarisers are used, as shown in FIG. 26. Input laser beam 16 having X polarisation is provided to the first AOD 30. The first order components of diffraction 18 leave the first AOD 30 in a Y polarised state. The undeflected zeroth order components of diffraction remain in the X polarised state. A half-wave plate 200 is disposed after the first AOD 30 in order to rotate the polarisation by 90°. Thus, the Y polarised first order components of diffraction are now X polarised and the X polarised zeroth order components of diffraction are now Y polarised. An X polariser 210 is disposed after the half-wave plate and has a function of only allowing X polarised light to pass. Thus, the X polarised first order components of diffraction will pass and the zeroth order components of diffraction will be blocked (because they are Y polarised following rotation by the half-wave plate). These X polarised first order components of diffraction are suitable for input into the second AOD 40 where they will by rotated by 90° to become Y polarised first order components of diffraction. Any undiffracted light leaving the second AOD 40 will be X polarised and so will be blocked by the Y polariser 220 situated downstream of the second AOD. Thus, light reaching the focal spot 22 will solely consist of the first order components of diffraction with any zeroth order components of diffraction being effectively blocked by the polarisers.

With the configuration shown in FIG. 26, the focal spot 22 is actually a line perpendicular to the page because there is no focussing in the Y direction. If, as is preferred, focussing is also required in the Y direction, then an identical configuration to FIG. 26 can be utilised, it being merely rotated by 90° about the Z axis. In this configuration, the first and second AODs 30, 40 perform the focussing in the X-Z plane and the third and fourth AODs 50, 60 perform the focussing in the Y-Z plane.

In this configuration, all of the AODs are mounted in parallel, that is to say the acoustic waves travelling through the AODs travel in parallel planes (parallel to the X-Y plane). Also, in this configuration, the components are mounted in the following order (in the direction of laser propagation): First AOD, half wave plate, X polariser, second AOD, Y polarizer, third AOD, half wave plate, Y polariser, fourth AOD, X polariser.

Figure 27:
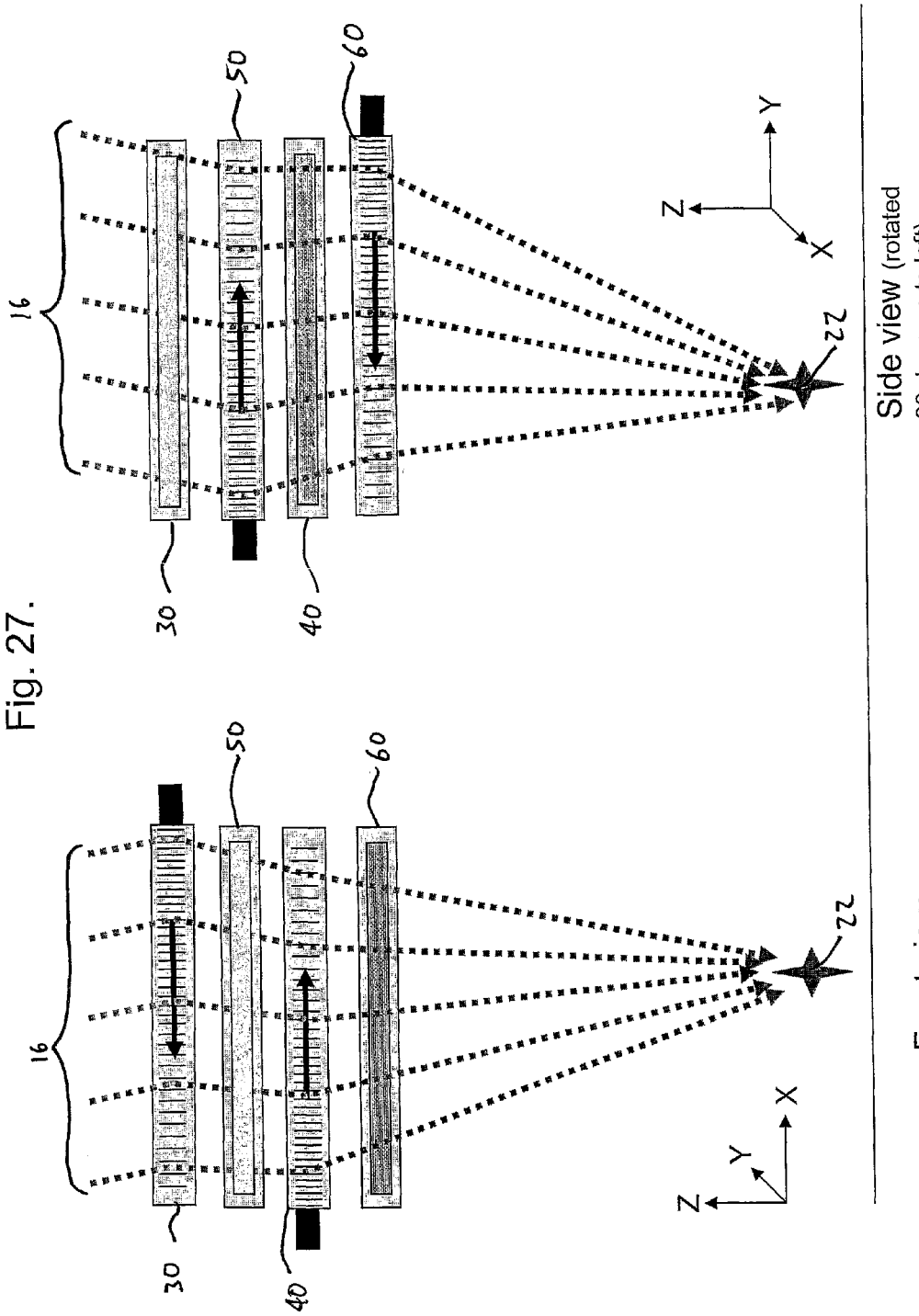
FIG. 27 shows two orthogonal views of an arrangement of four AODs in accordance with the present invention.

There exists an even more preferred configuration of AODs and this is shown in FIGS. 10 and 27.

FIG. 27 shows two orthogonal views of the AOD configuration. The first AOD 30 and second AOD 40 are used to provide focussing in the X-Z plane. The third AOD 50 and fourth AOD 60 are used to provide focussing in the Y-Z plane. As is apparent from FIG. 27, the AODs are configured in the order first, third, second, fourth starting from the laser beam entry end and finishing at the laser beam exit end. This configuration is preferred because it avoids the need to utilise half-wave plates. Not shown in FIG. 27, but preferably present in a practical embodiment, are first to fourth polarisers. A polariser is located subsequent to each AOD. Laser light 16 entering the first AOD 30 will be converted into a zeroth order component of X polarisation and a first order component of Y polarisation. It is desirable to only transmit the first order component. A Y polariser is therefore located after the first AOD to block the zeroth order component. This Y polarised light is suitable for input into the third AOD 50 in which a zeroth order component of Y polarisation and a first order component of X polarisation is produced. A X polariser is therefore located after the third AOD 50. Such X polarised light is suitable for input into the second AOD 40 which produces a zeroth order component having X polarisation and a first order component having Y polarisation. A Y polariser is therefore located after the second AOD 40. This serves to block the zeroth order component. Such Y polarised light is suitable for acceptance by the fourth AOD 60 which produces a zeroth order component having Y polarisation and a first order component having X polarisation. An X polariser is therefore located after the AOD 60 to block the Y polarised zeroth order component. As a result, all light reaching focal spot 22 is the result of properly diffracted first order components and no undiffracted zeroth order components can filter through the system. Furthermore, this configuration does not require a half-wave plate to adapt the polarisation at various stages.

As is well known to those skilled in the art of AODs, the precise degree of polarisation of the first order diffracted wave, although close to linear and at 90 degrees to the direction propagation of the acoustic wave, is not exact. Particularly if the AOD crystal is cut with less than 2 or 3 degrees deliberate misorientation of the optic axis from the direction of propagation of the acoustic wave, the optimised input beam and the diffracted and zero order output beams of light can be slightly elliptically polarised so the configurations described here, which use linear polarisers would not maximally transmit the diffracted wave nor perfectly suppress the undesired undiffracted zero order components of the light. In such cases, to further improve performance, small rotations of inserted half wave plates or insertion of appropriate phase plates with small fractions of a wave correction (e.g. ¼ or 1/20 wave) may fine tune the performance of the configuration concerned. The key point is for the polariser after each AOD to maximally transmit the wanted diffracted first order beams and maximally suppress the unwanted zero order beam. If the polariser is before another AOD, then there may be more polarisation state adjustment before the next AOD to optimise its performance.

Improved Acceptance Angle Crystals

Anisotropic acousto-optic crystals utilised to manufacture AODs typically have a quoted acceptance angle for the laser light. The crystals themselves are optimised for maximum transmission efficiency at this acceptance angle. For the first and third AODs in the system which receive laser light at a constant acceptance angle, such crystals are highly suitable. However, a problem arises when such crystals are utilised in the second and fourth AODs because the acceptance angle will vary across a range defined by the range of deflection angles capable of being carried out in the first and third AODs respectively. These known devices are capable of deflecting an 800 nm laser beam having 3 W of acoustic power over ±20 mrad (17.43 mrad=1°). The efficiency of transmission is over 80%.

FIG. 28 is a graph of the efficiency of the known AOD crystals. FIG. 29 is the same graph viewed from a slightly different angle. Both of the graphs show the diffraction efficiency for various frequencies of acoustic wave and for various incident light angles. It can be seen from the graph that maximum efficiency is obtained with a centre frequency of acoustic wave of about 95 MHz and an instant angle of about 0.121 rad. FIG. 29 shows that acceptable diffraction efficiencies can be obtained in this crystal for a range of incident angles of approximately ±1.5 mrad. If the incident angle presented to the crystals strays outside this range, then quite low diffraction efficiencies will be present which in turn limit the energy being provided to the focal spot and thus limits the possibility of performing the two-photon interactions necessary in two-photon microscopy. It has been found that the diffraction efficiency of an AOD reduces approximately in inverse proportion to its design input acceptance angle. This means that as the overall deflection angle of the four AOD system increases from the ±3 mrad (=2×±1.5 mrad) possible with the standard device pairs, the efficiency falls in proportion to the inverse square of the designed deflection angle.

Figure 30:
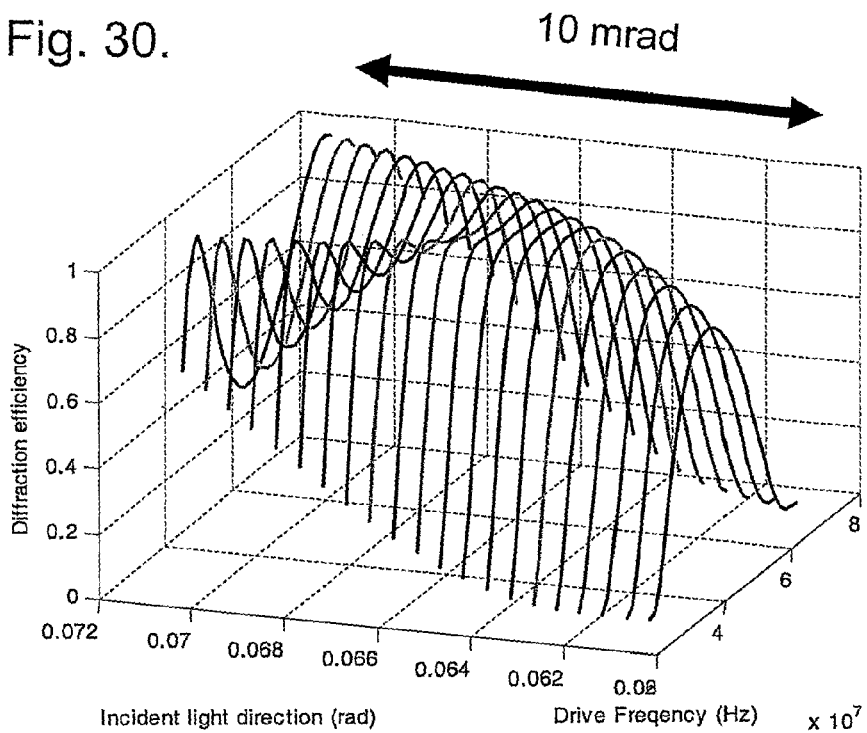
FIG. 30 shows a plot of the diffraction efficiency of an AOD in accordance with the present invention.
Figure 31:
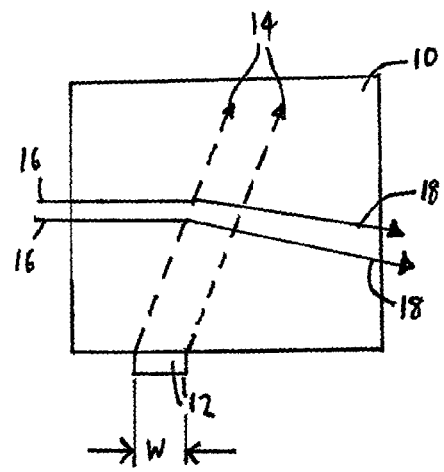
FIG. 31 shows an AOD crystal having a wide ultrasonic transducer.

The third aspect of the invention alleviates this problem by providing an acousto-optic deflector crystal which has a reasonable diffraction efficiency across a larger range of acceptance angles. A graph similar to that shown in FIGS. 28 and 29 for the new crystal is shown in FIG. 30. As can be seen, a crystal configured in this manner maintains a diffraction efficiency of at least 80% of its peak across an incident angle range of 10 mrad. However, the peak diffraction efficiency obtainable is not as high as with the conventional AOD. Thus, the AOD of the invention has a lower peak efficiency than a conventional AOD but accepts laser beams from a wider range of angles at better transmission efficiencies than the conventional AOD. The method by which this effect is achieved will be explained with reference to FIGS. 31 and 32. FIG. 31 shows a conventional AOD crystal 10 with an ultrasound transducer 12 attached to one side thereof. The ultrasound transducer 12 has a width W parallel to the direction of light propagation of approximately 3 mm. This causes the acoustic wave 14 formed in the crystal 10 to be not very diverging. As a result, an input laser beam 16 can be deflected to become laser beam 18 but only if the laser beam 16 is input within a narrow incidence angle range.

Figure 32:
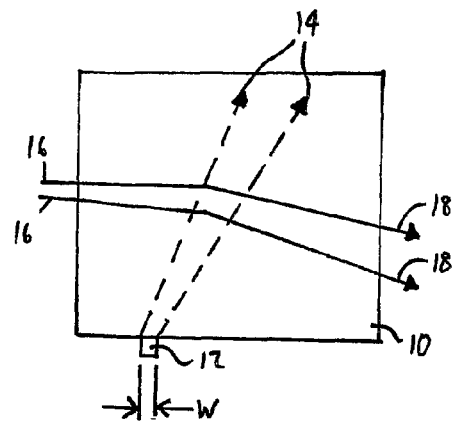
FIG. 32 shows an AOD crystal having a narrow ultrasonic transducer.

FIG. 32 shows an AOD in accordance with this aspect of the invention in which the ultrasound transducer 12 is made much more narrow in the direction of light propagation. In this embodiment, the width W of the ultrasound transducer 12 is 1 mm or less. As shown in FIG. 32, this causes the propagated ultrasound wave 14 to take on a more diverging configuration. This in turn means that a greater range of angles of laser beam 16 can be accepted and successfully diffracted into laser beams 18. Thus, the narrow crystal creates a more diverging acoustic wave which allows the efficient diffraction of laser beams coming from a wider range of angles than if the acoustic wave was less diverging (as in FIG. 31).

Appropriate crystal transducer widths are less than 1 mm, more preferably less than 0.5 mm, more preferably approximately 0.25 mm or less.

Dual Transducer AODs

Figure 33:
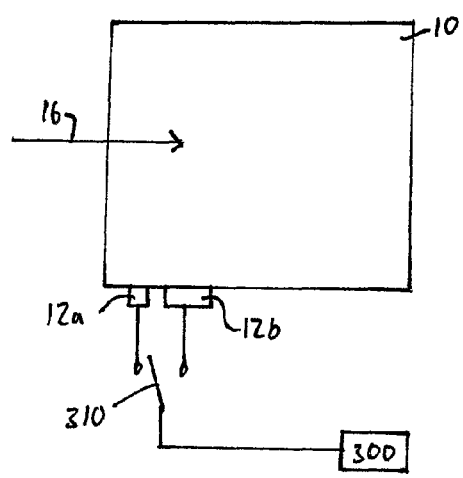
FIG. 33 shows an AOD crystal having a selectable pair of transducers.

This aspect of the invention provides an AOD having two crystal transducers. This is shown in FIG. 33. The first crystal transducer 12a is configured to have a narrow width in the direction of light propagation and the second transducer 12b is configured to be wider in the direction of light propagation. In this embodiment, the transducer 12a has a width of 0.25 mm and the transducer 12b has a width of 3 mm. An excitation source 300 is provided to supply power to the transducers and a switch 310 allows an operator to select whether then first or second transducer is excited.

The provision of this switch allows the AOD to be operated in one of two modes. In the first mode, the wider transducer 12b can be utilised and this optimises efficiency for a narrower range of acceptance angles. This is useful in applications in which it is desirable to deliver a lot of power to a small target volume, such as uncaging (photolysis) applications. The second transducer can be selected where it is important to achieve reasonable transmission across a greater range of acceptance angles, for example when a larger target volume is desired to be imaged with a larger NRDV.

The AODs designed with two crystal transducers, as explained above, are highly suitable for use in the second and/or fourth AODs of the invention.

Multiple Transducer AODs

Figure 34:
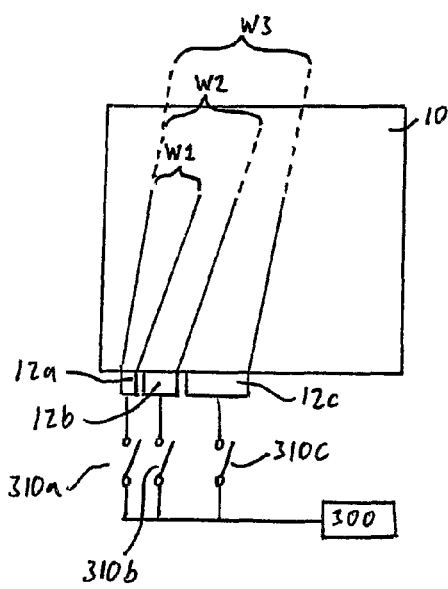
FIG. 34 shows an AOD crystal having three independently selectable transducers.

This aspect of the invention is illustrated in FIG. 34. A single AOD crystal may be provided with two or more crystal transducers. Each crystal transducer may be selectively utilised to help propagate the acoustic wave. In the example of FIG. 34, three crystal transducers 12a, 12b and 12c are shown. The width of the transducers preferably increases in a geometric series, for example by a factor of 2 each time. The crystal transducers preferably have the property that each subsequent transducer is twice as wide as its predecessor. For example, transducer 12a can be 0.25 mm wide, transducer 12b can be 0.5 mm wide and transducer 12c can be 1 mm wide. By appropriate selection of the switches 310a, 310b or 310c, an effective transducer width in the range between 0.25 mm and 1.75 mm can be obtained. This allows the AOD to be utilised in the manner most appropriate to the application for which it is used. It thus helps to provide a general purpose apparatus that can be used for a variety of different experiments. More transducers can be provided if desired.

As shown in FIG. 34, when switch 310a is in the "on" position and all other switches are in the "off" position, the driver 300 excites the crystal 12a only. As this crystal is quite narrow, it provides an acoustic wave W1 that has a high divergence angle. When switches 310a and 310b are activated, this produces acoustic wave W2 which diverges less. When switches 310a, 310b and 310c are activated, this produces acoustic wave W3 which diverges still less and which has the least amount of divergence. When the widest effective transducer is used, this produces an AOD with the highest efficiency but with the narrowest acceptance angle for the incoming laser beam. When the narrowest transducer is used, this produces an AOD with a lower efficiency but a better range of acceptable angles for the incoming laser beam. Accordingly, the width of the transducer can be selected in accordance with the desired trade-off between the efficiency of the AOD and the range of acceptance angles. As an example, the first or third AODs in a four AOD system (i.e. the first AOD for focussing in the X-Z plane and the first AOD for focussing in the Y-Z plane) can be provided with wide transducers to give good efficiency and a low range of acceptance angles whereas the second AOD in each focussing pair can be provided with narrower transducers so as to give a better range of acceptance angles at the expense of lower efficiency.

Improved Crystal Orientation

AOD crystals are usually rotated by about 6° about the X-axis and 0° about the Y-axis. This enables the centre frequency to be increased to maximise deflection angle range and avoids the degenerate re-diffraction of power out of the diffracted beam. Because the soundwave propagation is highly anisotropic, the 6° crystal rotation results in the soundwave power propagating at an angle of about 50° to the Y-axis.

The crystal orientation is measured with respect to the crystal axes and the crystal axes can be determined using an X-ray diffraction technique, as described by Young et al, "Optically Rotated Long Time Aperture TeO$_2$ *Bragg Cell*", *Advances in Optical Information Processing, IV,* 1990, SPIE Vol. 1296, pp 304-316.

FIGS. 32 and 33 are also representative of another aspect of the invention in which the crystal of the acousto-optic deflector has a particular orientation. In this orientation, the input laser beam is defined as being the negative Z axis ([001] direction) and the crystal structure is rotated by 2° about the X axis ([110] direction) and 3° about the Y axis ([110] direction). With this crystal orientation, the soundwave power propagates at an angle of about 20° to the Y-axis and it has been mathematically modelled that this reduces aberration in the image. The 3° tilt about the Y-axis is necessary to avoid loss from degenerate mode.

It has also been found that reducing the centre frequency of the acoustic waves from the range of 50 to 90 MHz to the range 30 to 50 MHz improves the diffraction efficiency with this design.

In accordance with this aspect, the crystal is oriented such that acoustic waves propagating through it have approximately 20° between their wave vector and their Poynting vector. In order to achieve proper focussing, the speed of propagation of the sound waves across the AOD must be identical whether or not the first transducer 12a or second transducer 12b is being used.

This improved crystal orientation can be utilised with the second AOD in one of the focussing pairs (i.e. the AODs labelled 40 and 60). Additionally, it may also be used with a first AOD in each of the pairs (i.e. the AODs labelled 30 and 50). It is preferable that all of the AODs in the system have this improved crystal orientation.

Any of the embodiments and aspects described herein can be provided with AODs according to this orientation.

Compact AOD Configuration

Figure 35:
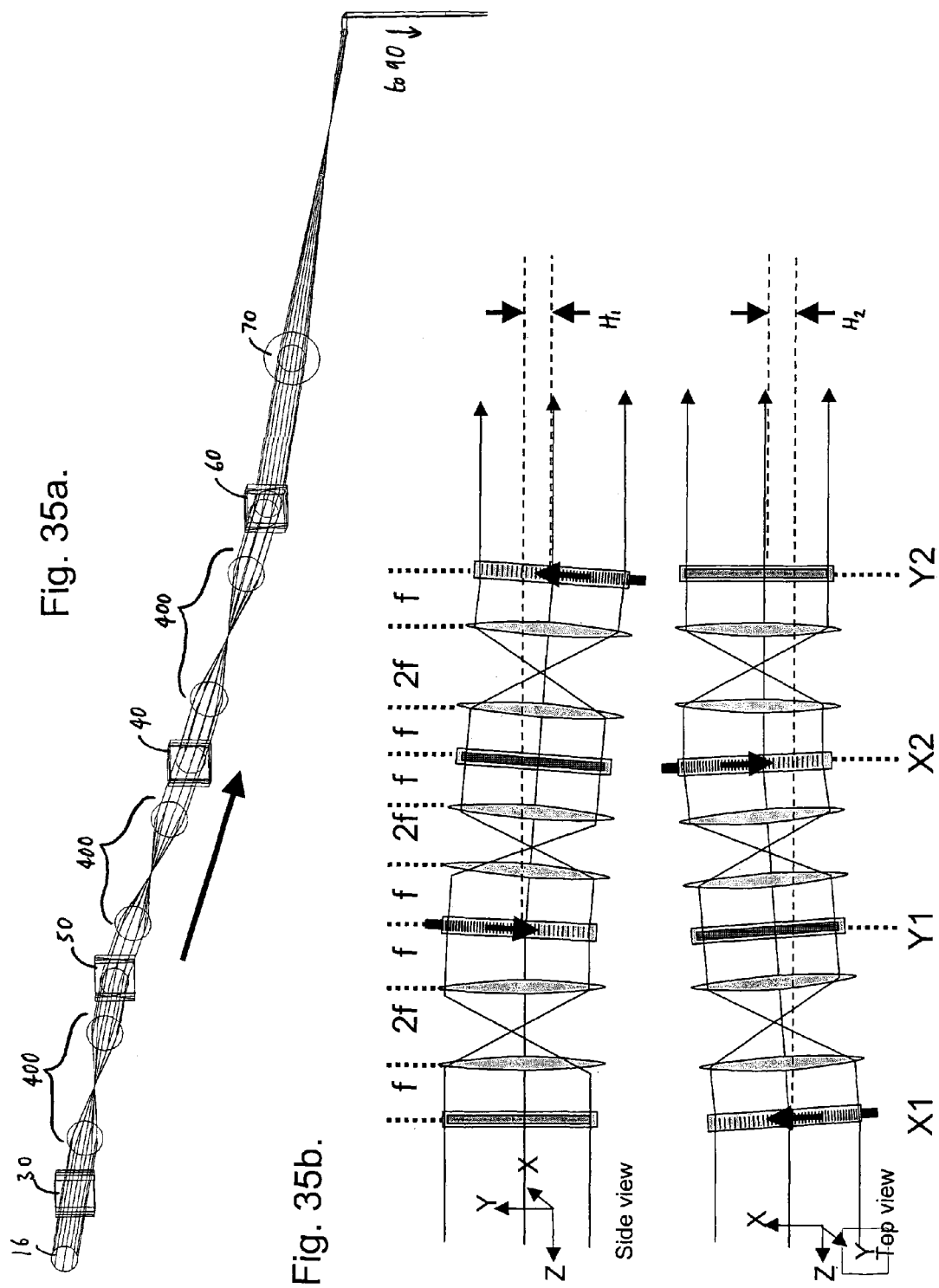
FIGS. 35a and 35b show a practical arrangement of AODs and telecentric relays.

FIGS. 35a and 35b show a typical practical configuration for the four AOD system shown in FIG. 27. As can be seen, each of the AODs 30, 50, 40, 60 is coupled to the subsequent AOD by a telecentric relay 400. Such telecentric relays typically have lengths along the laser path beam of 400 mm or more. As can be seen from FIG. 35b, each telecentric relay has a total length of 4f, where f is the focal length of one relay lens. Typically f=100 mm. Accordingly, the requirement to utilise at least three telecentric relays to couple the AODs together adds 1.2 m to the total beam length of the system. As explained above, different wavelengths of light are diffracted by different amounts. Accordingly, when the laser wavelength is changed, the AODs and telecentric relays have to be repositioned. FIG. 35b shows two displacements $H_1$ and $H_2$. These are the displacements of the output beam centre line compared to the input beam centre line. This displacement varies with the wavelength of light. With a wavelength λ=700 nm, this displacement is approximately 32 mm. With a wavelength of λ=900 nm, this displacement is approximately 40 mm. Consequently, when changing the laser wavelength from 700 nm to 900 nm, the optical components have to be realigned by 8 mm. Such realignment is a necessary consequence of utilising telecentric relays. Accordingly, telecentric relays are not ideal in a system for which it is intended to change the laser wavelength frequently. This aspect of the invention thus provides a means for dispensing with the telecentric relays and thus allows a more compact and configurable system to be provided.

The telecentric relays provided in the prior art are necessary to couple together the AODs appropriately. As shown in FIG. 8, the first AOD modulates the input laser beam 16 to be a laser beam 18 having a curved wavefront. This wavefront is moving at the speed of sound in the X direction. The second AOD modulates the incoming laser beam 18 to be a laser beam 28 with a curved wavefront. The curvature here will be equal to the sum of the curvature brought about by the first AOD added to the curvature brought about by the second AOD. The resulting focal position 22 will only be stationary if the curvature endowed on the laser beam by the second AOD equals that of the wavefront as it enters the second AOD. In the absence of the second AOD, it is apparent from FIG. 8 that the curvature of the laser beam 18 increases as you move further away from the first AOD. When the AODs are set up to endow an incoming laser beam with the same curvature (i.e. the AODs are set up with the same ramp rates), it is thus necessary to either place the AODs extremely close together or to telecentrically relay the output of one AOD to the input of the next AOD.

This aspect of the present invention is based on the realisation that the AODs 30, 40 can be excited with different acoustic waves so as to allow realistic practical separations between the AODs without the requirement of a telecentric relay. The acoustic waves can be modified either to allow the generation of a completely stationary focal position 22 or precisely controlled scanning.

Figure 36:
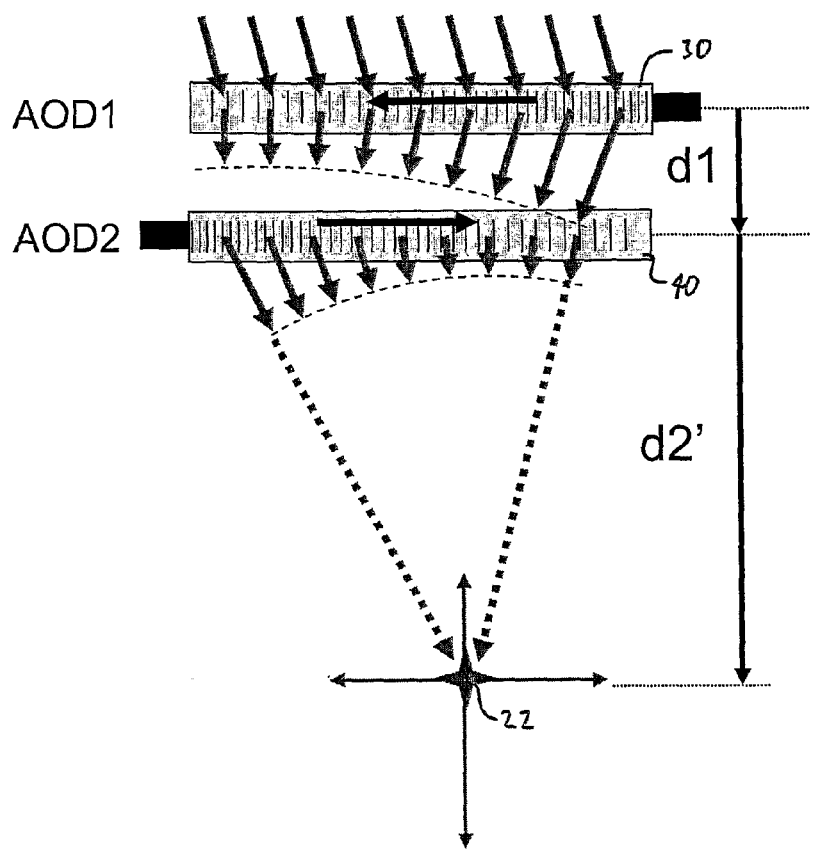
FIG. 36 shows a laser beam being focussed by two AODs.

In FIG. 36, $d_1$ is the separation between the first AOD 30 and the second AOD 40 and $d_2'$ is the distance from the second AOD to the focal point 22.

Figure 37:
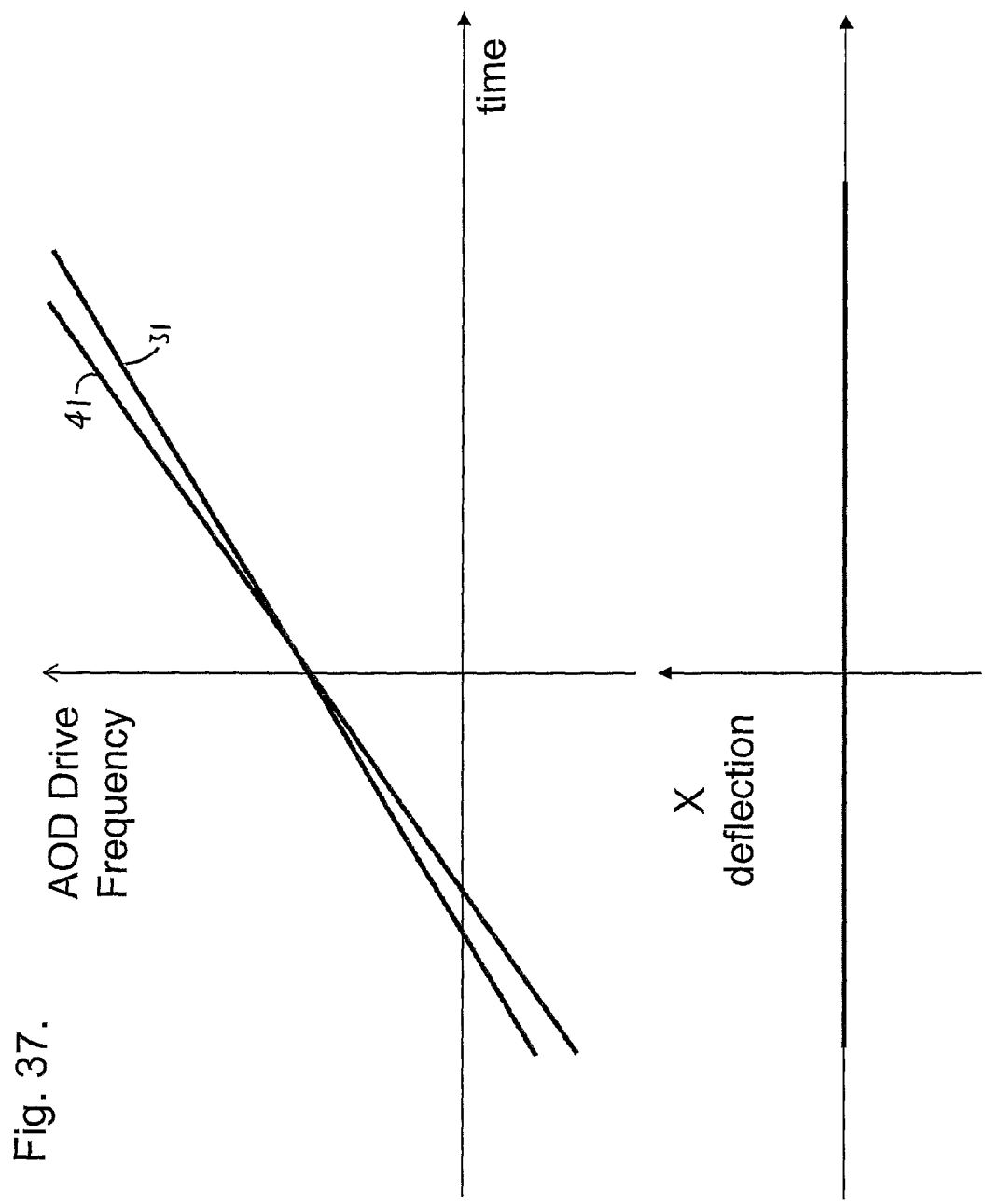
FIG. 37 shows the AOD drive frequencies utilised in the arrangement of FIG. 36.

This aspect of the invention is based on the appreciation that the curvature of the wavefront arriving at the second AOD 40 must exactly match the additional curvature induced by the second AOD 40. As is apparent from FIG. 36, as the distance $d_1$ increases, the curvature of the arriving wavefront increases because the light is converging downwards towards a focus. This is compensated for in the present invention by providing a less rapid ramp (chirp) on the first AOD 30 than on the second AOD 40. This is illustrated in FIG. 37 where it can be seen that the ramp rate $a_1$ for the first AOD 30 is lower than the ramp rate $a_2$ for the second AOD 40 ($a_1$ is equal to the gradient of the line 31 and $a_2$ is equal to the gradient of the line 41). This serves to produce a focal position 22 which is stationary in the X direction, as shown in FIG. 37.

Figure 38:
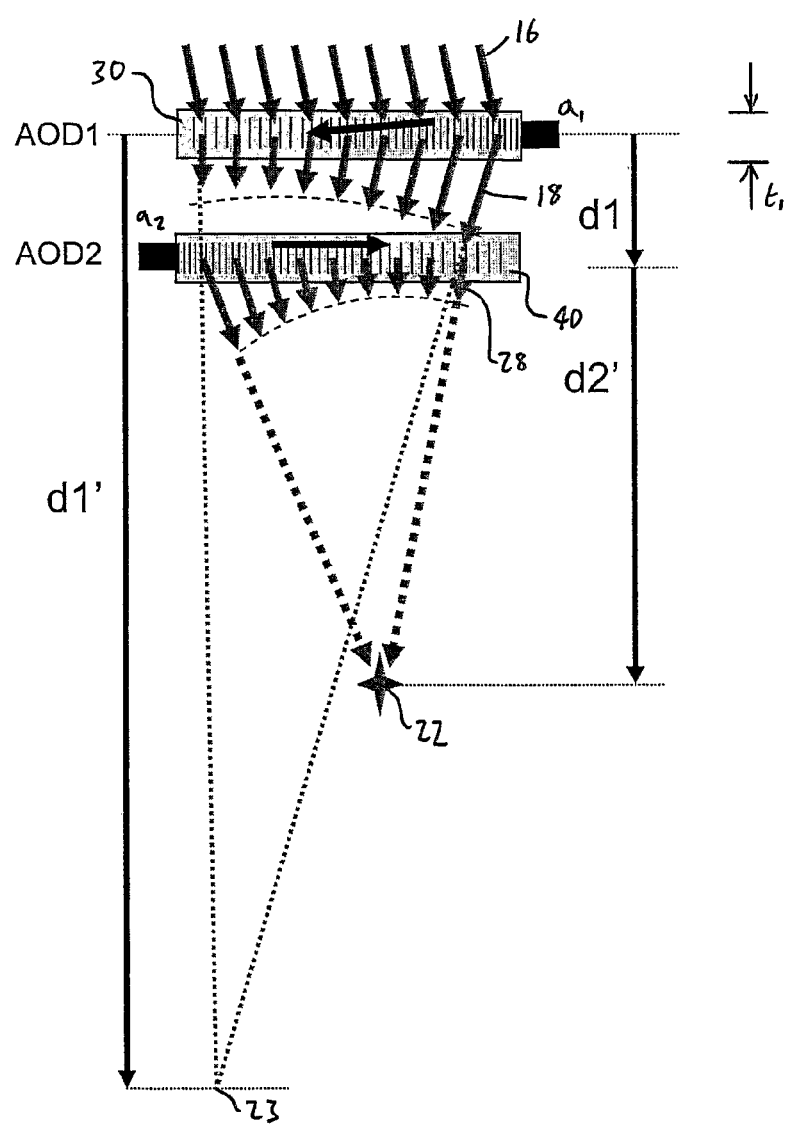
FIG. 38 shows distances used to derive equations to explain the ramp rates used in the AOD configuration of FIG. 36.

Referring to FIG. 38, the first AOD 30 is excited with an acoustic wave having a chirp rate of $a_1$. Accordingly, an incoming laser beam 16 is converted to converging laser beam 18 that is focussed at the point 23 a distance $d_1'$ from the first AOD 30. As is well known, this distance $d_1'$ is given by:

$$d_1' = \frac{V^2}{\lambda a_1} \quad (4)$$

wherein:
V=speed of sound in the AODs (m/s)
$a_1$=ramp rate of first AOD drive (Hz/s)
λ=wavelength of light (m)

It follows from this that the radius of the curvature of the wavefront of the laser beam 18 at the point where it meets the second AOD 40 is given by:

$$d_2' - d_1 \quad (5)$$

In order that the resulting focal position 22 is stationary, the curvature added to the laser beam 18 by the second AOD 40 must equal the curvature of the laser beam 18 as it arrives at the second AOD 40. Accordingly:

$$d_2' = \frac{d_1' - d_1}{2} \quad (6)$$

The factor of 2 appears in this equation because the curvature added by the second AOD 40 is identical to the curvature that already exists at the laser beam 18 as it enters the second AOD 40. The resulting curvature of the laser beam 28 is thus twice the curvature of the laser beam 18. From these equations, it can be deduced that:

$$a_2 = \frac{V^2}{2\lambda d_2'} \quad (7)$$

$$a_1 = \frac{V^2}{\lambda(2d_2' + d_1)} \quad (8)$$

$$\frac{a_1}{a_2} = \frac{2d_2'}{2d_2' + d_1} \quad (9)$$

In these equations, $d_1$ is always a positive value. The values $d_2'$, $a_1$ and $a_2$ are positive for converging rays as shown in FIG. 7a and negative for diverging rays as shown in FIG. 7c. As explained earlier, even when the rays are diverging, a real focal position is achieved using subsequent optics, such as the lens 70.

When equation (9) is studied, it is apparent that if $d_1$ is made to be zero then $a_1$ equals $a_2$. This is the assumption utilised in the prior art because coupling two AODs together with a telecentric relay exactly couples the output of the first AOD onto the input of the second AOD and thus gives an effective separation of the AODs of zero. Up until now, it has always been thought that the frequency chirp across the two AODs ought to be the same and that the effective separation between the AODs should be zero (by virtue of utilising a telecentric relay). The equations derived by the present inventors show that the chirp rate across the two AODs can be made slightly different, in accordance with equation (9), to account for a real separation of $d_1$ between the two AODs, to provide a system which provides a stationary focal position 22 without a telecentric relay between the AODs.

This is achieved by adjusting the ramp rate $a_1$ of the first AOD 30, in accordance with equation (8), to allow for the change in wavefront curvature between the first AOD 30 and the second AOD 40. Preferably, the wavefront curvature arriving at the second AOD 40 equals the additional curvature that is added by the second AOD 40. This "matching of curvature" provides for a stationary focal position.

In the equations and analysis above, the distances are apparent optical thicknesses. If further optical components are interposed between the AODs, such as half wave plates and polarisers, then the apparent optical separation needs to be calculated by taking into account the refractive index of such additional components. Also, the refractive index of the AODs themselves needs to be taken into account. This can be done by assuming that the acoustic wave enters and leaves the AOD at its thickness-midpoint such that the apparent optical distance $d_1$ is equal to the distance in air between the AODs plus half the thickness of the first AOD 30 divided by its refractive index plus half the thickness of the second AOD 40 divided by its refractive index. When the two AODs are identical, then the value $d_1$ equals the distance in air plus the thickness of the AOD divided by its refractive index.

These principles can be extended to a system which utilises four AODs to focus in more dimensions. As discussed above, when two AODs are used, as shown in FIG. 38, the focal position 22 is a line extending perpendicularly out of the page. Four AODs can be utilised to focus in both X and Y to produce a point focal position 22.

Figure 39:
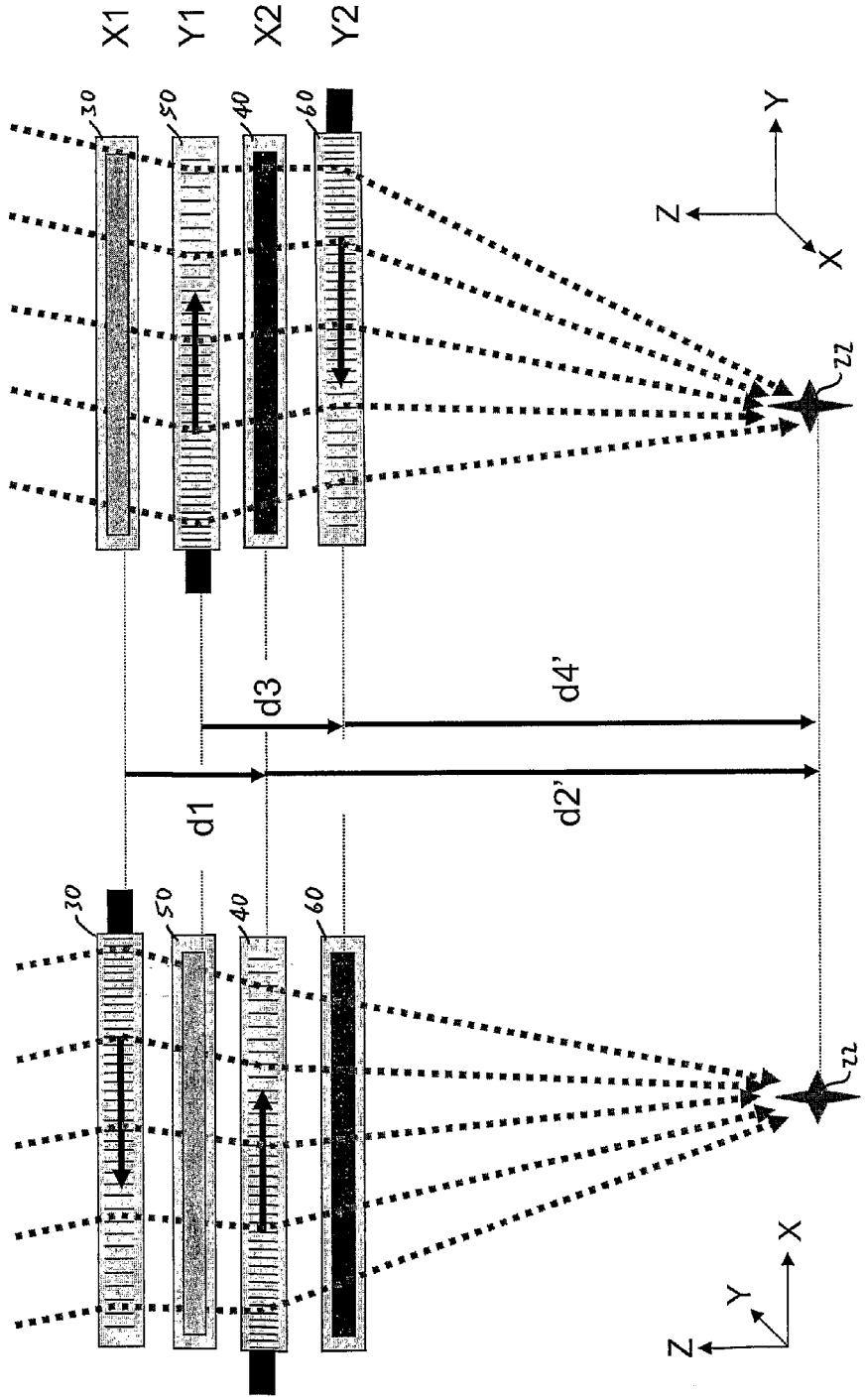
FIGS. 39a and 39b show a configuration of four AODs.

FIGS. 39a and 39b show two orthogonal views of a preferred four AOD system. As in FIG. 38, the first AOD 30 is separated from the second AOD 40 by a distance $d_1$ and the second AOD 40 is a distance $d_2'$ from the focal point 22. In addition, third and fourth AODs 50, 60 are provided, the distance between the third AOD 50 and the fourth AOD 60 being $d_3$ and the distance from the fourth AOD 60 to the focal point 22 being $d_4'$. The ramp rates for the third and fourth AODs can be calculated in a similar way as for the first and second AODs. Very similar equations apply:

$$a_4 = \frac{V^2}{2\lambda d_4'} \quad (10)$$

$$a_3 = \frac{V^2}{\lambda(2d_4' + d_3)} \quad (11)$$

$$\frac{a_3}{a_4} = \frac{2d_4'}{2d_4' + d_3} \quad (12)$$

Accordingly, in the four AOD system, the first and second AODs are stimulated in the same way as the first and second AODs of the two-AOD embodiment. This provides the necessary focussing in the X-Z plane. In addition, third and fourth AODs are stimulated such that the curvature of the wavefront arriving at the fourth AOD equals the additional curvature added by the fourth AOD, hence doubling the curvature of the wavefront as it leaves the fourth AOD. This provides the necessary focussing in the Y-Z plane. The distances $d_2'$ and $d_4'$ are selected to ensure that the final focal spot position 22 is as desired. As will be apparent from FIGS. 39a and 39b, the actual distances between the AODs and the optical thickness of any intervening components, as well as the AODs themselves, needs to be taken into account when determining $d_1$, $d_3$, $d_2'$ and $d_4'$.

Depending on the exact configuration used, further fine tuning may be applied to achieve an exactly stationary spot. The equations above are based on the simplified assumption of AOD crystals having surfaces that are approximately perpendicular to the direction of propagation of the light. It is possible to manufacture the AODs with slightly angled faces (and there are practical reasons to do exactly this) and this can cause errors in the separations used in the equations that can result in a small residual movement of the focal position. These residual movements can be corrected by small adjustments to the ratio of ramp rates $a_1/a_2$, $a_2/a_4$. These corrections can either be found experimentally or by building an accurate optical model using a commercial programme like Zemax. When such angled faces are used, typical corrections are much less than +/-2% to the ramp rate of each AOD. Similarly, small corrections may be applied to the ratio of the X ramp rate to the Y ramp rate to fine tune the astigmatism of the focal position 22. This is equivalent to adjusting the ratio of $d_2'$ to $d_4'$ so that the Z value of the focal position in the X-Z and X-Y planes is the same. These fine tuning corrections are a function of the Z position of the focal spot and can readily be built into the algorithms that compute the ramp rate of the AODs before each scan.

As will be understood from the above, it is possible with the present invention to utilise two or four AODs to achieve a completely stationary focal line or focal point inside or on a target. This can achieved without lengthy telecentric relays between the AODs by appropriate manipulation of the ramp rates of the acoustic waves applied to the AODs. The resulting system can thus be used to achieve random access focussing at very fast speeds. For example, it is possible to repetitively focus to 30 different positions within or on the target at a frequency of 1000 Hz. In other words, in one second, the laser beam can be focussed to 30 points one thousand times. To achieve this, the laser beam focal point is repositioned 30,000 times in one second. This is simply not achievable with prior art galvanometer mirrors.

Scanning a Target

To build up a three-dimensional image of a target, it is useful to be able to follow a raster scan with the focal point along a predetermined path through the target. One potential raster scan is to move the focal point in the X direction, keeping the Y and Z values constant, to then increment the Y position by some small amount, to perform another scan in the X direction and so on until a two-dimensional grid of scans is achieved. Thereafter, the Z direction is incremented and another two-dimensional grid is scanned until a three dimensional volume has been built up. This can be done quite quickly with the system of the present invention such that a three-dimensional image can be provided.

One problem encountered when implementing a raster scan using the system of the present invention is that there are minimum and maximum limits on the frequency of acoustic waves that can be put through the AODs. This is illustrated as $f_{max}$ and $f_{min}$ in FIG. 4a, for example. Typical values are 30 Mhz for the minimum frequency and 40 Mhz for the maximum frequency. As shown in FIG. 4a, there will be a "flyback" portion whereby the frequency is suddenly switched from the maximum frequency to a lower frequency (in the case of applying a positive chirp rate) or a sudden switch from the minimum frequency to a higher frequency (in the case when applying a negative chirp rate). The X, Y and Z positions depend on the chirp rate and the difference in absolute frequencies between the first and second AODs (see FIG. 8). Accordingly, this sudden changing of the absolute values of both frequencies will not cause a movement in the X Y and Z position of the focal spot if it is implemented properly.

If desired, the X and Y scans can be carried out simultaneously with the Y scan being much slower than the X scan. This leads to the two-dimensional scanning pattern shown in FIG. 40.

Figure 41:
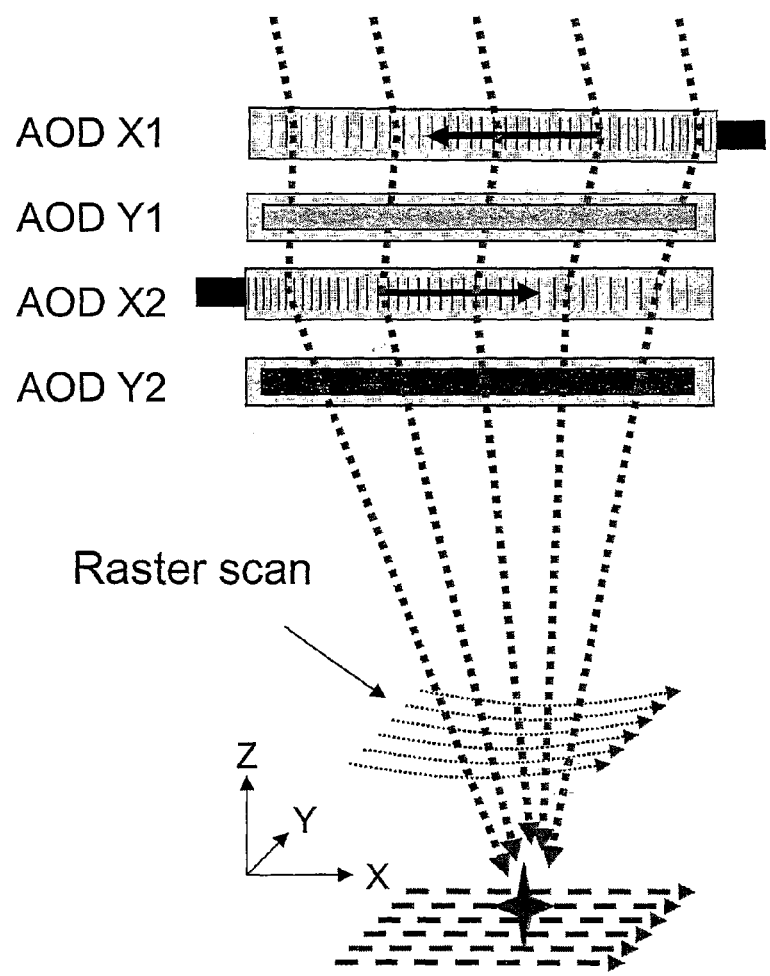
FIG. 41 shows raster scanning with four AODs.

FIG. 41 shows how a raster scan performed in the X-Y plane can be achieved. Movements in X or Y correspond to changes in the angle of the output laser beam from the AOD system.

Figure 42:
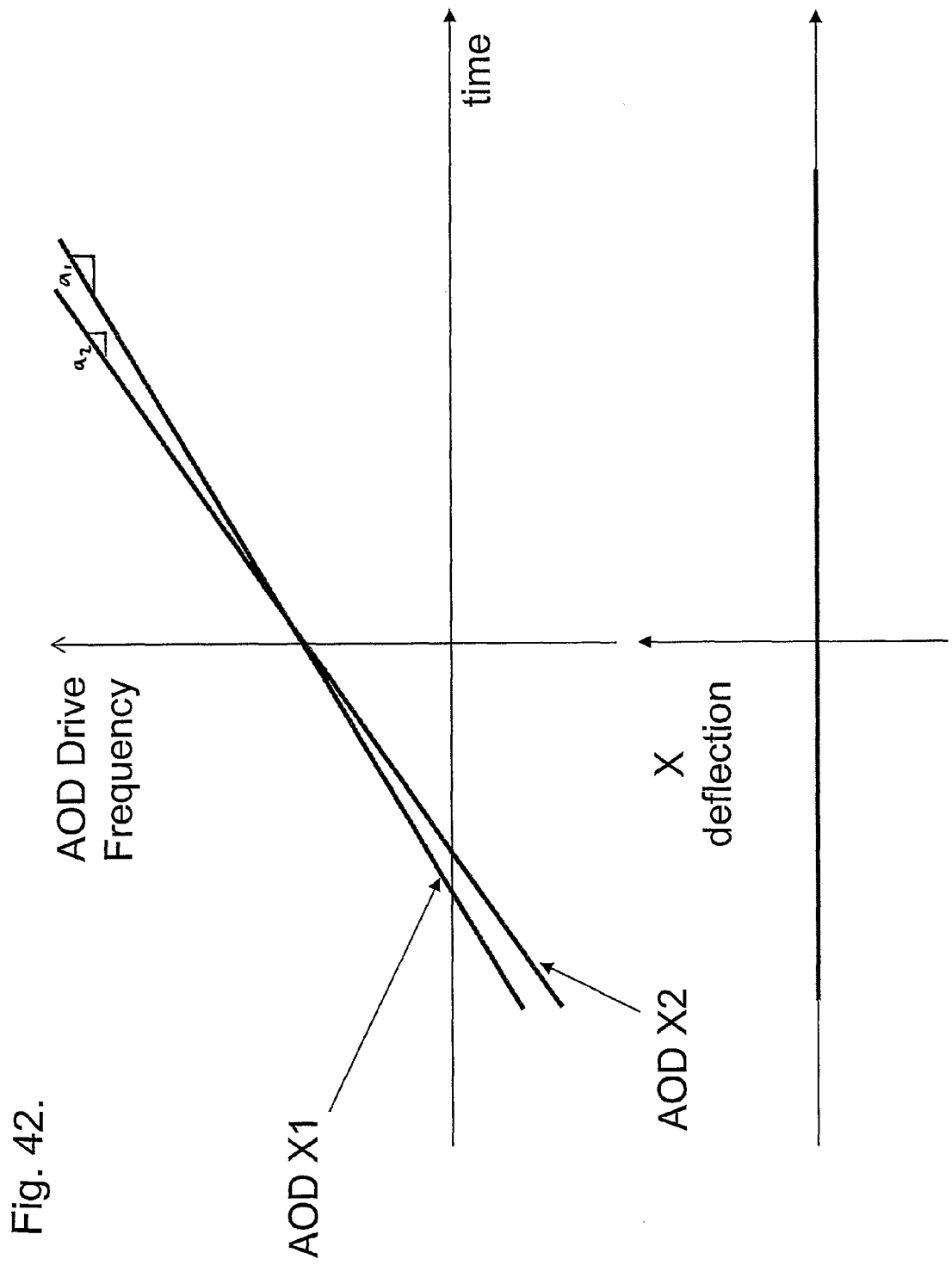
FIG. 42 shows the frequency applied to two AODs in order to focus to a stationary spot.
Figure 43:
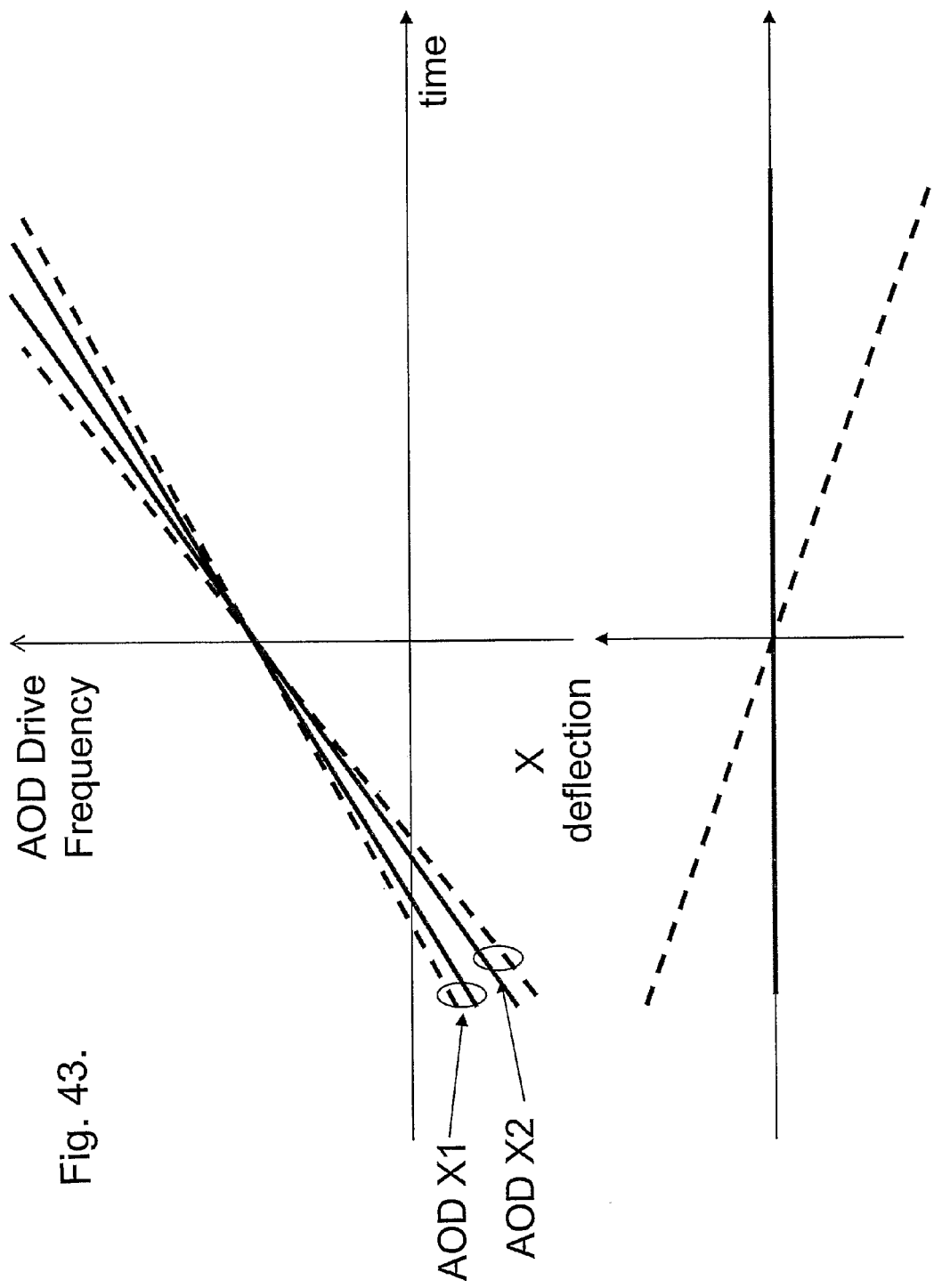
FIG. 43 shows how these frequencies need to be changed in order to provide a scanning X deflection.

As is apparent from the above equations and from FIG. 42, to focus a stationary spot at X=0 requires $a_2$ to be slightly larger than $a_1$ in accordance with equation (9). The situation shown in FIGS. 41 and 42 is where the focal position has a positive value of Z such that the laser beam converges upon exiting the AOD system. In order to provide an X deflection that moves at some constant linear velocity, it becomes necessary to vary $a_1$ and $a_2$ such that there is a linearly increasing difference between the absolute frequency of the acoustic wave in the first AOD and the absolute value of the frequency in the second AOD. This is illustrated in FIG. 43 where the dotted lines show $a_1$ being reduced and $a_2$ being increased. This provides a scanning X deflection whereby the X value of the focal point decreases linearly with time as shown in the lower part of FIG. 43.

Figure 44:
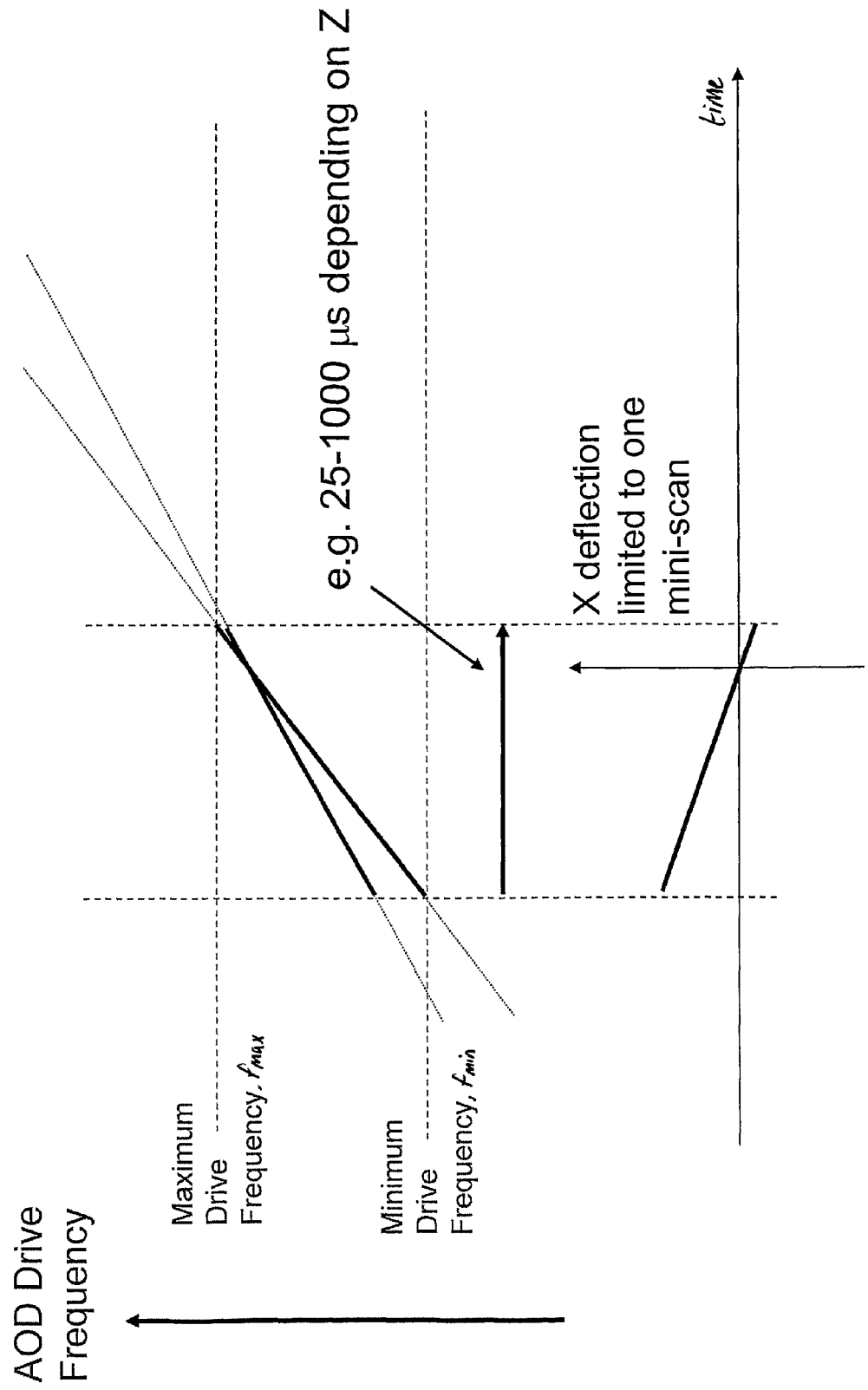
FIG. 44 shows how the maximum and minimum drive frequencies in the AODs limit the scan time.

As shown in FIG. 8, varying the slope $a_1$, $a_2$ of the ramps varies the Z position. For Z =0, $a_1$ and $a_2$=0 and X scanning can easily be achieved by making $a_1$ slightly negative and $a_2$ slightly positive. For other values of Z, higher magnitudes of $a_1$ and $a_2$ are required and the limits on the minimum and maximum drive frequencies of the AODs mean that it is possible to hit one of the limits very quickly. For non-zero values of Z, it is possible to hit either the minimum or maximum drive frequency before one has completed an X scan across the target. In such cases, it is convenient to perform a series of X "mini-scans" in which the X scan as a whole is interrupted at various points in time to allow the frequency to be reset in a "flyback" period. This is illustrated in FIG. 44, which is a cropped version of FIG. 42 showing how the maximum and minimum drive frequencies limit the amount of X deflection that can take place.

Figure 45:
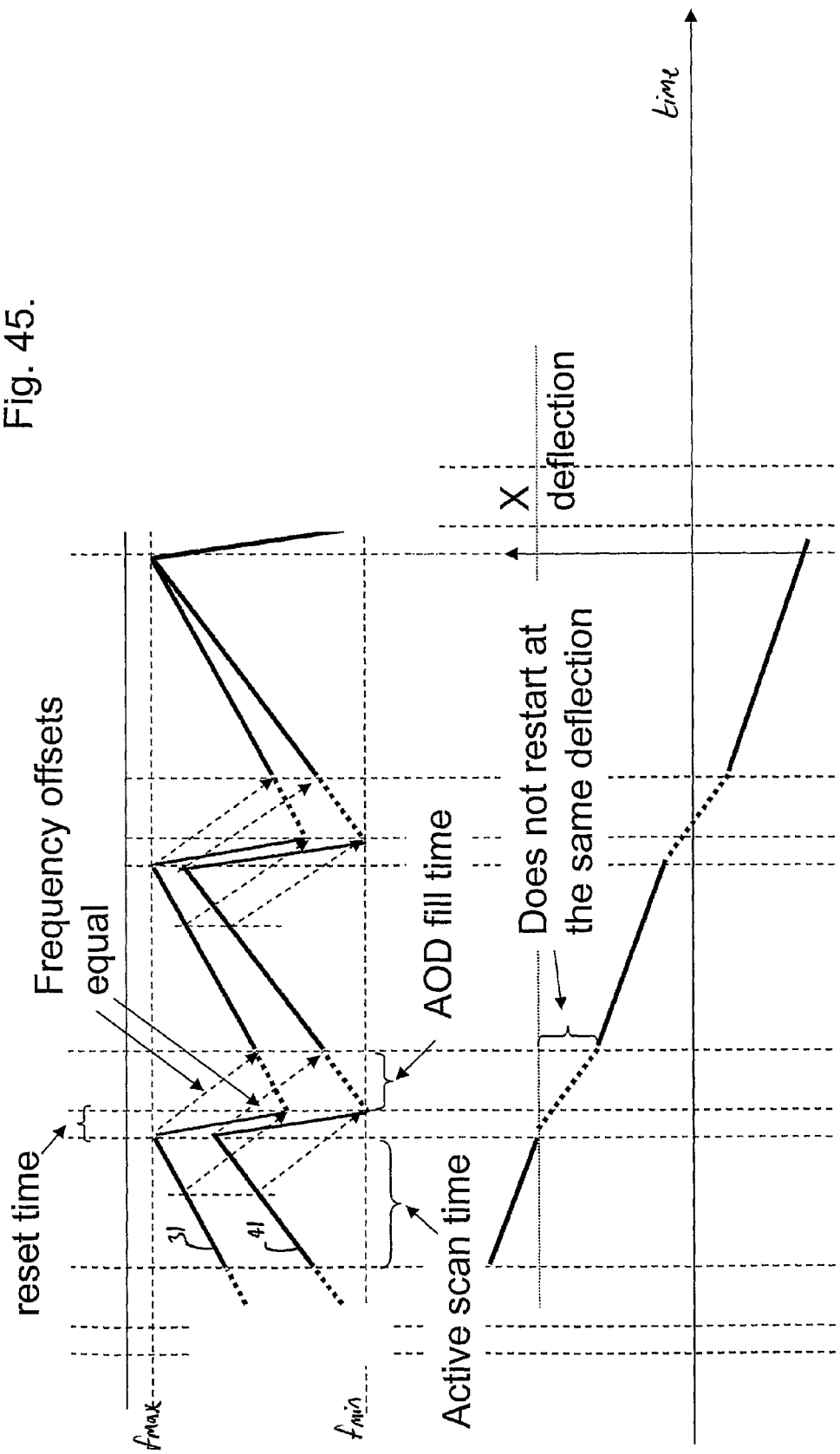
FIG. 45 shows a series of mini scans in X.

FIG. 45 illustrates a series of mini-scans in X. The frequency of the acoustic wave in the first AOD 30 is designated by line 31 and the frequency of the acoustic wave in the second AOD 40 is designated by the line 41. In this example, line 31 has a shallower gradient than line 41 which means that $a_1$ is less than $a_2$, which from equation (9) means that $d_2'$ is positive, which in turn means that this situation is for some positive value of Z. As shown in FIG. 45, when the absolute value of the frequency of the acoustic wave in the first AOD 30 reaches the maximum value $f_{max}$ it becomes necessary to reset the frequencies. As is apparent from FIG. 45, it will not be possible to change the frequency in the first AOD 30 to be $f_{min}$ because the frequency in the second AOD 40 must be less than the frequency in the first AOD 30 to ensure that the difference in frequencies between the two AODs continues to give the correct value of X. Accordingly, the frequency in the second AOD 40 is reduced to $f_{min}$ and the frequency in the first AOD 30 is reduced by the same amount. This frequency resetting takes place in a period of non-active time when the laser is switched off (or at least when measurements are not recorded or are ignored). The non-active time generally has two components. The first component, known as the "reset time" is the time it takes to reset the frequency from the maximum value to the new value or from the minimum value to the new value. This is typically 4 µs. The second component, known as the "AOD fill time" is the time it takes to fill the AOD with appropriate acoustic waves. This is typically equal to the width of the AOD divided by the speed of the acoustic wave in the AOD. For example, if the AOD is 15 mm wide and the acoustic waves travel at 600 m/s, then the AOD fill time will be 25 microseconds. The total non-active time is thus typically around 30 µs.

After the AOD fill time has elapsed, the frequencies in the AODs should be different by an amount equal to the difference at the end of the previous mini-scan. As the frequencies are different by the same amount, it might be expected that the X position would be the same at the beginning of the second mini-scan as it was at the end of the first mini-scan. This is true when the AODs are telecentrically relayed. However, it has been found that this is not the case when there is some separation between the AODs. Instead, the X position is different to that which is expected as shown in FIG. 45, bottom graph. There it can be seen that the X position is different at the start of the second mini-scan than at the end of the first mini-scan.

Figure 46:
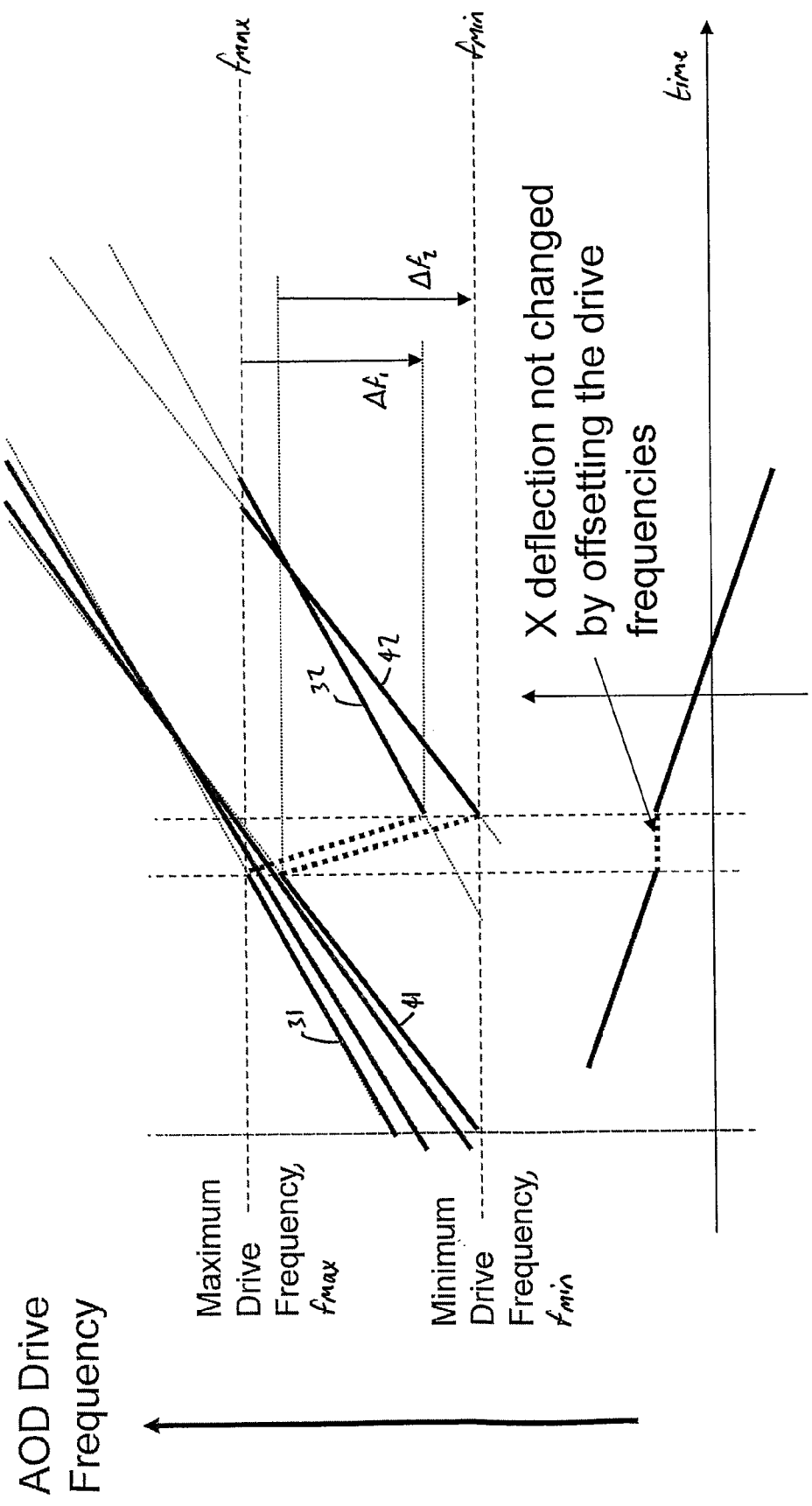
FIG. 46 shows frequency offsets being applied between mini scans.

The present inventors have found that the reason for this lies in the assumption that the separation of the ramps alone causes the variation in X. This assumption is only true if there is no physical separation between the AODs, or alternatively, if the AODs are coupled by telecentric relays. In the case where there is an actual separation between the AODs, a more complicated algorithm needs to be utilised to calculate the frequency offsets necessary to maintain the position in X between the end of one mini-scan and the start of the next mini-scan. In FIG. 45, the frequency offsets are calculated by making the frequency in the second AOD zero and reducing the frequency in the first AOD by some amount that causes the frequency difference to be the same at the start of the next mini-scan. In fact, different offsets will be needed for each AOD as illustrated in FIG. 46. Here, the frequency in the first AOD is reduced by $\Delta f_1$ and the frequency in the second AOD is reduced by $\Delta f_2$. This second frequency reduction, $\Delta f_2$ is calculated as the offset needed to reduce the frequency in the second AOD to $f_{min}$. It has been found that $\Delta f_1$ and $\Delta f_2$ are related by the following equation:

$$\frac{\Delta f_2}{\Delta f_1} \approx \frac{d_1'}{d_1' - d_1} \quad (13)$$

Figure 47:
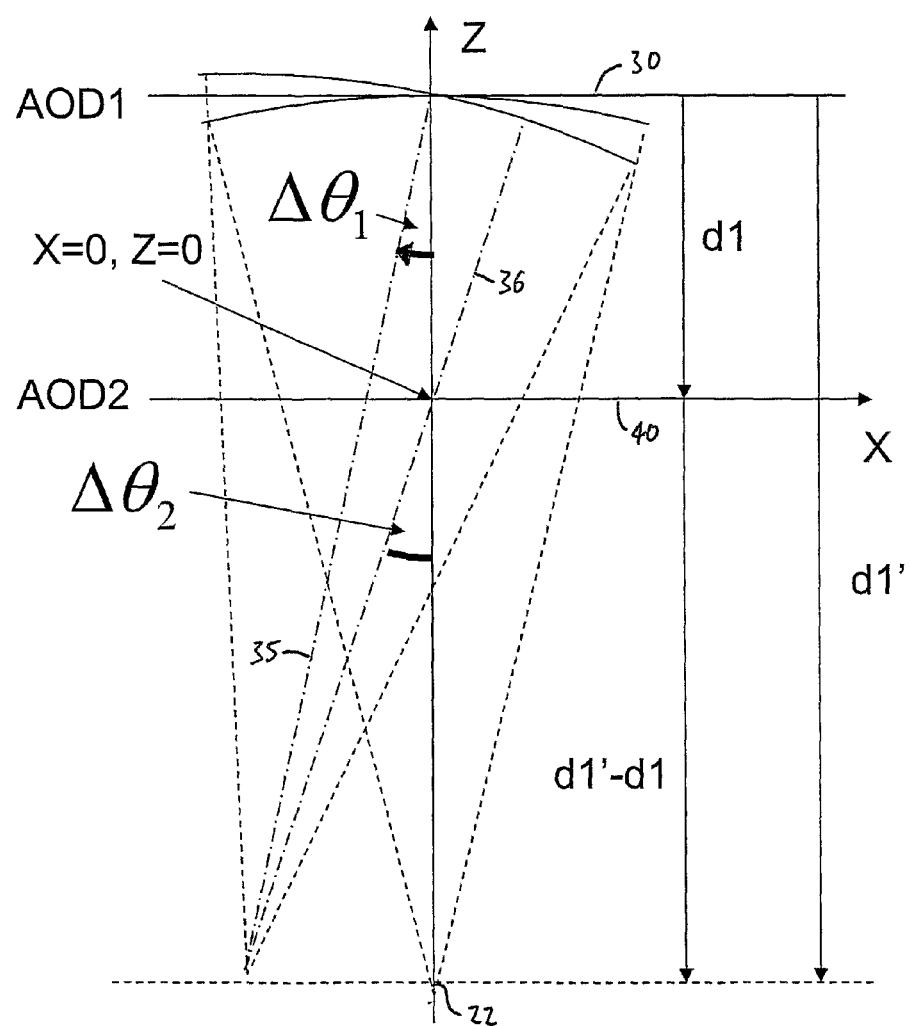
FIG. 47 shows a geometric derivation useful in determining the frequency offsets.

This equation can be proved by referring to FIG. 47. The centre line of the first AOD is referenced 30 and the centre line of the second AOD is referenced 40. The ultimate focal point is shown at 22. If a frequency offset is introduced into the acoustic wave of the first AOD this will produce an angular deflection of $\Delta\theta_1$ at the central position (X=0) of the AOD. This is graphically illustrated in FIG. 47 by the angle $\Delta\theta_1$ between the line of the laser beam before deflection (vertically downward in FIG. 47) and the line 35 of the laser beam after deflection. However, at the second AOD, at the position X=0 the ray will apparently be deflected by a different angle $\Delta\theta_2$. As is apparent from FIG. 47, $\Delta\theta_2$ is larger than $\Delta\theta_1$. A geometric deduction leads to the equation (which is valid for all small angles of $\Delta\theta_1$ and $\Delta\theta_2$):

$$\frac{\Delta\theta_2}{\Delta\theta_1} \approx \frac{d_1'}{d_1' - d_1} \quad (14)$$

Equation (14) is derived once it is realised that the change in angles of the beam is directly proportional to the change in frequency. As shown in the lower part of FIG. 46, applying offsets that have the relationship of equation (13) means that the X deflection is not changed between the end of one mini-scan and the beginning of the next mini-scan. Please note that FIG. 46 does not show any AOD fill time for clarity although there will in reality be an AOD fill time as shown in FIG. 45. In practice, $\Delta f_1$ and $\Delta f_2$ are calculated to be correct at the end of the AOD fill time, when the data collection restarts. Converting equation (13) to the nomenclature of FIGS. 39a and 39b, we find:

$$\frac{\Delta f_1}{\Delta f_2} = \frac{2d_2'}{2d_2' + d_1} \quad (15)$$

Similarly, when there are four AODs present:

$$\frac{\Delta f_3}{\Delta f_4} = \frac{2d_4'}{2d_4' - d_3} \quad (16)$$

The scan rate $\delta\theta/\delta t$ can be calculated as follows:

For the simple case where the AODs are coupled by telecentric relays (i.e. $d_1$ is considered to be zero) the scan rate is proportional to the difference in slopes of the chirp signal provided to each AOD. In fact, the scan rate is given by:

$$\frac{\delta\theta}{\delta t} = \frac{\lambda}{V}(a_1 - a_2) \quad (17)$$

In the simple case of $d_1=0$, the following equations result for the ramp rates $a_2$ and $a_1$.

$$a_2 = \frac{V^2}{2\lambda d_2'} + \frac{V}{2\lambda}\frac{\delta\theta}{\delta t} \quad (18)$$

$$a_1 = \frac{V^2}{2\lambda d_2'} - \frac{V}{2\lambda}\frac{\delta\theta}{\delta t} \quad (19)$$

It can be seen from these equations that the ramp rate $a_2$ is increased by the same amount that the ramp rate $a_1$ is decreased. This, however, only applies when $d_1$ is considered to be zero (i.e. when the AODs are telecentrically coupled). In the more complicated case when $d_1$ is non-zero. The values for $a_1$ and $a_2$ are instead given by:

$$a_1 = \frac{\frac{V}{\lambda}\left(\frac{V}{d_2'} - \frac{\delta\theta}{\delta t}\right)}{\left(2 + \frac{d_1}{d_2'} - \frac{d_1}{V}\frac{\delta\theta}{\delta t}\right)} \quad (20)$$

$$a_2 = \frac{V^2}{2\lambda d_2'} + \frac{V}{2\lambda}\frac{\delta\theta}{\delta t} \quad (21)$$

Figure 48:
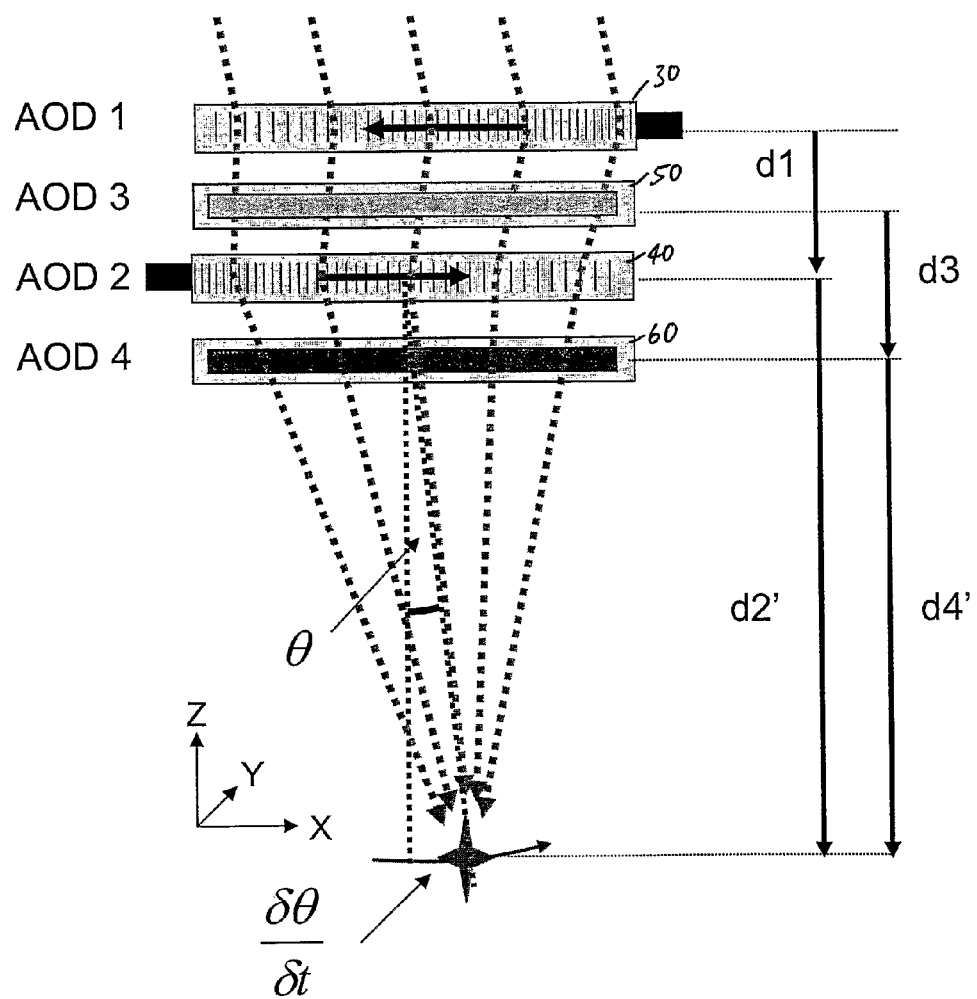
FIG. 48 shows a four AOD system for providing a constant change of scan angle θ in the X-Y plane with time.

These equations apply where there are two AODs for focussing in the X-Z plane or, as shown in FIG. 48, when there are four AODs. In this case, the angular scan rate $\delta\theta/\delta t$ is that measured about the second AOD 40. The apparent rate as measured about the last AOD 60 can be obtained y multiplying this scan rate by $d_2'/d_4'$.

Figure 49:
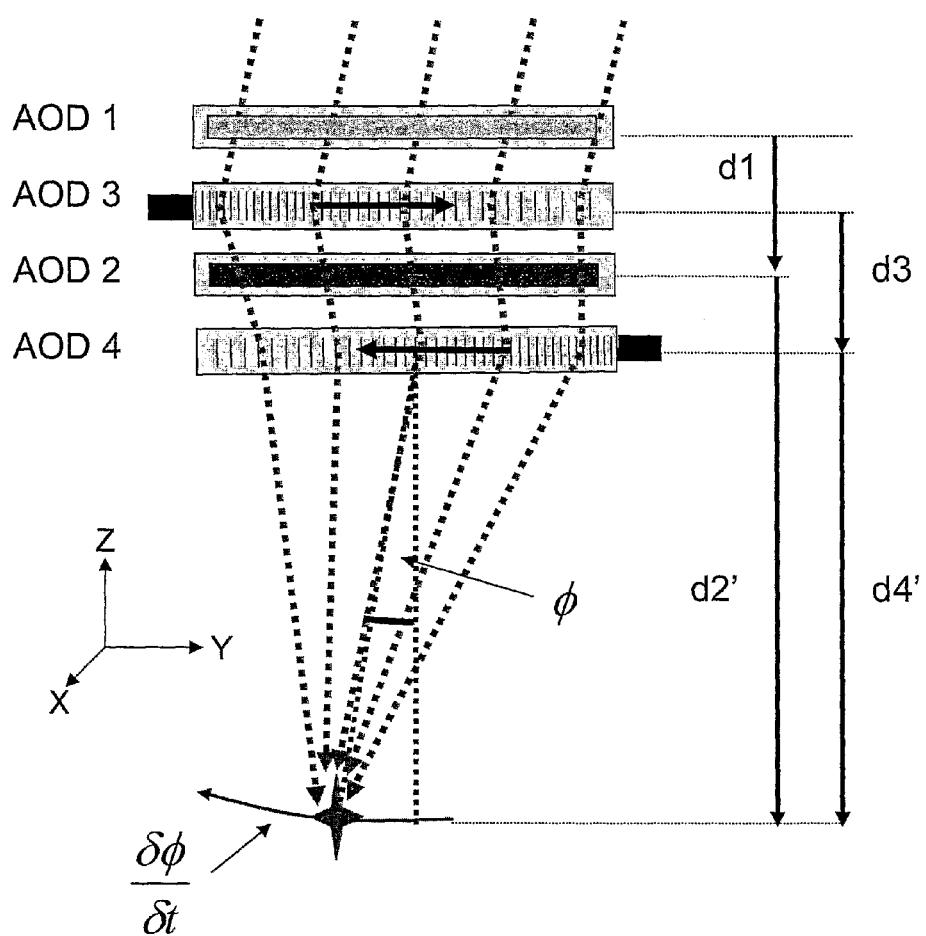
FIG. 49 shows the four AOD system, in which a constant change of scan angle φ is provided in the Y-Z plane.

FIG. 49 shows the appropriate equations for the Y-Z plane. Here, $\Phi$ is the angle as measured from the fourth AOD 60.

$$a_3 = \frac{\frac{V}{\lambda}\left(\frac{V}{d_4'} - \frac{\delta\phi}{\delta t}\right)}{\left(2 + \frac{d_3}{d_4'} + \frac{V}{2\lambda}\frac{\delta\theta}{\delta t}\right)} \quad (22)$$

$$a_4 = \frac{V^2}{2\lambda d_4'} + \frac{V}{2\lambda}\frac{\delta\theta}{\delta t} \quad (23)$$

As will be appreciated from FIGS. 39a and 39b, the spacing between each adjacent AOD is related to the distances $d_1$, $d_3$, $d_2'$ and $d_4'$ by the following equations:

The effective separation between the first AOD 30 and the third AOD 50 is:

$d_1+d_2'-d_3-d_4'$

The effective separation between the third AOD 50 and the second AOD 40 is:

$d_3+d_4'-d_2'$

The effective separation between the second AOD 40 and the fourth AOD 60 is:

$d_2'-d_4'$

Multi-Wavelength System

FIGS. 20 to 23 above show the possibility of varying the compensation factor C to either fully compensate for chromatic aberration in the Z-plane (FIG. 23), to fully compensate for chromatic aberration in the Z and Y planes (FIG. 22) or to achieve some intermediate compensation in which chromatic aberration is compensated in all planes, but not for the maximum extent (FIG. 20). In order to vary this compensation factor C, it is necessary to vary the strength of the lenses used in the telecentric relay. For example, the lenses 110 and 150 in FIG. 17 can be replaced with more strongly or less strongly dispersive lenses in order to vary the compensation factor C. In any practical embodiment of a system, it would be beneficial to design into the system a method for varying the compensation factor C, which does not involve having to physically replace lenses.

Another problem lies in the fact that it is desirable for most neuroscience applications to be able to select the wavelength of electromagnetic radiation that is used. Typically, wavelengths of 690 to 1000 nm are used in neuroscience applications. Changing the wavelength of a laser beam passing through diffractive optics automatically changes the deflection angles introduced by such diffractive optics (because the deflection angle is proportional to the wavelength). Accordingly, while it is straightforward to design a system that can operate at a single laser wavelength, it is more difficult to design a system that can operate across a range of wavelengths.

One possible approach is to design the system to operate at the maximum wavelength (e.g. 1000 nm). In such a system, the maximum diffraction angles would be catered for and it can be ensured that no light is lost by light being diffracted through a greater angle than designed. The serious drawback of such a system is that the system inherently works non-optimally for any wavelength less than 1000 nm. In particular, due to the smaller deflection angles, the aperture of the objective lens will not be filled when wavelengths of less than 1000 nm are used and this seriously reduces the amount of power that can be introduced to the target at the focal position.

It would be desirable to design a system in which the electromagnetic radiation wavelength can be varied without influencing the amount of power delivered to the target or the intensity of the focus provided.

Figure 50:
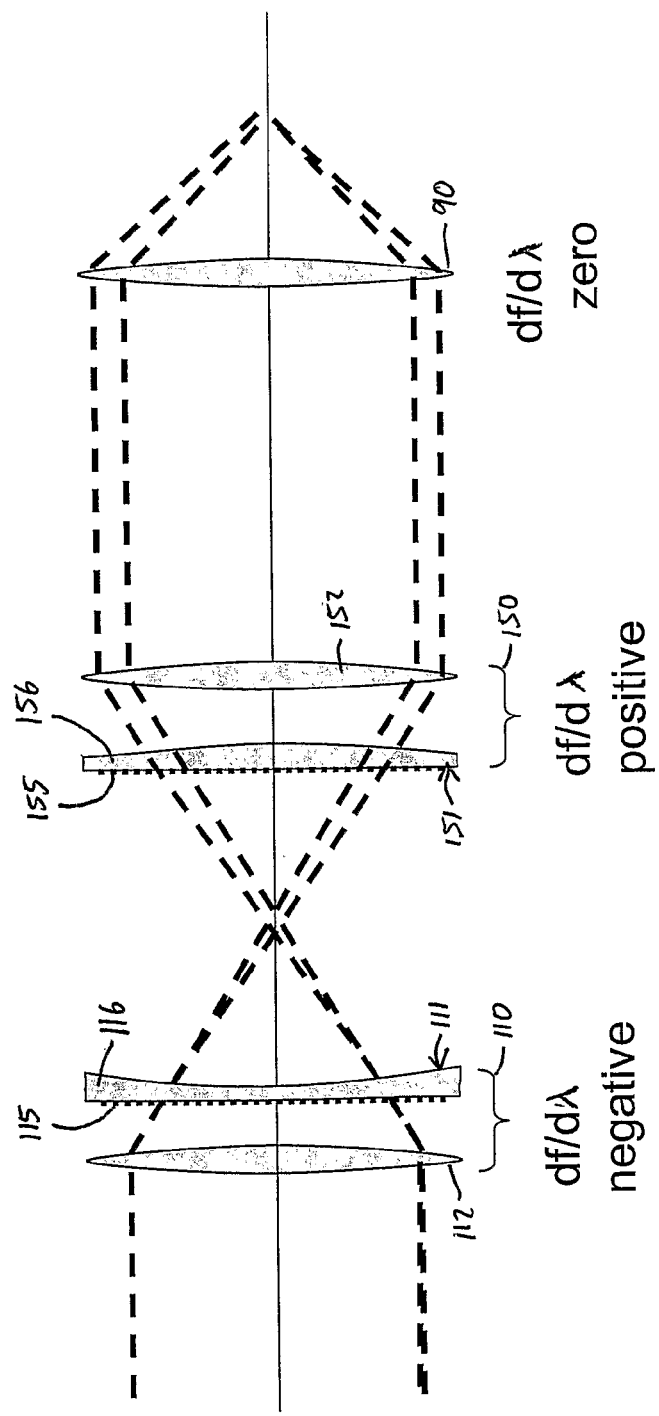
FIG. 50 shows an embodiment of apparatus for correcting chromatic aberration.

FIG. 50 shows one embodiment of the system shown in FIG. 17. Here, the first optical element 110 is provided by a lens 112 having a positive focal power and a compensation plate 111. The second optical element 150 is provided by a lens 152 having a positive focal power and a second compensation plate 151. Compensation plate 111 is comprised of a positive focal length diffractive optical element 115 intimately attached (e.g. glued) onto the plane surface of a negative focal length conventional lens. Compensation plate 151 is comprised of a negative focal length diffractive optical element 155 intimately attached (e.g. glued) onto the plane surface of a positive focal length conventional lens 156. Accordingly, the combined effect of compensation plate 111 and lens 112 is to have dF/dλ negative and the combined effect of compensation plate 151 and lens 152 is to have dF/dλ positive.

Figure 51A:
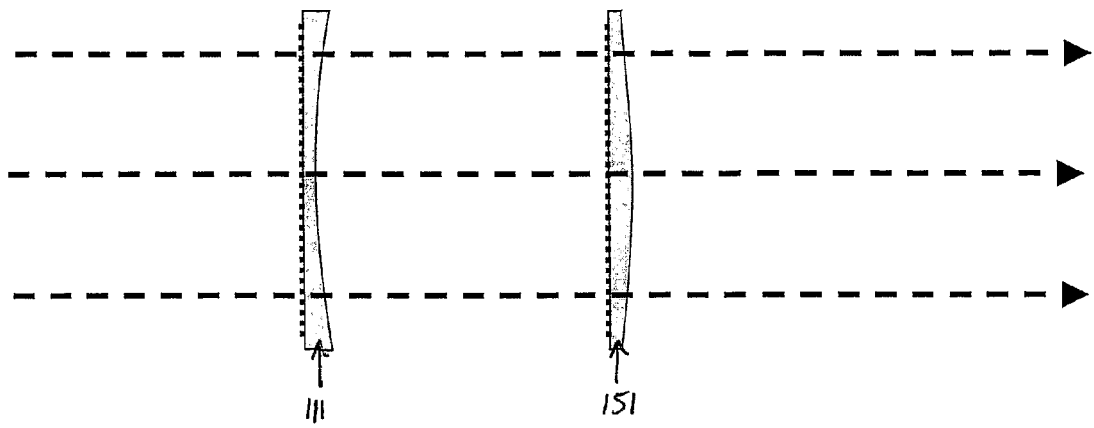
FIGS. 51a to 51c show how diffractive optical elements modulate a beam width in accordance with the wavelength of the beam.
Figure 51B:
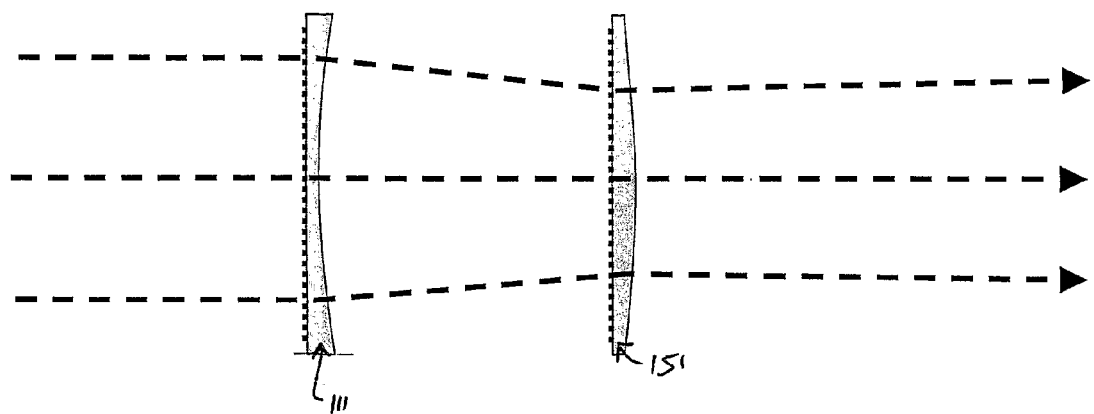
Figure 51C:
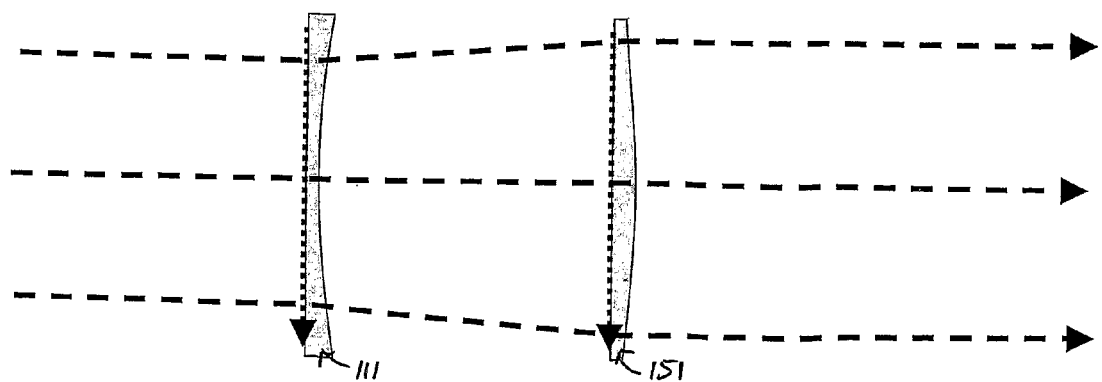

The lenses 112 and 152 have approximately the same effect on all wavelengths of light. Accordingly, virtually all of the chromatic aberration correction is achieved by the compensation plates 111 and 151. FIGS. 51*a* to 51*c* show the effect of changing the laser wavelength on the chromatic aberration correction of the compensation plates 111 and 151.

At the design centre wavelength, as shown in FIG. 51*a*, each compensation plate 111 and 151 provides no overall lensing effect. This is because at this wavelength, the focal length of the diffractive optical elements 115, 155 is exactly equal and opposite to the focal length of the attached lens 116, 156. Accordingly, light at the design wavelength passes through the compensation plates like a flat glass plate.

As the wavelength of laser light is increased from the design wavelength, the diffractive optical elements 115, 155 become stronger (the diffraction angle is proportional to the wavelength) so as to produce a lensing effect as shown in FIG. 51*b*.

At wavelengths less than the design wavelength, the diffractive optical elements become weaker, producing the lensing effect shown in FIG. 51*c*. It is apparent from FIGS. 51*a*-51*c* that the diameter of the output laser beam will be influenced by the centre wavelength of the laser, due to the varying lensing effect of the diffractive optical elements 115, 155.

Figure 52:
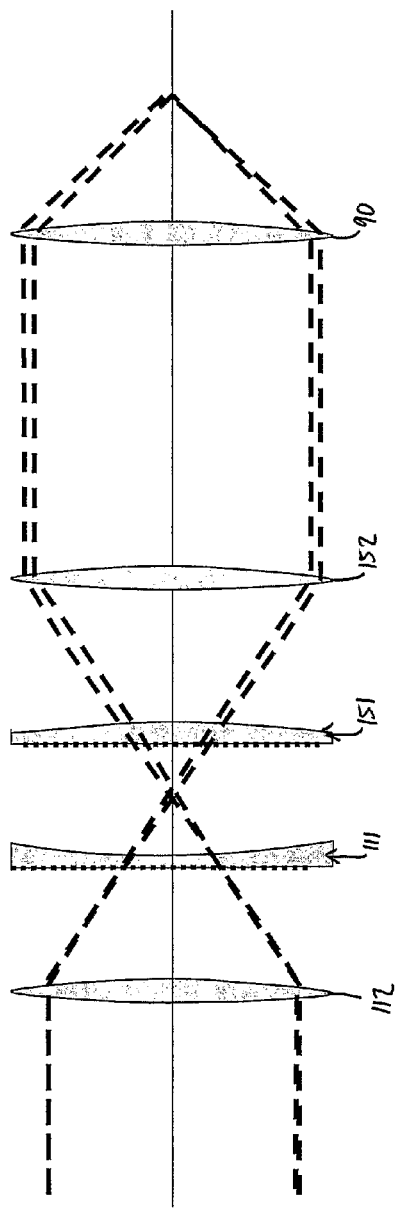
FIG. 52 shows the embodiment of FIG. 50 with the diffractive optical elements axially moved.

One advantage of the arrangement shown in FIG. 50 is that the positions of the compensation plates 111, 151 can be altered to alter the degree of chromatic aberration correction. This applies only at the design wavelength because moving the diffractive optical elements closer together or further apart at the design wavelength does not introduce any additional lensing (the diffractive optical elements act like a flat glass plate, as shown in FIG. 51*a* at the design wavelength). Accordingly, the degree of chromatic aberration correction, C, can be varied by simply moving the axial positions of the compensation plates 111, 151 at the design wavelength. There is thus no need to replace any lenses when altering the compensation factor C. In FIG. 52, a value of C less than 1 is shown. In FIG. 50, a value of C=2 is shown. Accordingly, slowly moving the correction plates 111, 151 from the position shown in FIG. 50 to the position shown in FIG. 52 will slowly vary the degree of chromatic aberration correction from a correction of C=2 (which will provide the correction shown in FIG. 23) to a value of C=1 (which will provide the correction shown in FIG. 22) or less.

Figure 53:
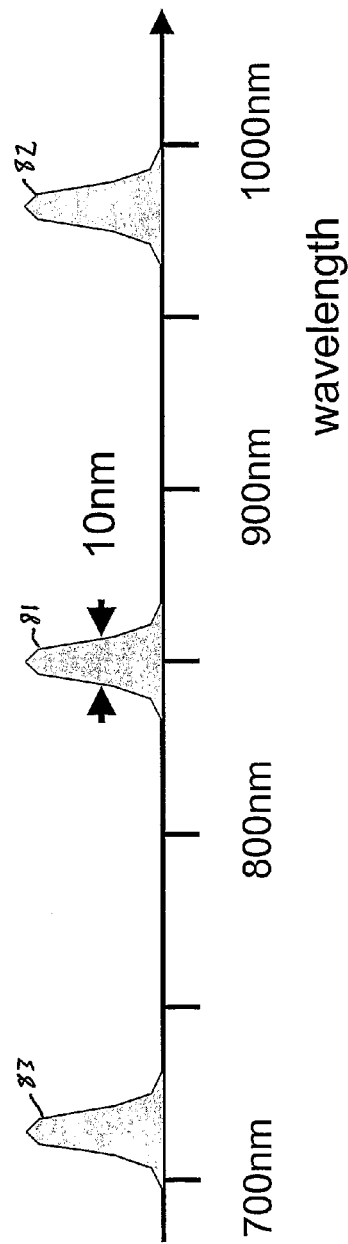
FIG. 53 shows the spectra of laser pulse trains at three different wavelengths.

As explained above with regard to FIGS. 51*a*-51*c*, the compensation plates 111, 151 can be moved to independently adjust the chromatic aberration correction, C, only at the design wavelength. At other wavelengths, the plates will introduce some amount of lensing and thus moving them will change the output beam diameter. FIG. 53 shows a typical range of wavelengths over which it is desirable to operate a system. It shows three potential laser spectra, a first spectrum 81 having a width of 10 nm centred on 850 nm, a second spectrum 82 having a width of 10 nm centred around 980 nm and a third spectrum 83, also having a width of 10 nm centred around 720 nm. These laser pulse streams having spectral widths of 10 nm are typical for pulses having 100 fs duration in the time domain.

The problem is therefore how to design a system which provides sufficient differential magnification to correct the chromatic aberration due to the spectral width of a single laser pulse stream but which yields a constant output beam size whatever the centre wavelength of the laser pulse stream.

Figure 54:
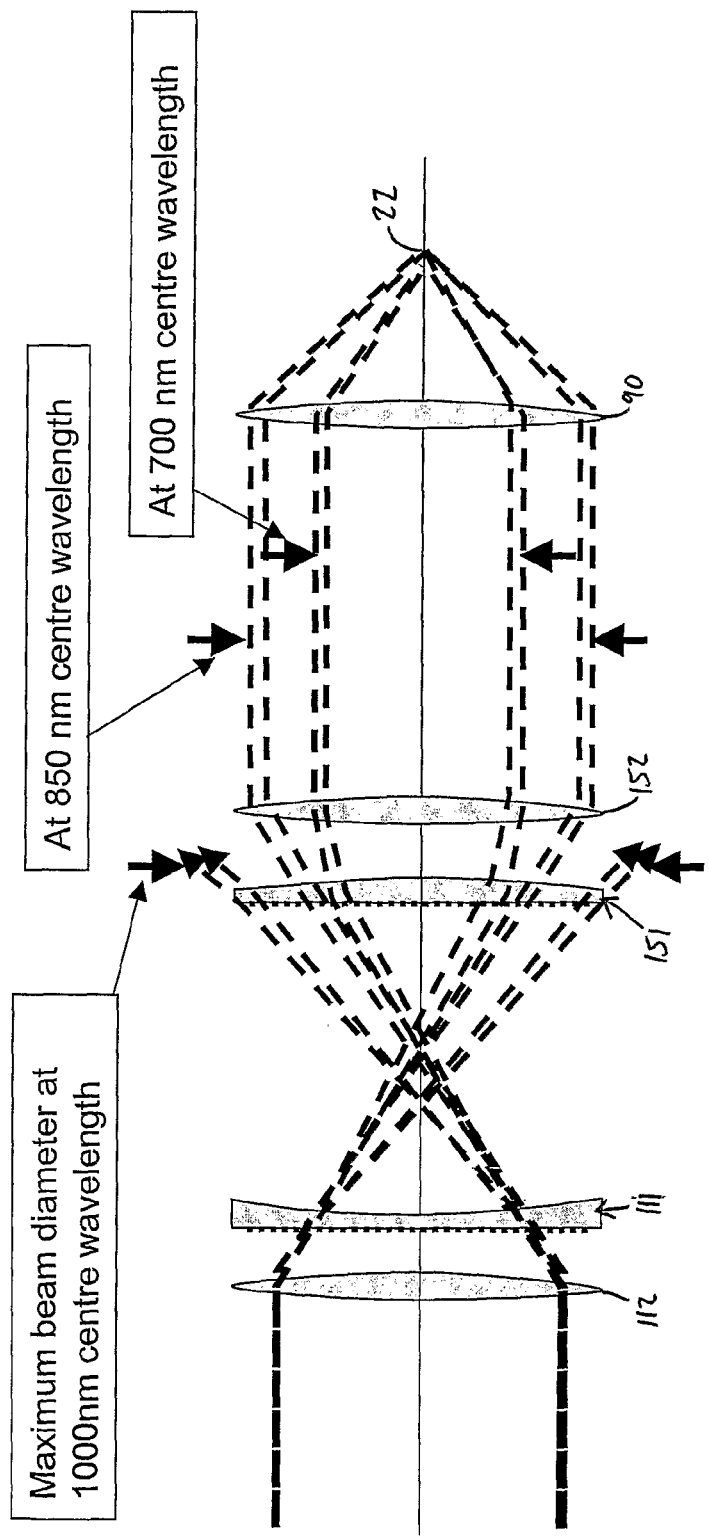
FIG. 54 shows the effect of beam wavelength on the embodiment of FIG. 50.

FIG. 54 illustrates the problem diagrammatically. At the 850 nm design wavelength, the objective lens 90 is more or less fully filled. This means that the spot 22 will be of minimal size (or, in other words, the spot will be maximally focussed). At longer wavelengths (e.g. 1000 nm) the chromatic aberration correction mechanism causes the laser beams to be deflected more and some light leaving the compensation plate 151 is not captured by the subsequent optics. As light is lost, the power provided to the focal position 22 will be reduced. At shorter wavelengths, e.g. 700 nm as shown in FIG. 54, the laser beams will be deflected through a smaller angle and the focal position 22 will be created from a smaller diameter beam at the objective lens 90. As the objective lens is underfilled, the diameter of the diffraction limited focal spot 22 will be increased compared to the minimum it could be at this wavelength and the intensity of the spot will therefore be less than it could be.

For neuroscience applications, one important use of 2-photon microscopes is for uncaging neurotransmitter chemicals to selectively excite particular neurons. This generally requires much higher light intensity at the focal position than 2-photon imaging. It has been found that the most effective molecules for 2-photon uncaging are sensitive around the short wavelength end of a Ti-sapphire operating range (around 600-750 nm). Its therefore highly desirable to be able to fill the aperture of the objective lens at short wavelengths.

If the compensator is designed to fill the aperture at 1000 nm (such that no light is lost at this wavelength, see FIG. 54) the diameter of the beam at 700 nm will be only about 70% of that at 1000 nm. This would produce a focal spot of 1.4 times the diameter which corresponds to a focal spot having twice the area of that produced by a properly filled objective lens. The light at the focal position would therefore have half the intensity and one quarter of the 2-photon excitation rate compared to the situation where the aperture is filled. It is therefore desirable to fill the aperture at the lower end of the wavelength range and at the same time not lose any light at the upper end of the wavelength range. It would be preferable to design a system in which this can be achieved while at the same time allowing the degree of chromatic aberration compensation to be adjusted at least over the range C=1-2 and which does not require any lenses to be removed or replaced during use. Preferably, lenses would be simply moved within the system to provide the correct configuration.

Figure 55:
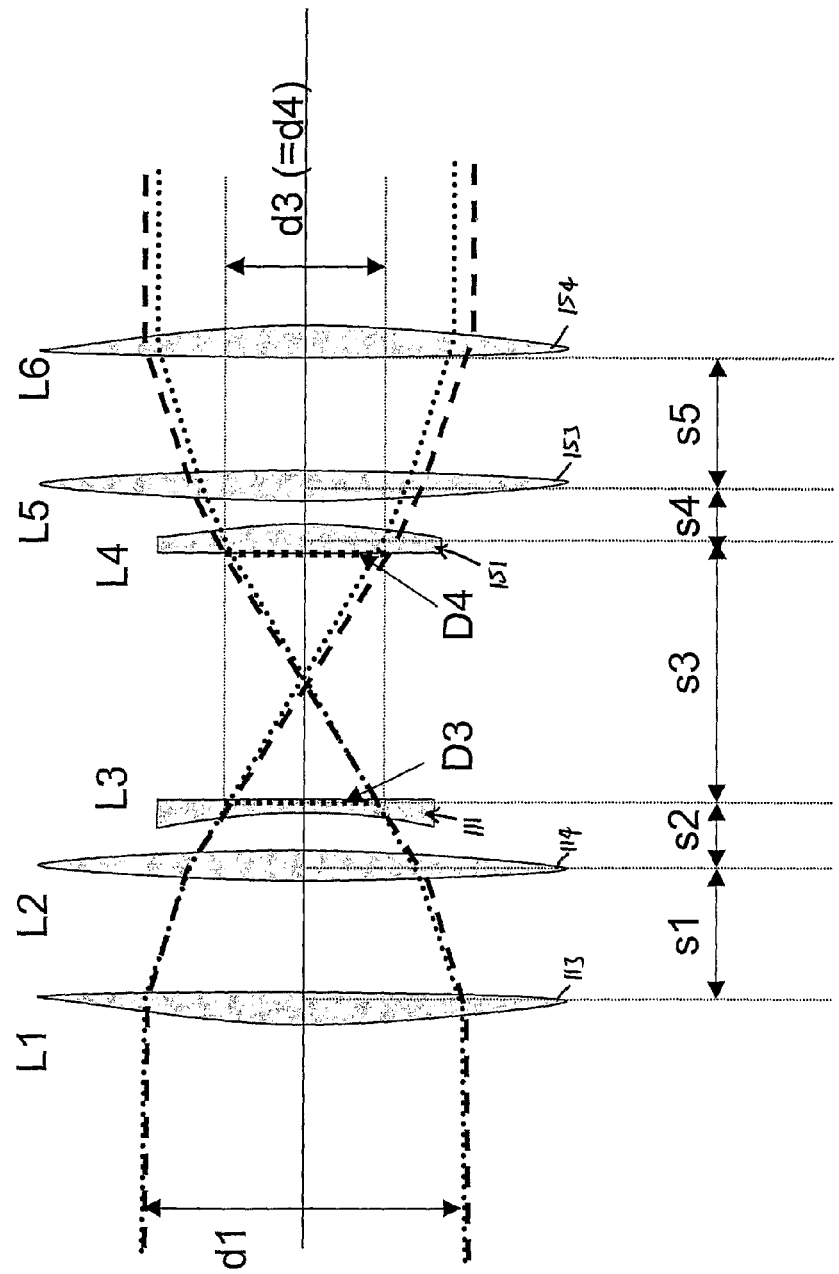
FIG. 55 shows an embodiment of a chromatic aberration correcting system using zoom lenses and diffractive optical elements.

One solution for achieving this is shown in FIG. 55. In this system, the lens 112 in FIG. 54 is replaced by a pair of zoom lenses 113, 114. Similarly, the lens 152 in FIG. 54 is replaced by a pair of zoom lenses 153, 154. The system of FIG. 55 thus includes a first pair of positive focal length zoom lenses 113, 114, a pair of compensation plates 111, 151 and a second pair of positive focal length zoom lenses 153, 154. The positions of the zoom lenses 113, 114, 153, 154 are adjustable to alter their effective focal length. Further, the separation between the two compensation plates 111, 151 is adjustable to vary the compensation factor C and also to take account of different wavelengths of light being utilised in the device. FIG. 55 shows the nomenclature used in the following description to describe the lenses L and the diffractive optical elements D.

A method for designing a zoom compensator will now be described. Firstly, the aperture diameter d3 of the diffractive optical elements 115, 155 can be selected to be a fraction R of the diameter of the input beam d1. It has been found that a fraction R=0.5 allows a system to be designed that covers a 700-900 nm range of wavelengths. A smaller fraction can be selected to cover a wider proportionate range.

The maximum separation of s3 of the compensation plates 111, 151 can then be selected to be greater than the minimum working f number (the ratio of focal length to diameter of a lens) of the diffractive optical element (and other lenses) multiplied by the diameter d3.

For a maximum compensation factor (C=2) the focal length of the lenses L3 and L4 can be made equal to the maximum separation s3 of the compensation plates. As described above, L3 has negative focussing power and L4 has positive focussing power, and the focal lengths of both L3 and L4 are equal to s3.

The focal length of the diffractive optical elements (F(D3) and F(D4)) at the mid-point wavelength can be made equal to the maximum separation s3. F(D3) will be positive and F(D4) will be negative. This ensures that at the mid-point wavelength, the compensator plates have zero lensing power.

In use, the zoom lens spacings s1 and s2 are adjusted for each operating wavelength so that parallel input light is focussed to the mid-point between L3 and L4. The separations s4 and s5 are then adjusted to give the required constant parallel output beam diameter. The spacings s1 and s2 can be calculated by calculating the effective focal lens of the zoom lens needed to transform between the correct diameter parallel external beams and the central focal point, given the strength of the compensator plates at the wavelength concerned.

Figure 56:
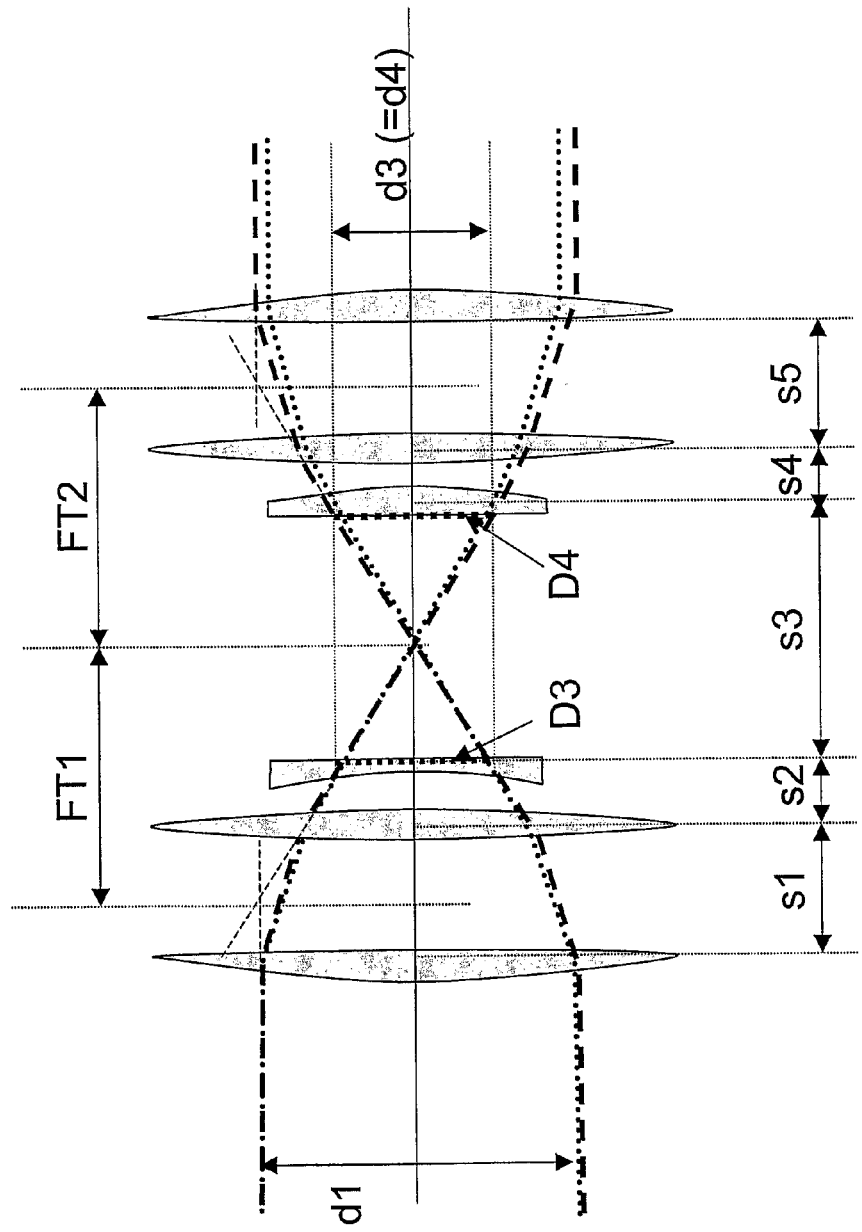
FIG. 56 shows the embodiment of FIG. 55 and the focal length of the zoom lenses.

For example, at the mid-point wavelength where the compensator plates have zero power, if R=0.5 then the effective focal length of the input and output zoom lens pairs is equal to the separation s3. This follows simply because the distance from the centre point to the compensator is s3/2 and as R=0.5 the light cone diameter is doubled before becoming parallel. This is shown in FIG. 56.

The effective focal length of the zoom lenses can be calculated for different operating wavelengths by taking into account the extra required divergence or convergence of the light cone outside of the compensating plates. At a shorter operating wavelength (e.g. 700 nm), s3 needs to be made longer because the beam will not be diffracted through such a large angle with shorter wavelengths. Similarly, for longer wavelengths, the distance s3 needs to be made shorter because the beams will be diffracted more at longer wavelengths. Once s3 has been selected, it is possible to calculate the focal length of the first zoom pair, FT1 and the focal length of the second zoom pair, FT2. In general, a longer s3 will require a longer FT2 and a smaller s3 will require a smaller FT2. The positions of the zoom lenses to meet this condition can then be determined using standard textbook geometric optic equations for zoom lenses.

Figure 57:
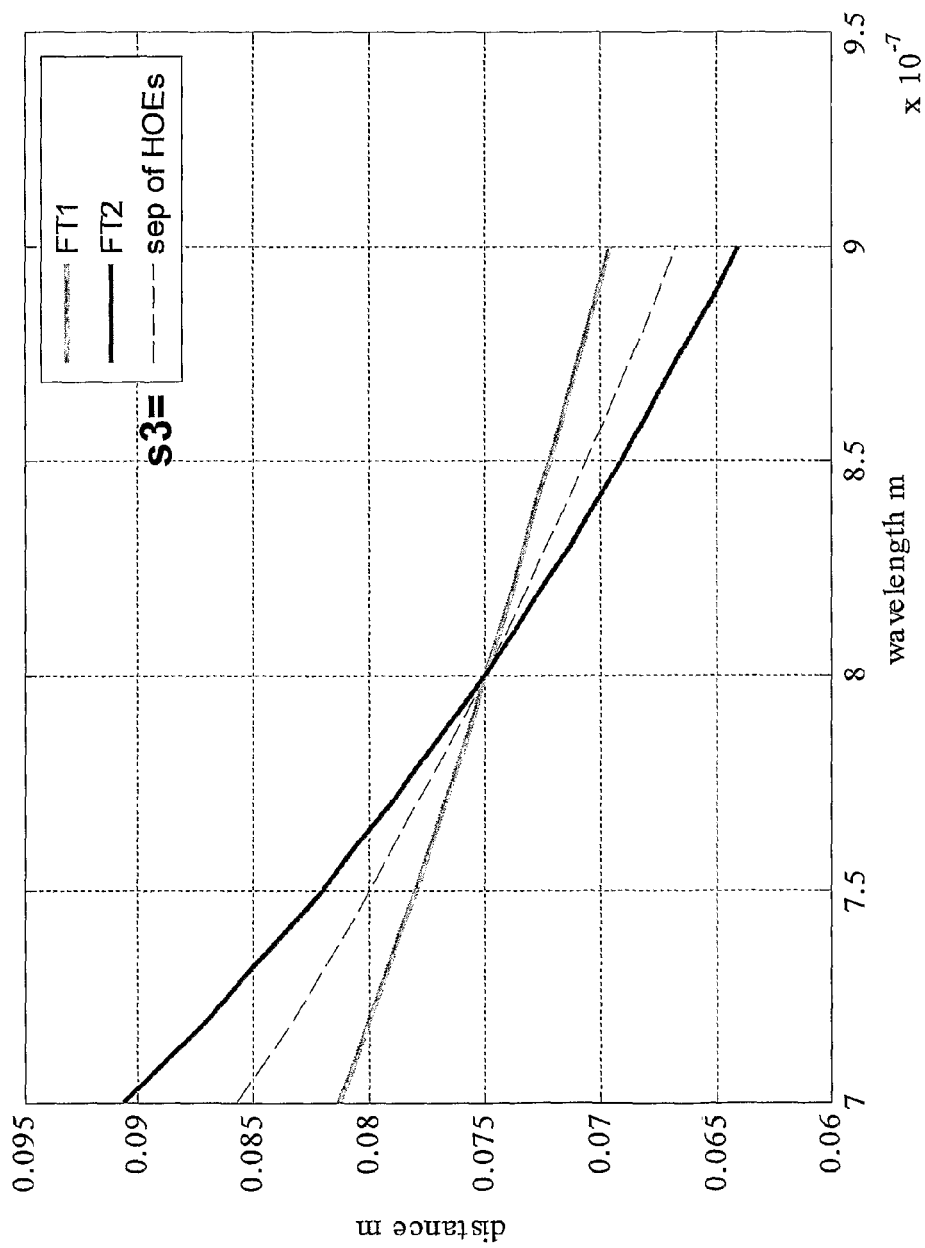
FIG. 57 is a graph useful for explaining the embodiment of FIG. 55.
Figure 58:
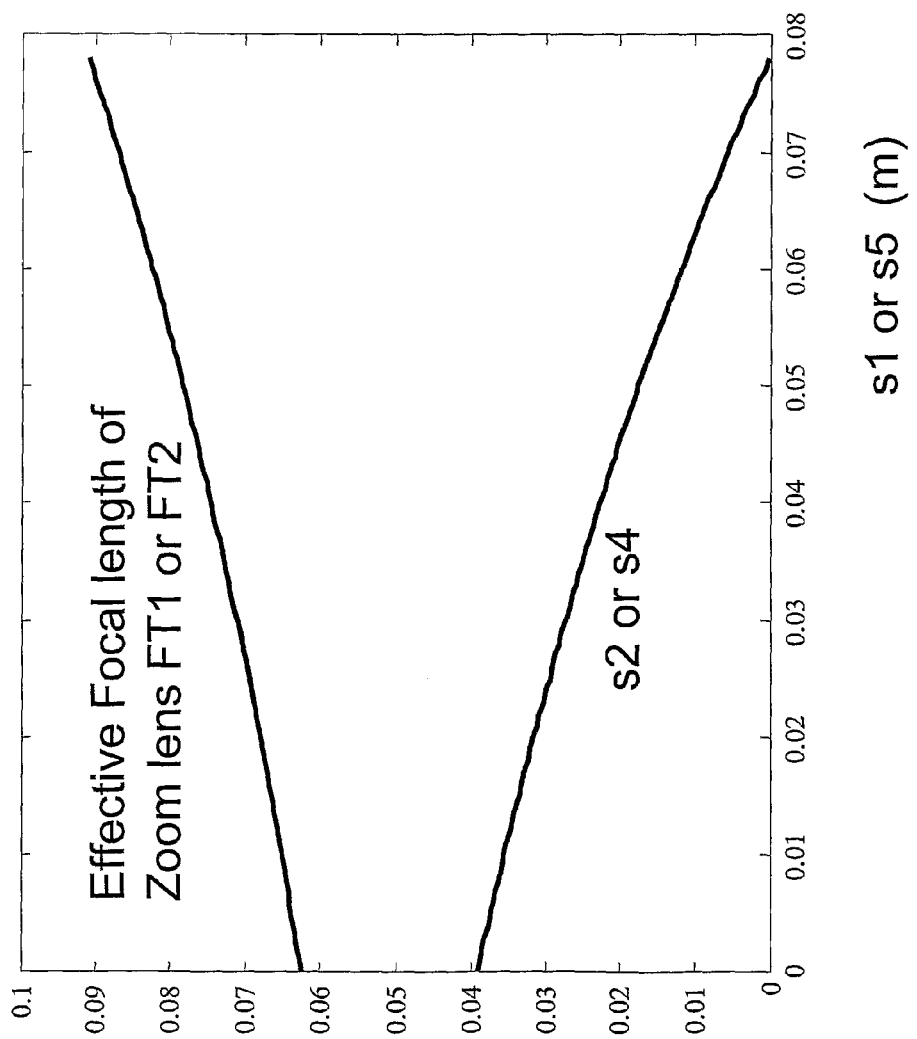
FIG. 58 is another graph useful for explaining the embodiment of FIG. 55.

FIGS. 57 and 58 show actual values for an example when the chosen separation s3 is 75 mm at a centre wavelength of 800 nm. It can be seen that, at the centre wavelength, FT1=FT2=s3. For longer wavelengths, all of these values are reduced and for shorter wavelengths all of these values are increased.

FIG. 58 shows how the values of s2 or s4 and the values of FT1 and FT2 vary as s1 or s5 vary utilising two 125 mm focal length lenses. Accordingly, it is possible to set FT1 and FT2 and thereafter derive s1, s2, s4 and s5.

Figure 59:
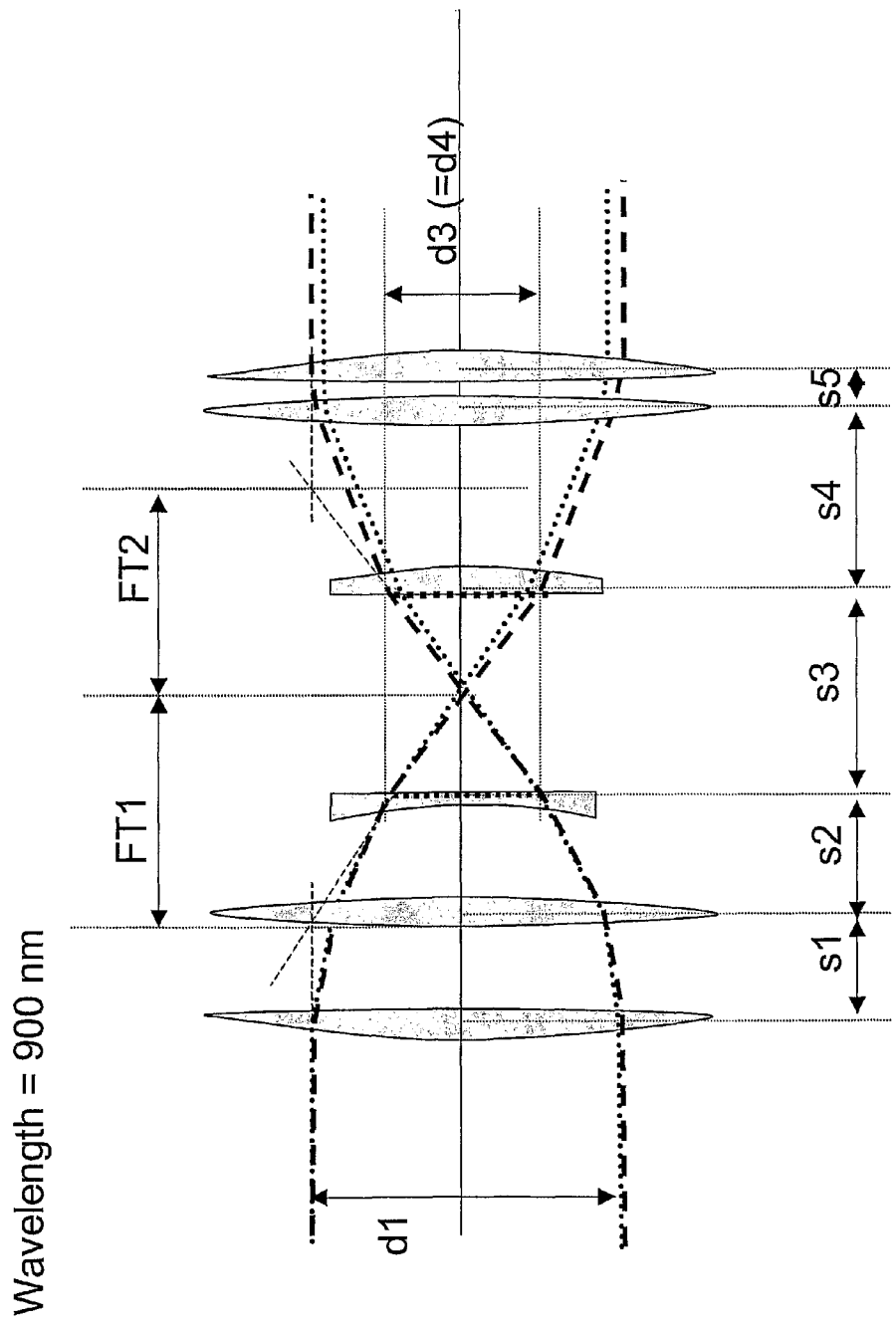
FIG. 59 shows the embodiment of FIG. 55 when a wavelength of 900 nm is used.
Figure 60:
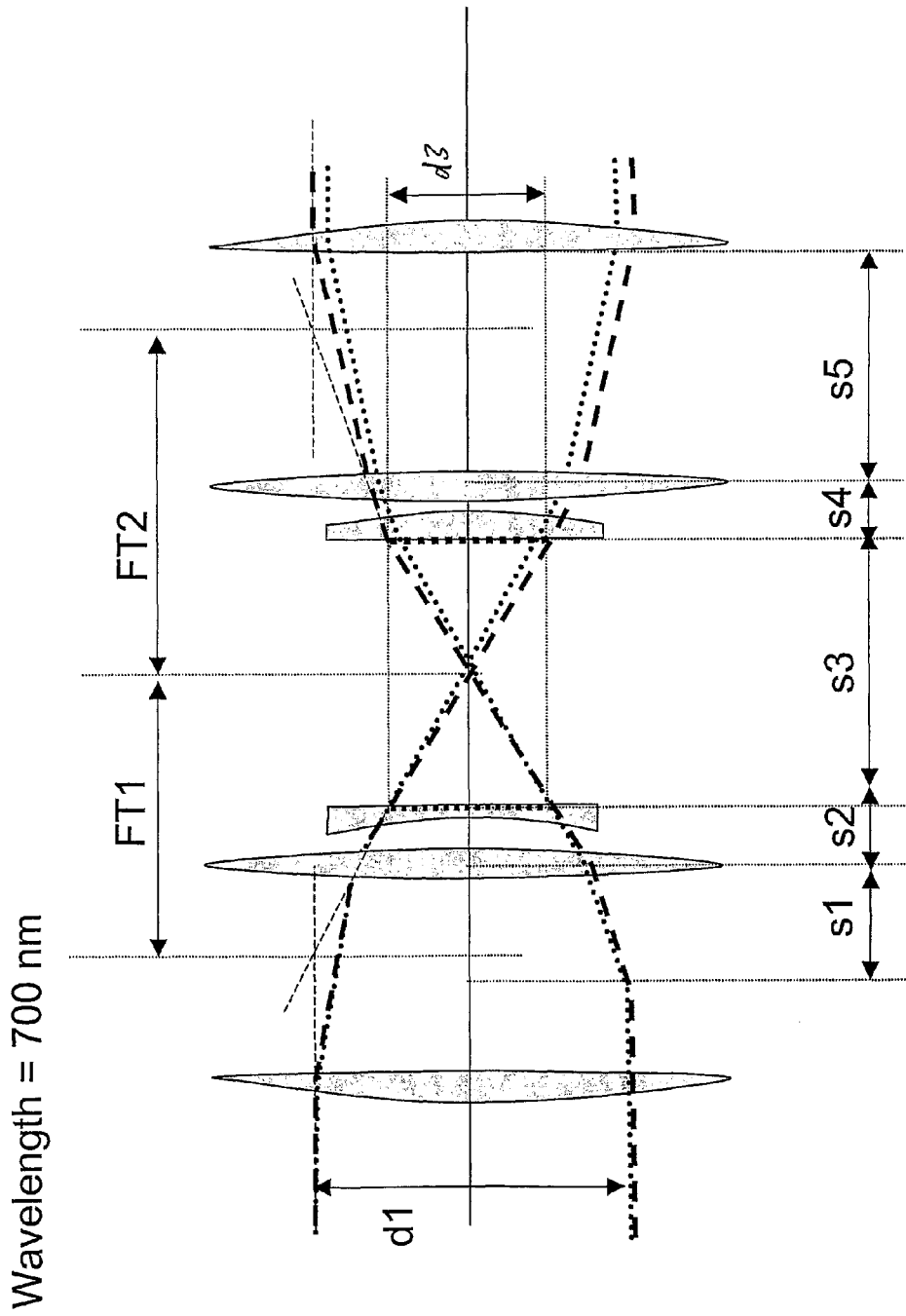
FIG. 60 shows the embodiment of FIG. 55 when a short wavelength is used.

FIG. 59 shows the positions of the lenses for a longer laser wavelength of 900 nm. FIG. 60 shows the lens positions of a wavelength for a shorter wavelength of 700. It will be observed by comparing FIGS. 59 and 60 that the diameter of the output beam is substantially the same whether a long or short wavelength is used. Furthermore, due to the positioning of the compensation plates 111, 151, the same amount of selectable chromatic aberration correction C is achieved in both cases.

It will be appreciated that the zoom compensator of the present invention enables an aperture within the system (for example the objective lens aperture) to be fully filled even when the centre wavelength of the laser beam is changed. In general, the compensator can be modified to fill any aperture in the system. The system aperture is defined here as the diameter of the maximum diameter optical beam at the entrance of the system (or subsystem concerned) that can get through the complete system to the final image without any of the rays being cut off by any intermediate apertures internal to the optical system. Accordingly, the corrective optics of this zoom compensator is capable of ensuring that the beam fills the same design system aperture for substantially all wavelengths falling within the wavelength range of interest. This is illustrated in FIGS. 59 and 60 by showing the beam filling the objective lens aperture, but it may be applied to any system aperture.

Figure 61:
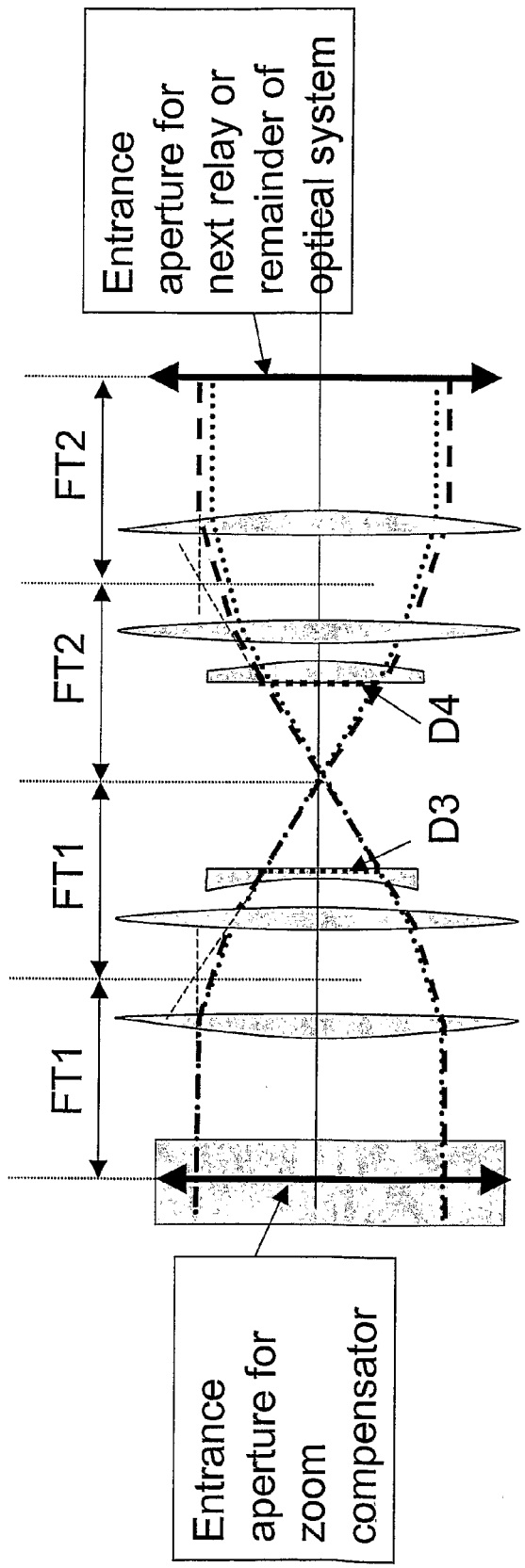
FIG. 61 shows the total length of the chromatic aberration correcting system.

With the solution described above, the values FT1 and FT2 vary with the wavelength of the electromagnetic radiation used. This causes the overall length of the telecentric relay zoom compensator to vary, as shown in FIG. 61. In FIG. 61, the length from the output of the last AOD grating to the entrance to the microscope is illustrated. As will be apparent from FIG. 61, the overall length will be equal to 2×FT1 plus 2×FT2.

Accordingly, to implement this system it would be necessary to move the objective lens relative to the AODs each time the laser wavelength is changed. While this is feasible, it would be convenient to provide a telecentric relay that is of constant length whatever the wavelength of light used.

One solution is to use four mirrors in a standard "optical trombone" arrangement before, or preferably after, the zoom compensator in order to make the overall path length constant.

Another possibility is to design a system such that the sum of FT1 and FT2 is constant. This can be done by varying R with the wavelength. Since varying R will vary C (the compensation factor), s3 can be varied in order to balance this to keep C on target. C will be constant if the product of R and s3 is constant.

The above description of this zoom compensator has several specific aspects which should not be taken as limitations to our claims. Firstly, the example shows that the diameter of the input aperture (FIG. 61) is equal to the diameter of the output aperture. This could simply be changed by adjusting the focal lengths of FT1 and FT2. Secondly, the focal lengths of the sub components 115, 116, 155 and 166 of each compensator plate 111, 151 have been taken as equal to one another in magnitude at the design mid wavelength. The system could however be designed with different focal lengths here, the key point being that the resulting overall system balances the positive and negative chromatic compensation in the overall telecentric relay so that the magnification chromatic aberration is reduced throughout the working field, preferably with the zero aberration point still in the middle so that the edge of field aberrations are minimised.

Accordingly, the present invention proposes the use of zoom lens systems to adjust the overall magnification of the chromatic aberration correction system so as to achieve a full objective lens aperture even at different wavelengths.

The invention claimed is:

1. A system for manipulating a beam of electromagnetic radiation, said system comprising:
    a first acousto-optic deflector;
    a second acousto-optic deflector positioned in series with, and downstream of, said first acousto-optic deflector and being separated from said first acousto-optic deflector by an effective optical separation;
    a driver for providing acoustic waves in said first and second acousto-optic deflectors, said acoustic waves being chirped at different ramp rates to account for said effective optical separation between said first and second acousto-optic deflectors.

2. A system according to claim 1, said system further comprising:
    a third acousto-optic deflector;
    a fourth acousto-optic deflector positioned downstream of said third acousto-optic deflector and being separated from said third acousto-optic deflector by an effective optical separation;
    wherein said driver is arranged to provide acoustic waves in said third and fourth acousto-optic deflectors, said acoustic waves being chirped at different ramp rates to account for said effective optical separation between said third and fourth acousto-optic deflectors.

3. A system according to claim 2, wherein said driver is arranged to provide acoustic waves that cause said beam of electromagnetic radiation to be focussed to a stationary point in space.

4. A system according to claim 3, wherein said driver provides an acoustic wave with a ramp rate $a_1$ to said first acousto-optic deflector and provides an acoustic wave with a ramp rate $a_2$ to said second acousto-optic deflector, and wherein said ramp rates are related by:

$$\frac{a_1}{a_2} = \frac{2d_2'}{2d_2' + d_1}$$

where $d_1$ is the effective optical separation between said first and second acousto-optic deflectors and $d_2'$ is the effective optical distance to the focal line from the second acousto-optic deflector;
    further wherein said driver provides an acoustic wave with a ramp rate $a_3$ to said third acousto-optic deflector and provides an acoustic wave with a ramp rate $a_4$ to said fourth acousto-optic deflector, and wherein said ramp rates are related by:

$$\frac{a_3}{a_4} = \frac{2d_4'}{2d_4' + d_3}$$

where $d_3$ is the effective optical separation between said third and fourth acousto-optic deflectors and $d_4'$ is the distance to the focal point from the fourth acousto-optic deflector.

5. A system according to claim 2, wherein the acousto-optic deflectors are arranged in the following order in the path of the laser beam:
    first,
    third,
    second,
    fourth.

6. A system according to claim 2, wherein said driver is arranged to select the frequencies of said acoustic waves so as to scan a target in the X and/or Y direction.

7. A system according to claim 6, wherein said driver is arranged to select frequencies for said first and second acousto-optic deflectors such as to achieve an angular scan rate of $\delta\theta/\delta t$ by adjusting the ramp rate $a_1$ of the first acousto-optic deflector to be:

$$a_1 = \frac{\frac{V}{\lambda}\left(\frac{V}{2d_2'} - \frac{\delta\theta}{\delta t}\right)}{2 + \frac{d_1}{d_2'} - \frac{d_1}{V}\frac{\delta\theta}{\delta t}}$$

and by adjusting the ramp rate $a_2$ of the second acousto-optic deflector to be:

$$a_2 = \frac{V^2}{2\lambda d_2'} + \frac{V}{2\lambda}\frac{\delta\theta}{\delta t}$$

where V is the speed of sound in the first and second acousto-optic deflectors, $\lambda$ is the wavelength of the laser beam to be deflected, $d_2'$ is the distance to the focal line/point from the second acousto-optic deflector and $d_1$ is the effective optical separation between said first and second acousto-optic deflectors.

8. A system according to claim 6, wherein said driver provides acoustic waves such as to scan a target in the X and/or Y direction, said scan being composed of a series of mini-scans, with a non-active period between each active period of each mini-scan.

9. A system according to claim 8, wherein said non-active period is for adjusting the absolute value of frequencies supplied to the acousto-optic deflectors without moving the focus position.

10. A system according to claim 8, wherein said driver provides four acoustic waves so as to scan a point over a target in two or three dimensions, said scan being composed of a series of mini-scans, with a non-active period between each active period of each mini-scan.

11. A system according to claim 10, wherein said non-active period is for adjusting the absolute value of frequencies supplied to the first, second, third and fourth acousto-optic deflectors without moving the focus position.

12. A system according to claim 10, wherein the absolute values of frequencies supplied to the first and second acousto-optic deflectors are changed in accordance with:

$$\frac{\Delta f_1}{\Delta f_2} \approx \frac{2d_2'}{2d_2' + d_1}$$

where $\Delta f_1$ is the change in frequency of the acoustic wave in the first acousto-optic deflector, $\Delta f_2$ is the change in frequency of the acoustic wave in the second acousto-optic deflector, $d_1$ is the effective optical separation between said first and second acousto-optic deflectors and $d_2'$ is the distance to the focal line/point from said second acousto-optic deflector;

further wherein the absolute values of frequencies supplied to the third and fourth acousto-optic deflectors are changed in accordance with:

$$\frac{\Delta f_3}{\Delta f_4} \approx \frac{2d'_4}{2d'_4 + d_3}$$

where $\Delta f_3$ is the change in frequency of the acoustic wave in the third acousto-optic deflector, $\Delta f_4$ is the change in frequency of the acoustic wave in the fourth acousto-optic deflector, $d_3$ is the effective optical separation between said third and fourth acousto-optic deflectors and $d_4'$ is the distance to the focal point from said fourth acousto-optic deflector.

13. A system according to claim 1, wherein said acousto-optic deflectors are made from a high efficiency anisotropic acousto-optic crystal, such as $TeO_2$ crystals.

14. A system according to claim 1, wherein said beam of electromagnetic radiation is a laser beam and the system further comprises a laser for supplying said laser beam.

15. A system according to claim 14, wherein said laser is arranged to supply a pulsed laser beam.

16. A system according to claim 15, wherein said pulsed laser beam comprises pulses having a length of 2 ps or less preferably having a length of 500 fs or less, more preferably about 100 fs or less.

17. A system according to claim 14, wherein said laser beam has a centre frequency in the range 400 to 1200 nm, preferably 700 to 1000 nm.

18. A method of manipulating a beam of electromagnetic radiation, said method comprising:
   passing said electromagnetic radiation through a first acousto-optic deflector and then through a second acousto-optic deflector downstream of said first acousto-optic deflector, the deflectors containing first and second acoustic waves respectively;
   wherein said first and second acoustic waves are chirped at different ramp rates to account for the effective optical separation between said first and second acousto-optic deflectors.

19. A method according to claim 18, said method further comprising passing said electromagnetic radiation through a third acousto-optic deflector and a fourth acousto-optic deflector downstream of said third acousto-optic deflector, the deflectors containing third and fourth acoustic waves respectively;
   wherein said third and fourth acoustic waves are chirped at different ramp rates to account for the effective optical separation between said third and south acousto-optic deflectors.

20. A method according to claim 19, wherein said beam of electromagnetic radiation is focussed to a stationary point in space.

21. A method according to claim 20, wherein said first acoustic wave has a ramp rate $a_1$, said second acoustic wave has a ramp rate $a_2$ and said ramp rates are related by:

$$\frac{a_1}{a_2} = \frac{2d'_2}{2d'_2 + d_1}$$

where $d_1$ is the effective optical separation between said first and second acousto-optic deflectors and $d_2'$ is the effective optical distance to the focal line from the second acousto-optic deflector;
further wherein said driver provides an acoustic wave with a ramp rate $a_3$ to said third acousto-optic deflector and provides an acoustic wave with a ramp rate $a_4$ to said fourth acousto-optic deflector, and wherein said ramp rates are related by:

$$\frac{a_3}{a_4} = \frac{2d'_4}{2d'_4 + d_3}$$

where $d_3$ is the effective optical separation between said third and fourth acousto-optic deflectors and $d_4'$ is the effective optical distance to the focal line from the fourth acousto-optic deflector.

22. A method according to claim 19, wherein the beam of electromagnetic radiation is passed through the acousto-optic deflectors in the following order;
   first,
   third,
   second,
   fourth.

23. A method according to claim 18, wherein said beam of electromagnetic radiation scans a target in the X and/or Y direction.

24. A method according to claim 23, wherein said first and second acoustic waves are arranged to cause said beam of electromagnetic radiation to achieve an angular scan rate of $\delta\theta/\delta t$, said first acoustic wave having a ramp rate $a_1$ given by:

$$a_1 = \frac{\frac{V}{\lambda}\left(\frac{V}{2d'_2} - \frac{\delta\theta}{\delta t}\right)}{2 + \frac{d_1}{d'_2} - \frac{d_1}{V}\frac{\delta\theta}{\delta t}}$$

and said second acoustic wave having a ramp rate $a_2$ given by:

$$a_2 = \frac{V^2}{2\lambda d'_2} + \frac{V}{2\lambda}\frac{\delta\theta}{\delta t}$$

where V is the speed of sound in the first and second acousto-optic deflectors, $\lambda$ is the wavelength of the laser beam to be deflected, $d_2'$ is the distance to the focal line/point from the second acousto-optic deflector and $d_1$ is the effective optical separation between said first and second acousto-optic deflectors.

25. A method according to claim 19, wherein said beam of electromagnetic radiation scans a target in the X and/or Y direction, said scan being composed of a series of mini-scans, with a non-active period between each mini-scan.

26. A method according to claim 25, wherein said non-active period is for adjusting the absolute value of frequencies supplied to the acousto-optic deflectors without moving the focus position.

27. A method according to claim 26, wherein said non-active period comprises a frequency resetting time and an AOD fill time.

28. A method according to claim 26, wherein the absolute values of frequencies of said first and second acoustic waves are changed in accordance with:

$$\frac{\Delta f_1}{\Delta f_2} \approx \frac{2d'_2}{2d'_2 + d_1}$$

where $\Delta f_1$ is the change in frequency of the first acoustic wave in the first acousto-optic deflector, $\Delta f_2$ is the change in frequency of the second acoustic wave in the second acousto-optic deflector, $d_1$ is the effective optical separation between said first and second acousto-optic deflectors and $d_2'$ is the distance to the focal line/point from said second acousto-optic deflector.

29. A method according to claim 28, wherein said beam of electromagnetic radiation is passed through four acoustic waves such that a point is scanned in two or three directions, the scan being composed of a series of mini-scans with a non-active period between each active period of each mini-scan.

30. A method of scanning a target volume with a beam of electromagnetic radiation, said method comprising:
  passing said electromagnetic radiation through a first acousto-optic deflector and a second acousto-optic deflector downstream of said first acousto-optic deflector, the deflectors containing first and second acoustic waves respectively so as to move a focus position of said beam along a scan path in said target volume at an angular scan rate given by $\delta\theta/\delta t$;
  wherein said first and second acoustic waves are chirped to have a constantly increasing or decreasing frequency;
  and wherein the ramp rates of said chirped acoustic waves are selected in accordance with:

$$a_1 = \frac{\frac{V}{\lambda}\left(\frac{V}{d_2'} - \frac{\delta\theta}{\delta t}\right)}{2 + \frac{d_1}{d_2'} - \frac{d_1}{V}\frac{\delta\theta}{\delta t}}$$

$$a_2 = \frac{V^2}{2\lambda d_2'} + \frac{V}{2\lambda}\frac{\delta\theta}{\delta t}$$

where $a_1$ is the ramp rate in the first acousto-optic deflector, $a_2$ is the ramp rate in the second acousto-optic deflector, V is the speed of sound in the first and second acousto-optic deflectors, $\lambda$ is the wavelength of the electromagnetic radiation beam, $d_1$ is the effective optical separation between the first and second acousto-optic deflectors and $d_2'$ is the distance to the focus position from the second acousto-optic deflector.

31. A method according to claim 30, wherein the first and second acousto-optic deflectors are separated by a non-zero effective optical separation.

32. A method accordingly to claim 31, wherein the ramp rate $a_2$ of the acoustic wave in the second acousto-optic deflector is determined such that the additional curvature provided to the wavefront of said electromagnetic radiation by said second acousto-optic deflector is a predetermined amount more or less than the curvature of the wavefront as it arrives at said second acousto-optic deflector from said first acousto-optic deflector, such as to provide for the scanning of said focal position.

33. A method according to claim 30, wherein the angular scan rate is constant.

34. A system for scanning a target volume with a beam of electromagnetic radiation, said system comprising:
  a first acousto-optic deflector;
  a second acousto-optic deflector positioned downstream of said first acousto-optic deflector and being separated from said first acousto-optic deflector by an effective optical separation;
  a driver for providing respective first and second acoustic waves in said first and second acousto-optic deflectors, said first acoustic wave having a ramp rate given by;

$$a_1 = \frac{\frac{V}{\lambda}\left(\frac{V}{d_2'} - \frac{\delta\theta}{\delta t}\right)}{2 + \frac{d_1}{d_2'} - \frac{d_1}{V}\frac{\delta\theta}{\delta t}}$$

and said second acoustic wave having a ramp rate given by:

$$a_2 = \frac{V^2}{2\lambda d_2'} + \frac{V}{2\lambda}\frac{\delta\theta}{\delta t}$$

where $a_1$ is the ramp rate in the first acousto-optic deflector, $a_2$ is the ramp rate in the second acousto-optic deflector, V is the speed of sound in the first and second acousto-optic deflectors, $\lambda$ is the wavelength of the electromagnetic radiation beam, $d_1$ is the effective optical separation between the first and second acousto-optic deflectors and $d_2'$ is the distance to the focus position from the second acousto-optic deflector.

35. A system according to claim 34, wherein the first and second acousto-optic deflectors are separated by a non-zero effective optical separation.

* * * * *